US012569243B2

(12) United States Patent　　　(10) Patent No.:　US 12,569,243 B2
Quadri et al.　　　　　　　　　　　(45) Date of Patent:　　Mar. 10, 2026

(54) SYSTEMS FOR PERCUTANEOUS VENTRICULOPLASTY USING VENTRICULAR ANCHORS

(71) Applicant: inQB8 Medical Technologies, LLC, Winchester, MA (US)

(72) Inventors: Arshad Quadri, West Hartford, CT (US); Jeremy Brent Ratz, Winchester, MA (US); Garrett Dallas Johnson, Costa Mesa, CA (US); James George Wittel, Seattle, WA (US); Nicholas Guidoboni, Tyngsboro, MA (US); Devin Haupt Marr, Westford, MA (US); Audrey Bell, Wellesley, MA (US); Matthew Steven Lapointe, Framingham, MA (US); Alexandra Grace Wirth, San Diego, CA (US); Christian G. Monroe, San Diego, CA (US); Alexander Ryan McCall, San Diego, CA (US); Sydney Jade Fletcher, Winchester, MA (US)

(73) Assignee: inQB8 Medical Technologies, LLC, Winchester, MA (US)

( * ) Notice: Subject to any disclaimer, the term of this patent is extended or adjusted under 35 U.S.C. 154(b) by 0 days.

(21) Appl. No.: 19/038,476

(22) Filed: Jan. 27, 2025

(65) Prior Publication Data

US 2025/0302464 A1　　　Oct. 2, 2025

Related U.S. Application Data

(60) Provisional application No. 63/691,947, filed on Sep. 6, 2024, provisional application No. 63/573,376, filed on Apr. 2, 2024.

(51) Int. Cl.
*A61B 17/04*　　　(2006.01)
*A61F 2/24*　　　(2006.01)

(52) U.S. Cl.
CPC ........ *A61B 17/0401* (2013.01); *A61F 2/2487* (2013.01); *A61B 2017/0409* (2013.01)

(58) Field of Classification Search
CPC .......... A61B 17/0401; A61B 17/00234; A61B 17/0487; A61B 17/08; A61B 2017/0409;
(Continued)

(56) References Cited

U.S. PATENT DOCUMENTS 5,961,440 A　*　10/1999　Schweich, Jr. ....... A61F 2/2487
　　　　　　　　　　　　　　　　　　600/16
6,174,323 B1 *　1/2001　Biggs ............... A61B 17/12022
　　　　　　　　　　　　　　　　　　606/232
(Continued)

FOREIGN PATENT DOCUMENTS

EP　　　1608297 A2　12/2005
EP　　　1887981 A2　2/2008
(Continued)

OTHER PUBLICATIONS

"ALIVE—A Clinical Study for Heart Failure Patients with Left Ventricular Aneurysms", BioVentrix, Aug. 7, 2017, DCO # 3732 (MKT-0092-B), in 3 pages. URL: https://bioventrix.com/wp-content/uploads/2022/11/BioVentrix_MKT-0092-B_ALIVE-Patient-Brochure.pdf.
(Continued)

*Primary Examiner* — Dianne Dornbusch
(74) *Attorney, Agent, or Firm* — Knobbe, Martens, Olson & Bear, LLP

(57)　　　　　　　ABSTRACT

A system for percutaneous ventriculoplasty. Anchors can be placed in the ventricular septum and the ventricular wall. Sutures tethered to the anchors can be tensioned to reduce the size of a dilated left ventricle. Multiple anchors can be
(Continued)

positioned in the ventricular wall and the sutures can be independently tensioned to allow tailored treatment of the dilated ventricle.

15 Claims, 37 Drawing Sheets

(58) Field of Classification Search
CPC .. A61B 2017/00243; A61B 2017/0496; A61B 2017/0417; A61B 2017/0414; A61B 2017/0448; A61B 2017/0464; A61B 2017/0454; A61B 2017/048; A61B 2017/0419; A61B 2017/0488; A61B 2017/0458; A61B 2017/0462; A61B 2017/042; A61B 2017/0446; A61F 2/2445; A61F 2/2487
See application file for complete search history.

(56) References Cited

U.S. PATENT DOCUMENTS

| | | | | |
|---|---|---|---|---|
| 6,616,684 | B1 * | 9/2003 | Vidlund | A61B 17/064 |
| | | | | 606/213 |
| 7,077,862 | B2 * | 7/2006 | Vidlund | A61B 17/00234 |
| | | | | 623/2.11 |
| 7,112,207 | B2 | 9/2006 | Allen et al. | |
| 7,695,425 | B2 | 4/2010 | Schweich et al. | |
| 7,695,493 | B2 | 4/2010 | Saadat et al. | |
| 7,722,523 | B2 | 5/2010 | Mortier et al. | |
| 7,736,379 | B2 | 6/2010 | Ewers et al. | |
| 7,785,248 | B2 | 8/2010 | Annest et al. | |
| 7,942,884 | B2 * | 5/2011 | Vahid | A61B 17/0487 |
| | | | | 606/232 |
| 7,981,020 | B2 | 7/2011 | Mortier et al. | |
| 8,029,556 | B2 | 10/2011 | Rowe | |
| 8,123,668 | B2 | 2/2012 | Annest et al. | |
| 8,206,417 | B2 | 6/2012 | Maahs et al. | |
| 8,333,777 | B2 | 12/2012 | Schaller et al. | |
| 8,382,800 | B2 | 2/2013 | Maahs et al. | |
| 8,394,008 | B2 | 3/2013 | Annest et al. | |
| 8,425,402 | B2 | 4/2013 | Annest et al. | |
| 8,454,656 | B2 | 6/2013 | Tuval | |
| 8,491,455 | B2 | 7/2013 | Annest et al. | |
| 8,506,474 | B2 | 8/2013 | Chin et al. | |
| 8,540,620 | B2 | 9/2013 | Mortier et al. | |
| 8,636,639 | B2 | 1/2014 | Annest et al. | |
| 8,870,936 | B2 | 10/2014 | Rowe | |
| 8,951,285 | B2 | 2/2015 | Sugimoto et al. | |
| 8,951,286 | B2 | 2/2015 | Sugimoto et al. | |
| 8,968,175 | B2 | 3/2015 | Annest et al. | |
| 9,011,520 | B2 | 4/2015 | Miller et al. | |
| 9,039,594 | B2 | 5/2015 | Annest et al. | |
| 9,044,231 | B2 | 6/2015 | Annest et al. | |
| 9,107,658 | B2 | 8/2015 | Schaller et al. | |
| 9,125,632 | B2 | 9/2015 | Loulmet et al. | |
| 9,211,115 | B2 | 12/2015 | Annest et al. | |
| 9,259,218 | B2 | 2/2016 | Robinson | |
| 9,345,470 | B2 | 5/2016 | Tuval | |
| 9,402,722 | B2 | 8/2016 | Annest et al. | |
| 9,486,206 | B2 | 11/2016 | Annest et al. | |
| 9,561,105 | B2 | 2/2017 | Rowe | |
| 9,572,667 | B2 * | 2/2017 | Solem | A61F 2/0077 |
| 9,744,040 | B2 | 8/2017 | Annest et al. | |
| 9,814,454 | B2 | 11/2017 | Sugimoto et al. | |
| 9,889,008 | B2 | 2/2018 | Annest et al. | |
| 9,907,547 | B2 | 3/2018 | Gilmore et al. | |
| 9,913,719 | B2 | 3/2018 | Annest et al. | |
| 10,420,645 | B2 | 9/2019 | Del Nido et al. | |
| 10,441,266 | B2 | 10/2019 | Denti et al. | |
| 10,441,267 | B2 | 10/2019 | Gilmore et al. | |
| 10,463,358 | B2 | 11/2019 | Gilmore et al. | |
| 10,463,492 | B2 | 11/2019 | Tylis et al. | |
| 10,478,305 | B2 | 11/2019 | Annest et al. | |
| 10,555,814 | B2 | 2/2020 | Axelrod et al. | |

| | | | | |
|---|---|---|---|---|
| 10,575,953 | B2 | 3/2020 | Van Bladel et al. | |
| 10,588,618 | B2 | 3/2020 | Gilmore et al. | |
| 10,617,525 | B2 | 4/2020 | Annest et al. | |
| 10,624,744 | B2 | 4/2020 | Annest et al. | |
| 10,682,229 | B2 | 6/2020 | Guidotti et al. | |
| 10,702,274 | B2 * | 7/2020 | Groothuis | A61B 17/0401 |
| 10,779,933 | B2 | 9/2020 | Solem | |
| 10,912,546 | B2 | 2/2021 | Schaller et al. | |
| 10,966,696 | B2 | 4/2021 | Schaller et al. | |
| 10,980,973 | B2 | 4/2021 | Nguyen et al. | |
| 11,006,946 | B2 | 5/2021 | Gilmore et al. | |
| 11,026,673 | B2 | 6/2021 | Karapetian | |
| 11,141,271 | B2 | 10/2021 | Miller et al. | |
| 11,172,921 | B2 | 11/2021 | Rohl et al. | |
| 11,185,414 | B2 | 11/2021 | Van Bladel et al. | |
| 11,273,040 | B2 | 3/2022 | Chin et al. | |
| 11,331,189 | B2 | 5/2022 | Tylis et al. | |
| 11,331,190 | B2 | 5/2022 | Annest et al. | |
| 11,337,686 | B2 | 5/2022 | Gilmore et al. | |
| 11,357,629 | B1 | 6/2022 | Gross | |
| 11,376,127 | B2 | 7/2022 | Trapp et al. | |
| 11,389,152 | B2 | 7/2022 | Gilmore et al. | |
| 11,399,942 | B2 | 8/2022 | Annest et al. | |
| 11,419,723 | B2 | 8/2022 | Annest et al. | |
| 11,446,146 | B2 | 9/2022 | Axelrod Manela et al. | |
| 11,478,353 | B2 | 10/2022 | Van Bladel et al. | |
| 11,484,303 | B2 | 11/2022 | Gilmore et al. | |
| 11,497,485 | B2 | 11/2022 | Gilmore et al. | |
| 11,540,822 | B2 | 1/2023 | Moshe et al. | |
| 11,766,331 | B2 | 9/2023 | Vismara et al. | |
| 11,883,294 | B2 | 1/2024 | Tylis et al. | |
| 11,903,834 | B2 | 2/2024 | Van Bladel et al. | |
| 11,964,112 | B2 | 4/2024 | Nguyen et al. | |
| 12,029,650 | B2 | 7/2024 | Axelrod et al. | |
| 12,035,898 | B2 | 7/2024 | Schaller et al. | |
| 2004/0122473 | A1 * | 6/2004 | Ewers | A61B 17/0401 |
| | | | | 606/222 |
| 2004/0186566 | A1 | 9/2004 | Hindrichs et al. | |
| 2004/0225304 | A1 | 11/2004 | Vidlund et al. | |
| 2005/0148815 | A1 | 7/2005 | Mortier et al. | |
| 2005/0177180 | A1 | 8/2005 | Kaganov et al. | |
| 2005/0251208 | A1 * | 11/2005 | Elmer | A61B 17/0401 |
| | | | | 606/232 |
| 2006/0161040 | A1 | 7/2006 | McCarthy et al. | |
| 2006/0229708 | A1 | 10/2006 | Powell et al. | |
| 2006/0287661 | A1 | 12/2006 | Bolduc et al. | |
| 2007/0118213 | A1 * | 5/2007 | Loulmet | A61F 2/2457 |
| | | | | 606/151 |
| 2007/0265658 | A1 | 11/2007 | Nelson et al. | |
| 2009/0082619 | A1 | 3/2009 | De Marchena | |
| 2009/0099410 | A1 | 4/2009 | De Marchena | |
| 2010/0010538 | A1 | 1/2010 | Juravic et al. | |
| 2011/0015476 | A1 | 1/2011 | Franco | |
| 2013/0090684 | A1 | 4/2013 | Bladel et al. | |
| 2015/0011821 | A1 | 1/2015 | Gorman et al. | |
| 2015/0045879 | A1 | 2/2015 | Longoria et al. | |
| 2015/0105611 | A1 | 4/2015 | Schweich et al. | |
| 2015/0305738 | A1 | 10/2015 | Thomas | |
| 2015/0335430 | A1 | 11/2015 | Loulmet et al. | |
| 2016/0015377 | A1 * | 1/2016 | Cedro, Jr. | A61B 17/0401 |
| | | | | 606/232 |
| 2016/0038130 | A1 | 2/2016 | Schaller et al. | |
| 2017/0095333 | A1 | 4/2017 | Rowe | |
| 2018/0318083 | A1 | 11/2018 | Bolling | |
| 2018/0353297 | A1 | 12/2018 | Griffin | |
| 2019/0240023 | A1 | 8/2019 | Spence et al. | |
| 2019/0240024 | A1 | 8/2019 | Tobis et al. | |
| 2019/0365368 | A1 | 12/2019 | Karapetian | |
| 2020/0022696 | A1 | 1/2020 | Denti et al. | |
| 2020/0046498 | A1 | 2/2020 | Longoria et al. | |
| 2020/0069426 | A1 | 3/2020 | Conklin et al. | |
| 2020/0129170 | A1 | 4/2020 | Gilmore et al. | |
| 2020/0222186 | A1 * | 7/2020 | Edmiston | A61B 17/0401 |
| 2020/0261228 | A1 | 8/2020 | Guidotti et al. | |
| 2020/0268514 | A1 | 8/2020 | Kao | |
| 2020/0315798 | A1 | 10/2020 | Guidotti et al. | |
| 2020/0368048 | A1 | 11/2020 | Griffin et al. | |
| 2021/0093454 | A1 | 4/2021 | Sampson et al. | |
| 2021/0378824 | A1 | 12/2021 | Popp et al. | |

(56) References Cited

U.S. PATENT DOCUMENTS

| | | | |
|---|---|---|---|
| 2022/0023043 A1 | 1/2022 | Miller et al. | |
| 2022/0061831 A1 | 3/2022 | Byju et al. | |
| 2022/0257233 A1 | 8/2022 | Haarer | |
| 2023/0210515 A1 | 7/2023 | Gilmore et al. | |
| 2023/0218398 A1 | 7/2023 | Reich et al. | |
| 2023/0233321 A1 | 7/2023 | Lederman et al. | |
| 2023/0277856 A1 | 9/2023 | Sharif et al. | |
| 2023/0309979 A1 | 10/2023 | Agnihotri et al. | |
| 2023/0380975 A1 | 11/2023 | Vismara et al. | |
| 2023/0404760 A1 | 12/2023 | Vismara et al. | |
| 2023/0414354 A1 | 12/2023 | Conklin | |
| 2024/0008987 A1 | 1/2024 | Guerrero et al. | |
| 2024/0139480 A1* | 5/2024 | Ben Menachem | A61B 5/14539 |
| 2024/0189105 A1 | 6/2024 | Shuey et al. | |
| 2024/0245513 A1 | 7/2024 | Van Bladel | |
| 2025/0302626 A1 | 10/2025 | Quadri et al. | |

FOREIGN PATENT DOCUMENTS

| | | | |
|---|---|---|---|
| EP | 2289467 A1 | 3/2011 | |
| EP | 2081519 B1 | 4/2014 | |
| EP | 1898802 B1 | 9/2015 | |
| EP | 1933756 B1 | 7/2016 | |
| EP | 2979647 B1 | 3/2017 | |
| EP | 3030161 A1 | 3/2017 | |
| EP | 3210543 A1 | 8/2017 | |
| EP | 1799093 B1 | 9/2017 | |
| EP | 2493423 B1 | 11/2017 | |
| EP | 3068311 B1 | 11/2017 | |
| EP | 3236885 A1 | 11/2017 | |
| EP | 3284412 A1 | 2/2018 | |
| EP | 2150312 B1 | 6/2018 | |
| EP | 1901665 B1 | 8/2018 | |
| EP | 3389565 A1 | 10/2018 | |
| EP | 2961331 B1 | 11/2018 | |
| EP | 2814427 B1 | 12/2018 | |
| EP | 3432806 B1 | 10/2019 | |
| EP | 3038540 B1 | 11/2019 | |
| EP | 2680757 B1 | 12/2019 | |
| EP | 3579761 A2 | 12/2019 | |
| EP | 3634255 B1 | 8/2020 | |
| EP | 3346926 B1 | 10/2020 | |
| EP | 2217153 B1 | 3/2021 | |
| EP | 1734872 B1 | 4/2021 | |
| EP | 2194888 B1 | 4/2021 | |
| EP | 3661428 B1 | 7/2021 | |
| EP | 3843664 A1 | 7/2021 | |
| EP | 3854315 A1 | 7/2021 | |
| EP | 3915490 A1 | 7/2021 | |
| EP | 3038539 B1 | 8/2021 | |
| EP | 3905967 A1 | 11/2021 | |
| EP | 3294218 B1 | 2/2022 | |
| EP | 3957252 A1 | 2/2022 | |
| EP | 2313152 B1 | 8/2022 | |
| EP | 3718509 B1 | 8/2022 | |
| EP | 4074285 A1 | 10/2022 | |
| EP | 4157148 A1 | 4/2023 | |
| EP | 3377001 B1 | 11/2023 | |
| EP | 3407802 B1 | 1/2024 | |
| EP | 3782556 B1 | 4/2024 | |
| WO | WO 2020/005551 A1 | 1/2020 | |
| WO | WO 2020/219281 A1 | 10/2020 | |
| WO | WO 2022/256309 A1 | 12/2022 | |
| WO | WO 2023/076122 A1 | 5/2023 | |
| WO | WO 2024/118313 A1 | 6/2024 | |

OTHER PUBLICATIONS

Ancora Heart, "Ancora Heart AccuCinch Animation Sep. 2019", YouTube, published Sep. 12, 2019, in 6 pages [screenshots of video at 00:55, 01:05, 01:15, 01:25, 01:35]. URL: https://www.youtube.com/watch?v=9ERh9m7alQ4.

Bruce, C. G. et al., "Reshaping the Ventricle from Within—MIRTH (Myocardial Intramural Remodeling by TransvenousTether) Ventriculoplasty in Swine", JACC: Basic to Translational Science, Jan. 2023, vol. 8, No. 1, in 14 pages. URL: https://www.jacc.org/doi/full/10.1016/j.jacbts.2022.07.002.

Cardiac Success Ltd., "Cardiac Success, Ventricular Repair Implant", YouTube, published Feb. 3, 2022, in 8 pages [screenshots of video at 0:10, 0:20, 0:30, 0:40, 0:50, 1:00, 1:10]. URL: https://www.youtube.com/watch?v=hj6h23RcYAs&list=TLGGLk4Zh52Xpr0xOTEyMjAyMw&t=15s.

Grossi, E. A. et al., "Outcomes of the RESTOR-MV Trial (Randomized Evaluation of a Surgical Treatment for Off-Pump Repair of the Mitral Valve)", Journal of the American College of Cardiology, Dec. 2010, vol. 56, No. 24, pp. 1984-1993. URL: https://www.jacc.org/doi/10.1016/j.jacc.2010.06.051.

Medicalvisionaus, "Treating Heart Failure with a Parachute Device", YouTube, published Aug. 11, 2014, in 7 pages [screenshots of video at 02:20, 02:30, 02:40, 02:50, 03:00, 03:10]. URL: https://www.youtube.com/watch?v=7uSdJZvRZek.

International Search Report and Written Opinion in PCT Application No. PCT/US2025/022611, dated Aug. 1, 2025, in 20 pages.

* cited by examiner

200

230

236

232

230    236 234    200

238

232

500

544

541

548

546

600

650a
654
652
654
650b

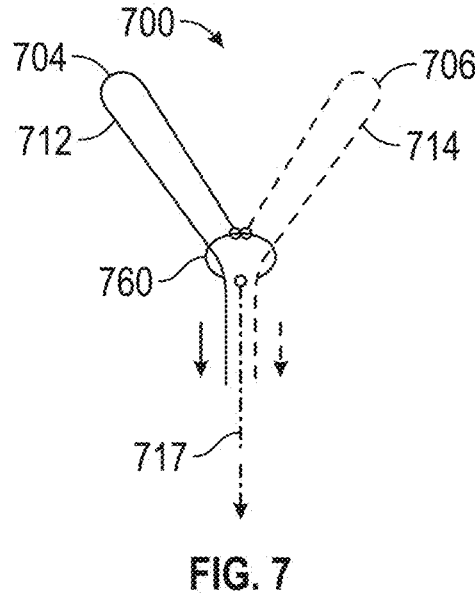
FIG. 7
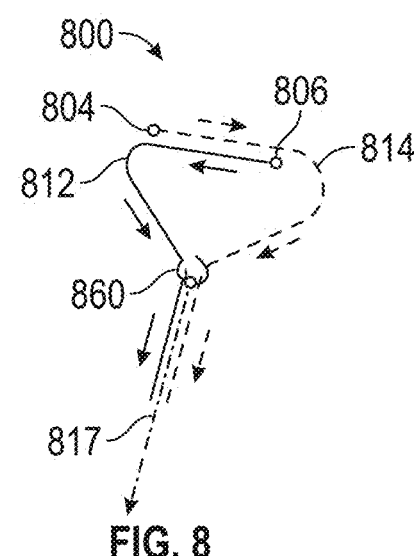
FIG. 8
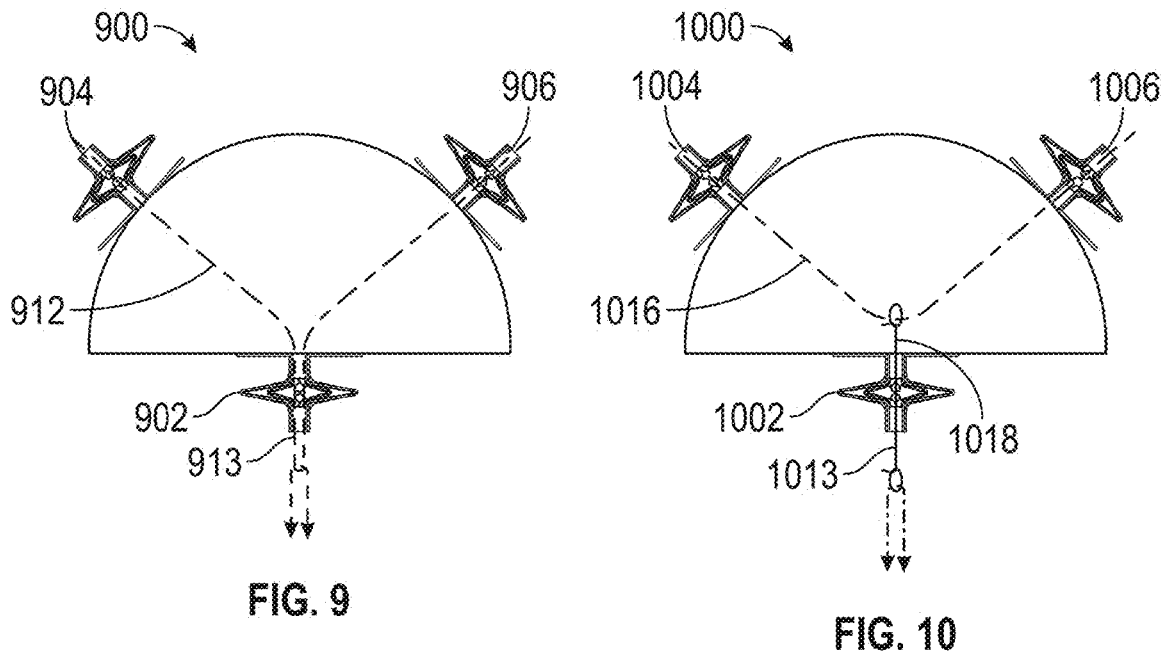
FIG. 9
FIG. 10

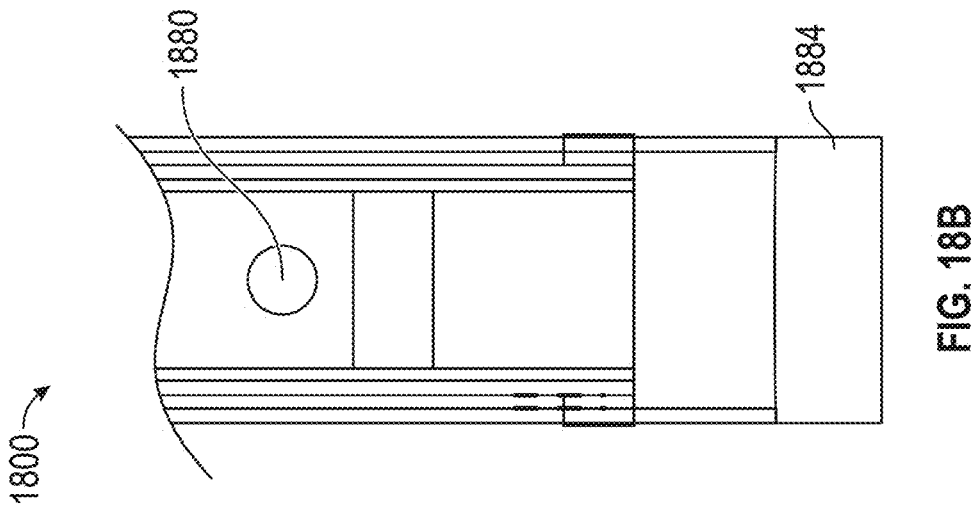
FIG. 18B
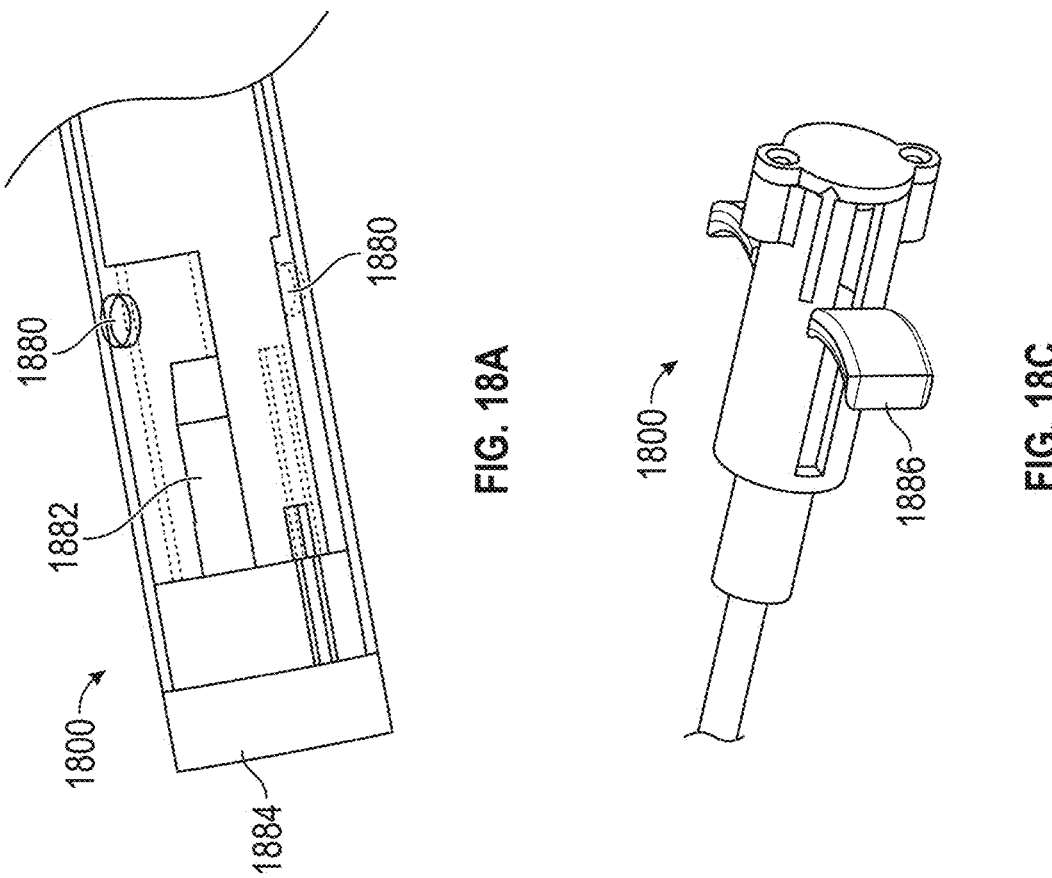
FIG. 18A
FIG. 18C

2304

2484

2304

2382

2484

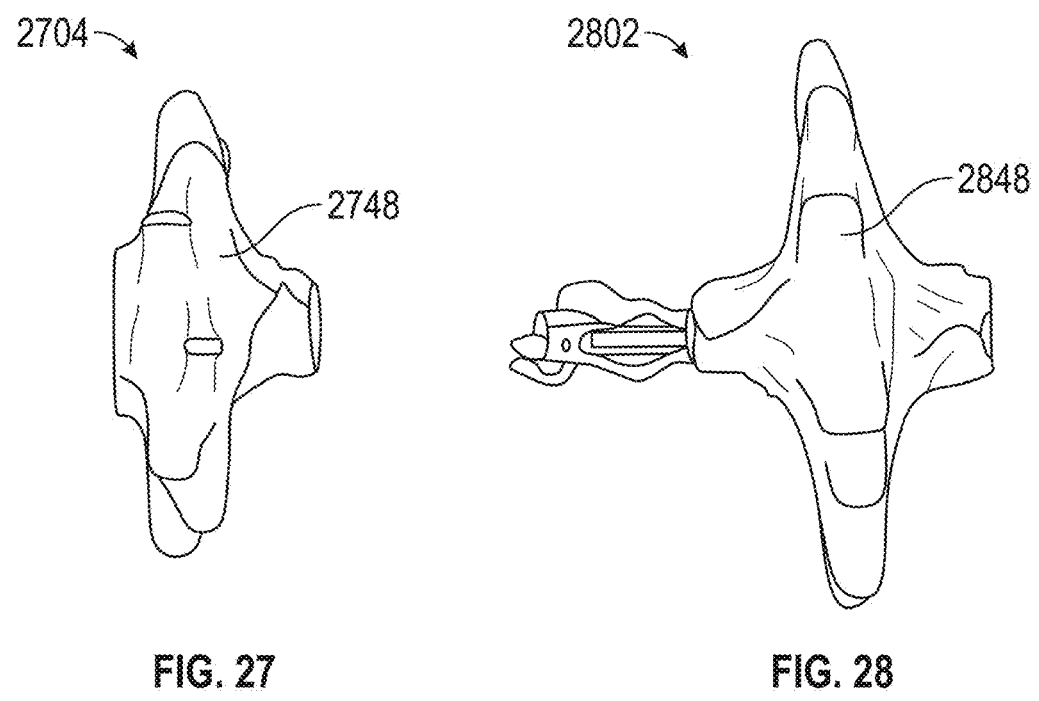
FIG. 27                    FIG. 28
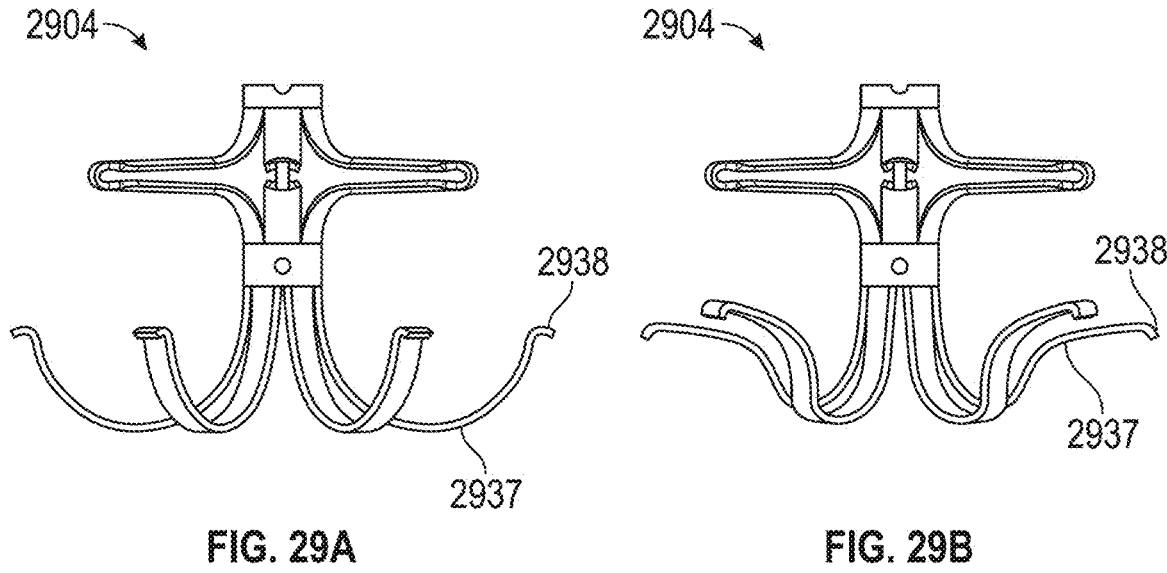
FIG. 29A                   FIG. 29B

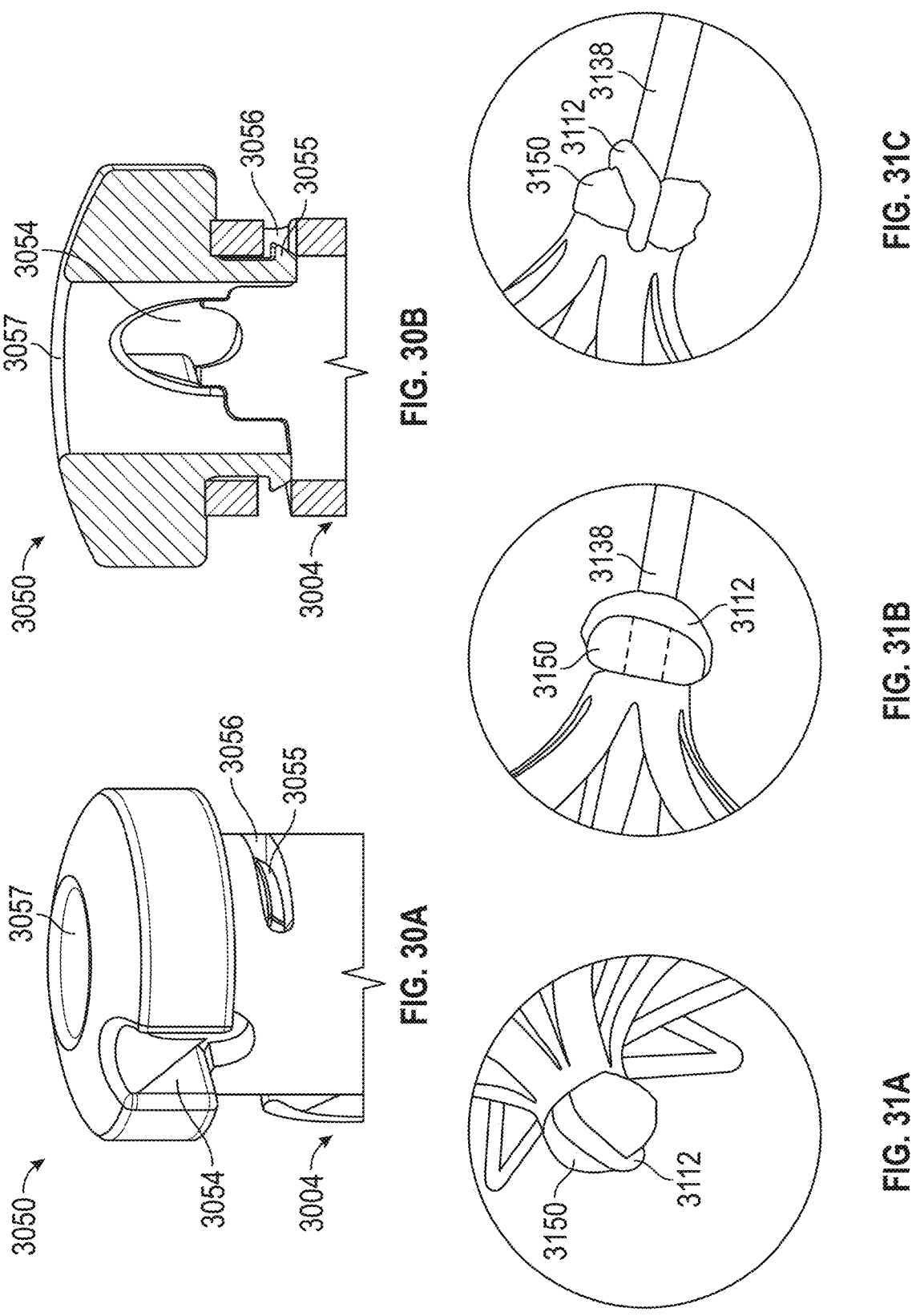

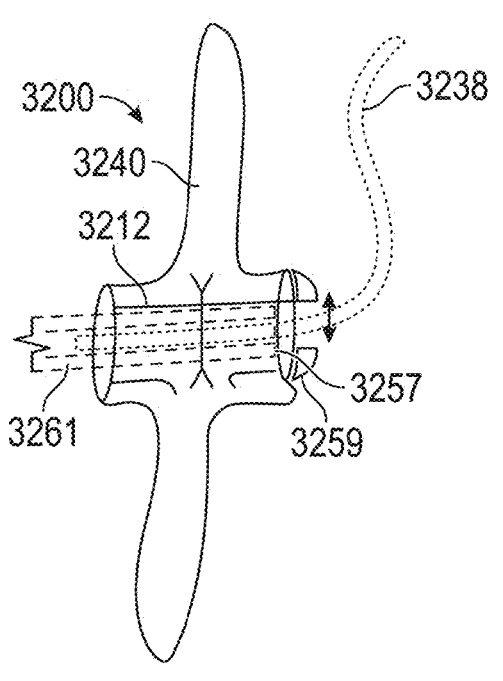
FIG. 32
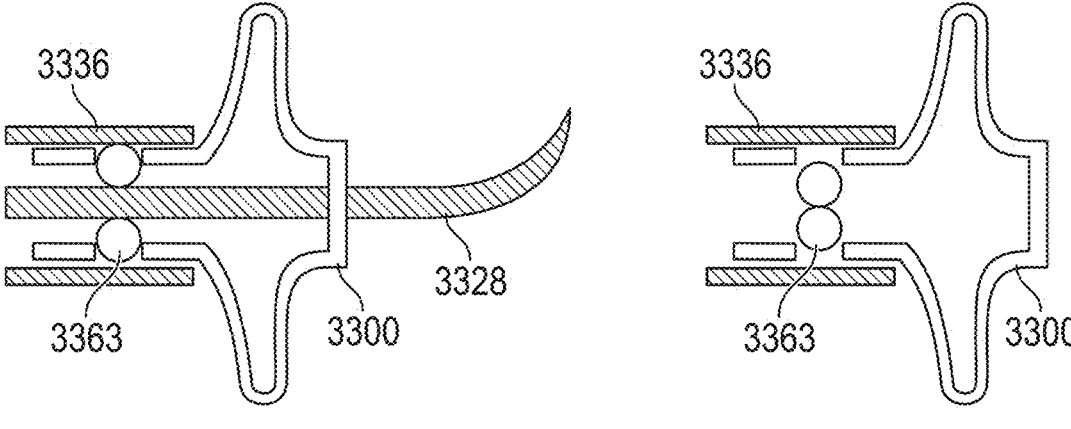
FIG. 33A             FIG. 33B

SYSTEMS FOR PERCUTANEOUS VENTRICULOPLASTY USING VENTRICULAR ANCHORS

INCORPORATION BY REFERENCE TO ANY PRIORITY APPLICATIONS

This application claims the benefit of priority under 35 U.S.C. § 119(e) to U.S. Provisional Patent Application No. 63/573,376, filed Apr. 2, 2024, and U.S. Provisional Patent Application No. 63/691,947, filed Sep. 6, 2024. Both of these applications are hereby incorporated by reference herein in their entireties. Any and all applications for which a foreign or domestic priority claim is identified in the Application Data Sheet as filed with the present application are hereby incorporated by reference under 37 CFR 1.57.

BACKGROUND

Field

Embodiments of this application are directed to systems, methods and devices for treating heart failure patients with dilated ventricles using percutaneous ventriculoplasty.

Description of the Related Art

Heart failure can include myocardial infarction (MI), caused by decreased or complete cessation of blood flow to a portion of the myocardium. MI can cause the left ventricle to dilate or enlarge, known as dilated cardiomyopathy. Ventricular dilation can be treated with ventriculoplasty, or ventricular remodeling.

SUMMARY

In patients with dilated cardiomyopathy, the left ventricle can become enlarged and the walls of the heart can stretch. Thus, the ventricular wall can become thinner and weaker. The left ventricle can experience difficulty contracting and lose its ability to contract. Dilated cardiomyopathy can spread to the right ventricle and to the atria in severe cases.

Ventriculoplasty can include remodeling the left ventricle using a device that maintains the structure of the ventricle. Systems for ventriculoplasty can reduce the size, and volume, of the ventricle using structures in or around the ventricle to reinforce or manipulate the wall. Tension between the ventricular wall and the ventricular septum can be used to reshape the ventricle and prevent further dilation. In other embodiments, tension between multiple implants on one or more ventricular walls can be used to reshape the ventricle and prevent further dilation.

The present disclosure relates to systems and methods for percutaneous ventriculoplasty, or restructuring a ventricle of a patient that has become dilated. The systems and methods described herein are minimally invasive compared to existing ventriculoplasty systems. For example, by introducing the system to the left ventricle from the right ventricle the anchoring system can be introduced fully percutaneously without leaving additional access-related punctures to close (e.g., access via a transatrial septal approach). Though, in other embodiments, a similar delivery system and/or anchoring system may be introduced into the left ventricle without piercing the septum. In some implementations, the individual anchors in the system can be deployed within the heart wall, thus minimizing the exposure of the individual anchors outside the heart wall and in proximity to other tissue structures.

In some implementations, the systems and methods for ventriculoplasty can include introducing the system to the right ventricle fully percutaneously. These systems and methods can be used to prevent or reduce tricuspid regurgitation and/or infections in the right ventricle. The anchors can be introduced entirely from within the right ventricle, minimizing the exposure of the individual anchors outside the heart wall and in proximity to other tissue structures. By positioning the ventricular septal anchor from within the right ventricle, the diameter of the hole needed to be formed in the ventricular septum can be minimized. The hole in the ventricular septum can only need to be large enough to allow the collapsed anchor and delivery catheter to pass through.

The systems and methods described herein can allow individual placement of each anchor in an optimal position. Individual placement of anchors can allow for a customized solution for each patient that optimizes outcomes. The systems and methods described herein can allow individual tensioning of each of the anchors. Individual tensioning of the anchors can allow for additional customization of the therapy and ideal left ventricular shaping in order to maximize left ventricular ejection fraction. Individual tensioning can allow for achieving an ideal or enhanced sphericity index, or the ratio of the ventricle length and width. In some examples, the target sphericity index can be approximately 1.6. In some examples, the target sphericity index can be at least approximately 1 and/or less than approximately 2. Anchors may be placed in the pericardial space and/or outside the pericardial space. The compressible wings of the anchor may be positioned in the pericardial space, for example such that they expand in the pericardial space.

In some implementations, the method can include advancing a catheter into a left ventricle, for example through the ventricular septum, and advancing a first anchor through the catheter into a first ventricular wall location. The first anchor can be tethered to at least one suture. Optionally, after the first anchor is advanced into the first ventricular wall location, the method can include advancing one or more additional anchors into additional ventricular wall locations. For example, the method can include advancing the catheter to a second ventricular wall location and advancing a second anchor through the catheter into the second ventricular wall location. The first ventricular wall location can be between papillary heads and/or the first ventricular wall location can be between a mitral annulus and papillary heads and/or the first ventricular wall location can be in or near the infarct tissue and/or the first ventricular anchor can be between the papillary heads and the left ventricular apex. In some examples, the first ventricular wall location can be between the papillary muscle and the apex of the ventricle. The second anchor can be tethered to at least one suture, for example the at least one suture tethered to the first anchor. The method can include retracting the catheter to a right ventricle and advancing a third anchor through the catheter into the ventricular septum. The third anchor can be tethered to the at least one suture. The method can include tightening the at least one suture to a desired tension. The method can include tightening multiple sutures to multiple degrees of tension. The method can further include removing the catheter.

In some implementations, the method may include anchoring the catheter in at least one of the first ventricular wall location, the second ventricular wall location, or the ventricular septum. The anchoring of the catheter may be temporary. Anchoring the catheter can include exposing an anchoring coil from a distal end of the catheter and advancing the anchoring coil into a myocardial wall of the left ventricle.

In some implementations, the method may include deploying a suture lock configured to trap the at least one suture between opposing layers of the suture lock. The method may include cutting the at least one suture in the right ventricle. The method may include cutting the at least one suture in the left ventricle.

The method may include expanding at least one of the first anchor, the second anchor, or the third anchor by advancing at least one of the first anchor, the second anchor, or the third anchor from the catheter.

In some implementations, the method may include piercing the ventricular septum with a dilator or a guidewire. Piercing the ventricular septum may include puncturing the ventricular septum with RF energy delivered from the dilator.

The method may include advancing a guidewire through at least one of the first ventricular wall location or the second ventricular wall location such that a distal tip of the guidewire is positioned between an epicardium and a pericardium. The distal tip of the guidewire can be positioned in the pericardial space or cavity. The method may include guiding the guidewire using Electrocardiographic Radial Depth Navigation. The method may include guiding an anchoring coil using Electrocardiographic Radial Depth Navigation. The method may include guiding the delivery catheter distal tip using Electrocardiographic Radial Depth Navigation. The method may include advancing the catheter over the guidewire between the epicardium and the pericardium.

In some implementations, the method may include deploying a hemostasis element in the ventricular wall, the hemostasis element configured to prevent blood from passing through the ventricular wall.

In some implementations, the method may include advancing a guide sheath into a right ventricle. The guide sheath may be independently steerable from the septal crossing catheter. In some implementations, the method may include advancing a secondary independent guide sheath into a right ventricle towards the ventricular septum. The secondary guide sheath may be independently steerable from the first guide sheath and from the septal crossing catheter. The method may include advancing the septal crossing catheter through the guide sheath, or sheaths, and into the left ventricle.

One or more sutures may be tethered to at least one anchor of a plurality of anchors and untethered to another one of the plurality of anchors to facilitate independent tensioning. For example, in some implementations, tightening the at least one suture includes tightening a suture tethered to the first anchor and the second anchor, the suture being untethered to the third anchor. In some implementations, tightening the at least one suture includes tightening a suture tethered to the first anchor and the third anchor, the suture being untethered to the second anchor. In some implementations, tightening the at least one suture can include tightening a suture tethered to the second anchor and the third anchor, the suture being untethered to the first anchor.

Certain aspects of the disclosure relate to a system for percutaneous ventriculoplasty. The system can include one or more anchors. For example, the one or more anchors may include a first anchor which can be implanted in a first location in a left ventricular wall, a second anchor which can be implanted in a second location in the left ventricular wall, and/or a third anchor which can be implanted in a ventricular septum. The system can include at least one suture which can be tethered to the first anchor, the second anchor, and/or the third anchor. The anchors and sutures can allow the ventricle to be reduced in size in particular dimensions tailored to the patient.

In some implementations, at least one of the first anchor, the second anchor, or the third anchor is self-expanding. At least one of the first anchor, the second anchor, or the third anchor may include a plurality of wings extending radially outward from a central body. The plurality of wings may include at least one outer wing and at least one inner wing, the outer wing extending radially outward beyond the at least one inner wing. At least one of the first anchor, the second anchor, or the third anchor may be covered in polymeric layer. The plurality of wings can be compressible.

Each suture may be tethered to any number of the anchors and/or another suture. For example, a first suture of the at least one suture may be tethered between the first anchor and the third anchor and/or a second suture of the at least one suture may be tethered between the second anchor and the third anchor. A first suture of the at least one suture may be tethered between the first anchor and the second anchor and/or between the second anchor and the third anchor. A second suture of the at least one suture may be tethered between the second anchor and the first anchor and/or between the first anchor and the third anchor. The at least one suture may include one suture tethered between the first anchor and the third anchor and/or between the third anchor and the second anchor. A first suture of the at least one suture may be tethered between the first anchor and the second anchor, and/or a second suture of the at least one suture may be tethered between the third anchor and the first suture. In some implementations, the at least one suture can include a hemostasis element which can prevent blood from passing through the ventricular wall.

The system may include one or more hemostasis elements. For example, any of the ventricular or septal anchors may include a corresponding hemostasis element. The septal hemostasis element may be different from the ventricular anchor, for example different in size or shape. The septal hemostasis element may be larger than the ventricular anchor.

Certain aspects of the disclosure relate to a system for percutaneous ventriculoplasty including an implant catheter pre-loaded with a plurality of anchors. The plurality of anchors can be tethered with at least one suture. The system can include an anchoring catheter carrying an anchoring coil configured to anchor the anchoring catheter in a ventricular wall.

The system may include a guide sheath for guiding the implant catheter to a ventricular septum. Optionally, the guide sheath is configured to flex in a single direction. The septal crossing catheter may be steerable. The guide sheath may bend up to approximately a 135 degree angle. In some examples, the guide sheath may bend up to approximately a 130 degree angle. The system may include a dilator configured to puncture a ventricular septum with or without RF energy. Optionally, the guide sheath is independently steerable from the other catheters in the delivery system.

In certain implementations, the system can include a septal crossing catheter which can be advanced through a ventricular septum. In some implementations, the system can include a right ventricle sheath for navigating around the right ventricle and positioning the implant catheter and/or the septal crossing catheter in the direction of a ventricular wall. The implant catheter can be advanced through the septal crossing catheter and into the left ventricle. The guide sheath and/or the right ventricle sheath may be used to guide the septal crossing catheter to the ventricular septum. The septal crossing catheter may be steerable, for example the septal crossing catheter may be capable of bending up to a 90 degree angle. The right ventricle sheath may be steerable, for example the septal crossing catheter may be capable of bending up to a 90 degree angle.

Certain methods relating to percutaneous ventriculoplasty can include advancing a catheter into a left ventricle, for example through the ventricular septum, and anchoring the catheter in a ventricular wall, and/or advancing a first anchor through the catheter into the ventricular wall. The first anchor can be tethered to at least one suture. After the first anchor is advanced into the ventricular wall, the method can include retracting the catheter to a right ventricle and advancing a second anchor through the catheter into the ventricular septum. The second anchor can be tethered to the at least one suture. The method can include tightening the at least one suture to a desired tension. The method may further include removing the catheter.

The anchoring of the catheter can be temporary. Anchoring the catheter may include exposing an anchoring coil from a distal end of the catheter and advancing the anchoring coil into a myocardial wall of the left ventricle.

The method may include deploying a suture lock configured to trap the at least one suture between opposing layers of the suture lock. The method may include cutting the at least one suture in the right ventricle.

The method may include expanding at least one of the first anchor or the second anchor by advancing at least one of the first anchor or the second anchor from the catheter.

The method may include piercing the ventricular septum with a dilator or a guidewire. Piercing the ventricular septum may include puncturing the ventricular septum with RF energy delivered from the dilator.

The first anchor may be advanced into the ventricular wall between papillary heads. The first anchor may be advanced into the ventricular wall between a mitral annulus and papillary heads.

The method may include advancing a guidewire into the ventricular wall such that a distal tip of the guidewire is positioned between an epicardium and a pericardium. The method may include guiding the guidewire using Electrocardiographic Radial Depth Navigation. Optionally, the method may include advancing the catheter over the guidewire between the epicardium and the pericardium.

In some implementations, the method may include deploying a hemostasis element in the ventricular wall, the hemostasis element configured to prevent blood from passing through the ventricular wall.

The method may include advancing a guide sheath into the right ventricle. The guide sheath may be independently steerable from the catheter. The method may include advancing the catheter through the guide sheath and into the right ventricle.

Certain methods relating to ventriculoplasty can include providing one or more anchors in a ventricular wall and another anchor in a ventricular septum. For example, the method can include providing a first anchor in a first ventricular wall location, a second anchor in a second ventricular wall location, and/or a third anchor in a ventricular septum. The first anchor, the second anchor, and/or the third anchor can be tethered with at least one suture. The method can include tightening the at least one suture to a desired tension. In some implementations, tightening the at least one suture may include tightening a suture tethered to the first anchor and the second anchor, the suture being untethered to the third anchor. Tightening the at least one suture may include tightening a suture tethered to the first anchor and the third anchor, the suture being untethered to the second anchor. Tightening the at least one suture may include tightening a suture tethered to the second anchor and the third anchor, the suture being untethered to the first anchor.

Certain devices described herein include an anchor for securing in a wall of a heart. The anchor can include a central body including a proximal end and a distal end. The anchor can include at least one inner wing extending radially outward from the central body between the proximal end and the distal end and/or at least one outer wing extending radially outward from the central body between the proximal end and the distal end. The at least one outer wing can extend radially outward beyond the at least one at least one inner wing.

At least one of the proximal end of the anchor or the distal end of the anchor can be tapered. The anchors described herein may include a suture lock configured to trap at least one suture between opposing layers of the suture lock. The at least one inner wing may be a plurality of inner wings circumferentially disposed around the central body. At least one outer wing may be a plurality of outer wings circumferentially disposed around the central body. The at least one inner wing and the at least one outer wing may be self-expanding. The anchors described herein may include polymeric layer covering each of the at least one inner wing and the at least one outer wing.

Certain systems relating to ventriculoplasty described herein can include a first anchor which can be implanted in a first location in a ventricular wall, a second anchor which can be implanted in a second location in the ventricular wall, and/or a third anchor which can be implanted in a ventricular septum. The system can include a routing component, for example a ring, which can be positioned within a ventricle. The ventricle can be a left ventricle or a right ventricle. The system can include a plurality of sutures tethered to the first anchor, the second anchor, and/or the third anchor. The plurality of sutures being tethered to the first anchor, the second anchor, and the third anchor can mean at least one suture of the plurality of sutures is tethered to each anchor. The sutures can be routed through the routing component, for example a ring. The ring can be configured to be positioned in the ventricle. The routing component can allow each suture to be independently tensioned.

In some examples, each anchor of the first anchor, the second anchor, and the third anchor comprises a plurality of compressible wings configured to expand radially outward from a central body. In some examples, at least one of the first anchor, the second anchor, or the third anchor comprises a plurality of arms extending from a proximal end thereof, the plurality of arms configured to engage the ventricular wall to prevent blood from passing through the ventricular wall. In some examples, at least one of the first anchor, the second anchor, or the third anchor is covered in polymeric layer. In some examples, a first suture of the plurality of sutures is tethered between the first anchor and the third anchor and a second suture of the plurality of sutures is tethered between the second anchor and the third anchor. In some examples, a first suture of the plurality of sutures is tethered between the first anchor and the second anchor and between the second anchor and the third anchor, and a second suture of the plurality of sutures is tethered between the second anchor and the first anchor and between the first anchor and the third anchor. In some examples, at least one anchor of the first anchor, the second anchor, or the third anchor comprises a cap on a distal end thereof, the cap comprising a first aperture and a second aperture, wherein a suture of the plurality of sutures is configured to extend outside the at least one anchor through the first aperture, around an outer surface of the cap, and into the at least one anchor through the second aperture. In some examples, the system can include a septal pad at least partially encapsulating the third anchor, the septal pad configured to increase a holding force of the third anchor on the ventricular septum. In some examples, the system can include a suture lock comprising a sheath and an inner body, the suture lock configured to engage at least one suture of the plurality of sutures such that a length of the at least one suture is locked between the sheath and the inner body. The length of the suture engaged by the suture lock can be at least 0.5 mm and/or less than or equal to 1 mm. The length of the suture engaged by the suture lock can be at least 0.1 mm and/or less than or equal to 3 mm. The length of the suture engaged by the suture lock can be at least 0.05 mm and/or less than or equal to 5 mm. The length of the at least one suture of the plurality of sutures can be locked between an inwardly facing surface of the sheath and an outwardly facing surface of the inner body.

The septal pad can encapsulate an anchor that is positioned in the ventricular septum.

In some examples, the system can include a suture lock attached to the third anchor, the suture lock comprising a sheath and an inner body, the sheath comprising a plurality of compressible wing. In some examples, in an expanded state, the suture lock can engage at least one suture of the plurality of sutures such that a length of the at least one suture is locked between the sheath and the inner body. In some examples, the suture lock is self-expanding. In some examples, the compressible wings are spaced radially around the sheath. In some examples, the suture lock can engage each suture of the plurality of sutures in the expanded state. In some examples, the system can include a catheter configured to be advanced into the ventricle percutaneously, the catheter configured to carry the first anchor, the second anchor, the ring, and the plurality of sutures.

In some examples, each anchor can include a plurality of compressible wings configured to expand from radially outward from a central body. The anchor can include a lumen, for example through the central body, which can allow each anchor to be delivered over a guidewire. The lumen can be defined by a nitinol hypotube.

Certain methods relating to percutaneous ventriculoplasty described herein can include advancing a first anchor into a first ventricular wall location, advancing a second anchor into a second ventricular wall location, and/or advancing a third anchor into a ventricular septum. The first anchor, the second anchor, and/or the third anchor can be tethered to sutures. The sutures can be routed through a routing component, for example a ring, in the ventricle. The method can include tensioning, using the routing component, each suture independently. In some examples, the anchors can be delivered through an implant catheter.

In some examples, the implant catheter can be advanced into the ventricle and can deliver the anchors from within the ventricle. In some examples, the anchor can be delivered into a pericardial space. In some examples, the anchors can be released to cause compressible wings to expand. In some examples, the anchors can be released to have a plurality of arms, for example a hemostasis element, expand outward to engage an inner wall of the ventricle. In some examples, the implant catheter can be delivered through a guide sheath and/or a septal crossing catheter. In some examples, the compressible wings can expand in a pericardial space. In some examples, the compressible wings can expand in a ventricular septum. The third anchor can be advanced to the ventricular septum after the first anchor is advanced to the first ventricular wall location of the ventricle and the second anchor is advanced to the second ventricular wall location of the ventricle. The third anchor can be advanced to the ventricular septum before at least one of the first anchor is advanced to the first ventricular wall location of the ventricle or the second anchor is advanced to the second ventricular wall location of the ventricle.

Certain systems relating to percutaneous ventriculoplasty described herein can include a catheter delivery system including a handle. The handle can include one or more actuators for independently controlling one or more catheters of the catheter delivery system. For example, the handle can include a septal crossing catheter flex actuator which can flex the septal crossing catheter, a suture actuator which can tension a suture in the implant catheter, and/or an anchor actuator which can advance an anchor through the implant catheter. In some implementations, the system can include a catheter stand which can stabilize the handle.

The catheter stand can include one or more actuators for independently controlling one or more catheters of the catheter delivery system. For example, the catheter stand actuators may control a different degree of motion compared to the catheter delivery system handle. In one example, the catheter stand actuators can control axial movement of one or more catheters, while the catheter handle can control one rotation and/or bending of one or more catheters.

For example, the catheter stand can include a guide sheath actuator which can advance a guide sheath into a right ventricle, a septal crossing catheter actuator which can advance a septal crossing catheter through the guide sheath, into the right ventricle, and across a ventricular septum into a left ventricle, and/or an implant catheter actuator which can advance an implant catheter through the septal crossing catheter into the left ventricle and to the ventricular wall.

In some implementations, the system may include an anchoring catheter actuator which can advance an anchoring catheter through the septal crossing catheter, into the left ventricle and into the ventricular wall. In some implementations, the system may include a cutting catheter actuator which can advance a cutting catheter through the guide sheath. For example, the cutting catheter may be advanced through the guide sheath after the septal crossing catheter is removed. In some implementations, the cutting catheter can cut a suture in the right ventricle. In some implementations, a guide sheath actuator can advance the guide sheath into a right ventricle. The cutting mechanism within the cutting catheter may be incorporated into other catheters, for example as a part of the catheter locking the suture.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

BRIEF DESCRIPTION OF THE DRAWINGS

Certain features of this disclosure are described below with reference to the drawings. The illustrated implementations are intended to illustrate, but not to limit, the implementations. Various features of the different disclosed implementations can be combined to form further implementations, which are part of this disclosure.

FIGS. 7-10 illustrate examples of suture tensioning arrangements.

FIG. 18A illustrates a distal end of a cutting catheter with the blade advanced.

FIG. 18B illustrates the distal end of the cutting catheter of FIG. 18A with the blade advanced.

FIG. 18C illustrates an example of a proximal end of the cutting catheter of FIG. 18A.

FIG. 27 shows an example of a ventricular anchor covered with a coating.

FIG. 28 shows an example of a ventricular septum anchor covered with a coating.

FIG. 29A shows an example of a ventricular anchor with a hemostasis element.

FIG. 29B shows the example of the ventricular anchor of FIG. 29A with the hemostasis element bent inward.

FIG. 30A shows an example of an anchor cap for routing a suture.

FIG. 30B shows a cross-sectional view of the example of the anchor cap of FIG. 30A.

FIG. 31A shows an example of an anchor cap with a suture routed across the anchor cap 3150.

FIG. 31B shows a side view of the example of the anchor cap with a suture routed across the anchor cap of FIG. 31A with a wire extending from the distal end.

FIG. 31C shows another side view of the example of the anchor cap with a suture routed across the anchor cap of FIG. 31A with a wire extending from the distal end.

FIG. 32 shows an example of a ventricular anchor for delivery over a wire.

FIG. 33A shows an example of an anchor with bearing balls disposed around a guidewire.

FIG. 33B shows the example of an anchor with bearing balls of FIG. 33A with the guidewire removed.

Figure 1A:
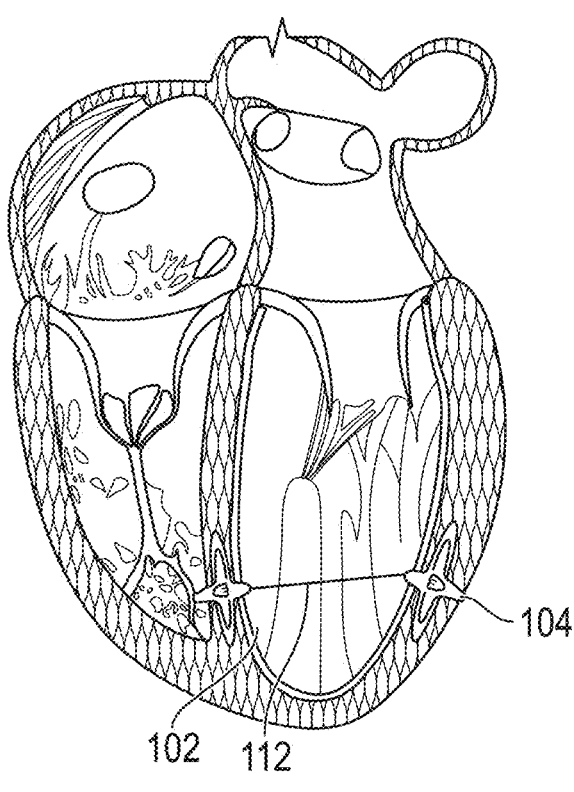
FIG. 1A illustrates an example of a patient's heart with a ventricular septum anchor, a left ventricular wall anchor, and a suture tethered between the ventricular septum anchor and the left ventricular wall anchor.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

DETAILED DESCRIPTION

Various features and advantages of this disclosure will now be described with reference to the accompanying figures. The following description is merely illustrative in nature and is in no way intended to limit the disclosure, its application, or uses. This disclosure extends beyond the specifically disclosed implementations and/or uses and obvious modifications and equivalents thereof. Thus, it is intended that the scope of this disclosure should not be limited by any particular implementations described below. The features of the illustrated implementations can be modified, combined, removed, and/or substituted as will be apparent to those of ordinary skill in the art upon consideration of the principles disclosed herein. Furthermore, implementations disclosed herein can include several novel features, no single one of which is solely responsible for its desirable attributes or which is essential to practicing the systems, devices, and/or methods disclosed herein.

Parts, components, features, and/or elements of the systems and devices described herein that can function the same or similarly across various implementations are identified using similar reference numerals. Differences between the various implementations are discussed herein.

Implementations of the present application relate to percutaneous ventriculoplasty for reducing the size of a dilated left ventricle. Certain embodiments are directed to placing anchors tethered together with suture(s) in the ventricular septum and the ventricular wall and tensioning the sutures to pull the ventricular wall closer to the ventricular septum. In some embodiments, the systems, methods, and devices described herein can be used to reduce the ventricle by at least 15-25% by volume, which can be advantageous for treating dilated cardiomyopathy.

In some embodiments, the systems, methods, and devices described herein include independently tensioning sutures tethered to anchors at different positions in a ventricular wall. This can allow for individually tailored ventriculoplasty in which the ventricle size is reduced by tensioning sutures tethered to anchors at particular wall locations to enhance results for the patient. In some examples, more than one anchor can be delivered into a single position in the ventricular wall.

Figure 1B:
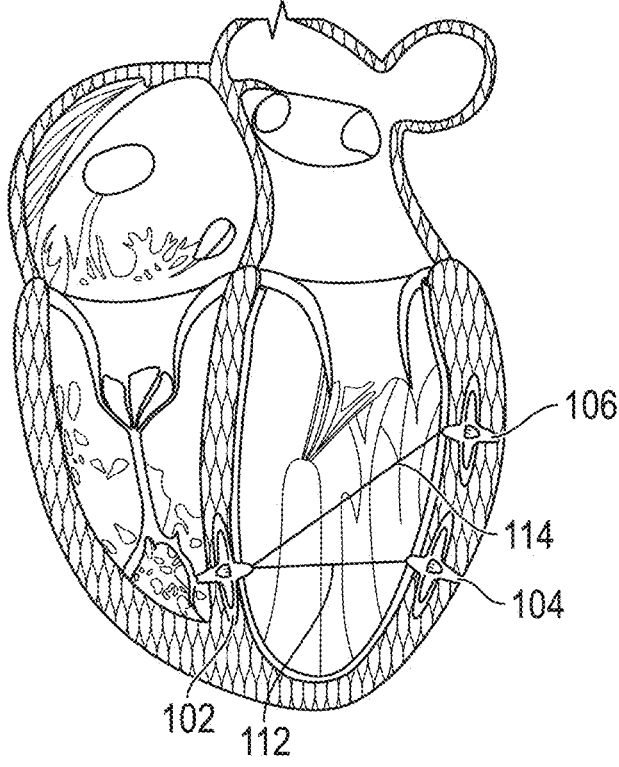
FIG. 1B illustrates another example of a patient's heart with a ventricular septum anchor, two left ventricular wall anchors, and sutures tethered between the ventricular septum anchor and each left ventricular wall anchor.

FIG. 1A illustrates an example of a patient's heart with a ventricular septum anchor 102, a left ventricular wall anchor 104, and a suture 112 tethered between the ventricular septum anchor 102 and the left ventricular wall anchor 104. FIG. 1B illustrates another example of a patient's heart with a ventricular septum anchor 102, two left ventricular wall anchors 104, 106, and sutures 112, 114 tethered between the ventricular septum anchor 102 and each left ventricular wall anchor 104, 106. Any of the anchors described herein can be deployed in the non-limiting configurations illustrated in FIGS. 1A and 1B.

Figure 16A:
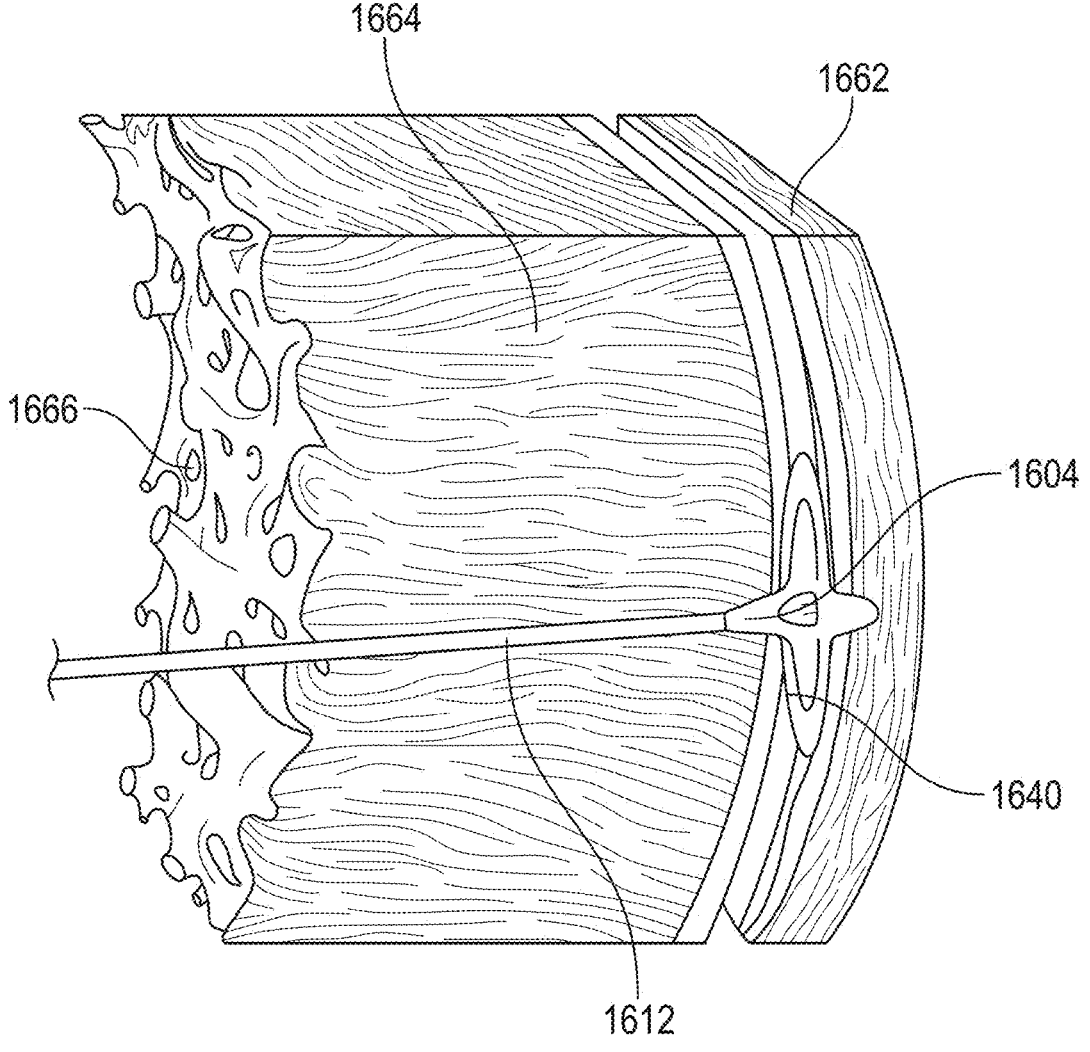
FIG. 16A illustrates an example of an anchor embedded between a pericardium and myocardium.
Figure 16B:
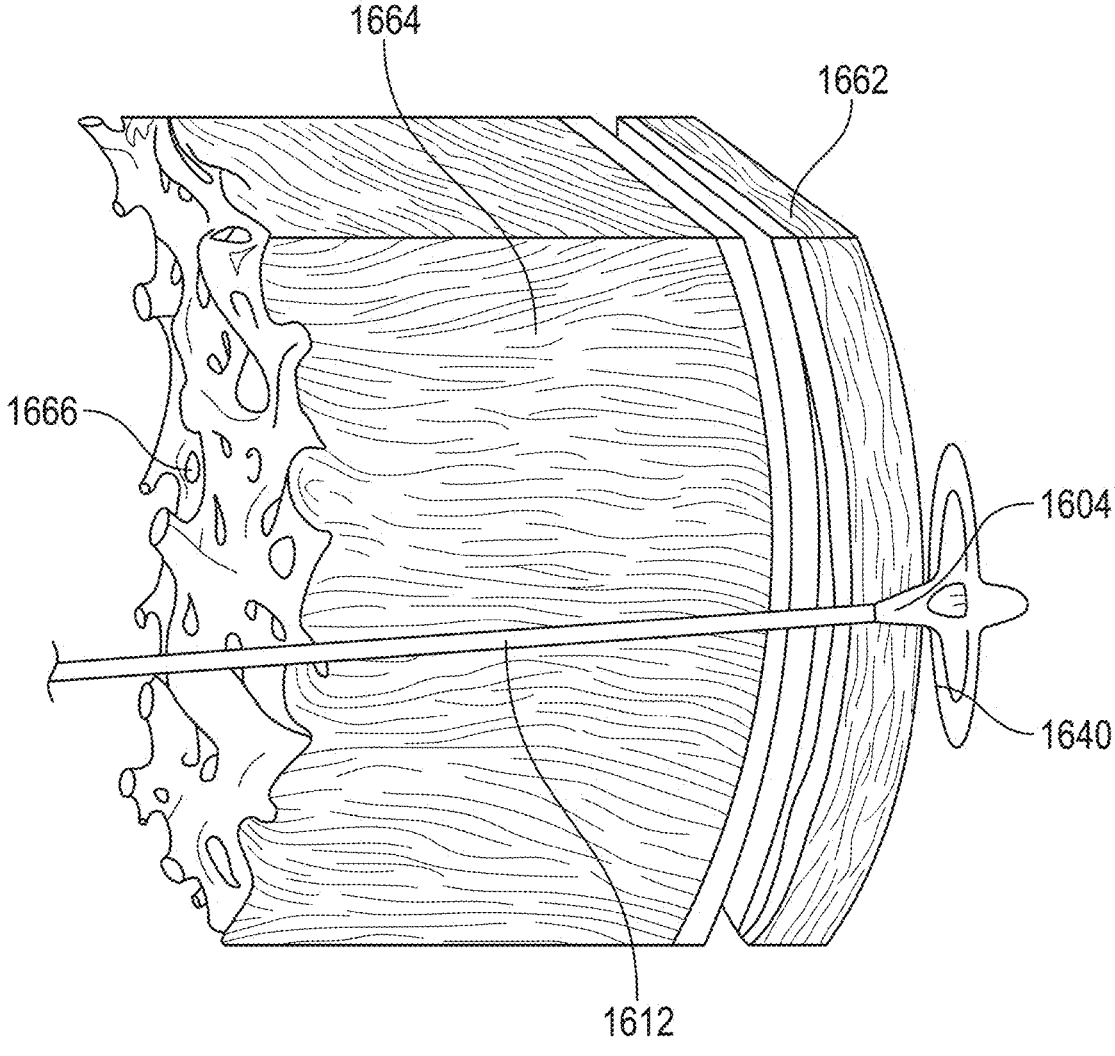
FIG. 16B illustrates an example of an anchor positioned outside a ventricular wall.

As shown in FIG. 1A, the size of the left ventricle can be reduced by tensioning a suture 112 tethered to a ventricular septum anchor 102 and a left ventricular wall anchor 104. The anchors can be positioned in the heart wall such that when the suture is tensioned, the ventricular wall is pulled closer to the ventricular septum. The ventricular wall anchor 104 can be embedded in the heart wall, for example between the myocardium and pericardium, to allow the anchors to remain in place while under tension. When deployed, the ventricular wall anchor 104 is not exposed to the exterior of the heart. Additionally, embedding the ventricular wall anchor 104 between the myocardium and pericardium can avoid damage to the heart wall. Non-limiting examples of placement of the anchors in the heart wall are shown in FIGS. 16A-B. The ventricular wall anchor 104 can be positioned in a particular location along the ventricular wall to reduce dilation in an affected area.

In some embodiments, as shown in FIG. 1B, the system described herein can include multiple ventricular anchors, for example two left ventricular anchors 104, 106. The sutures 112, 114 tethered to the left ventricular anchors 104, 106 can be independently tensioned to reduce the size of the left ventricle in particular dimensions. For example, by tensioning suture 112 to a greater extent than suture 114, the distance between the ventricular septum anchor 102 and the left ventricular anchor 104 can be reduced to a greater extent than the distance between the ventricular septum anchor 102 and the left ventricular anchor 106. Conversely, by tensioning suture 114 to a greater extent than suture 112, the distance between the ventricular septum anchor 102 and the left ventricular anchor 106 can be reduced to a greater extent than the distance between the ventricular septum anchor 102 and the left ventricular anchor 104. A suture routing component in the left ventricle can be used to facilitate independent tensioning of the sutures. As non-limiting examples, the sutures can be routed in an arrangement similar to those described with respect to FIG. 7, 8, 9, or 10. In some examples, more than one ventricular anchor can be delivered into a single position in the ventricular wall. For example, the ventricular anchors can be implanted in the same hole in the ventricular wall to increase the amount of force exerted by tension in that region of the wall.

The first ventricular anchor 104, the second ventricular anchor 106, and/or the third ventricular anchor, or the ventricular septum anchor 102, can be delivered through an implant catheter. The first ventricular anchor 104, the second ventricular anchor 106, and/or the ventricular septum anchor 102 can be preloaded in the implant catheter. The sutures 112, 114 can be delivered by the implant catheter and/or preloaded in the implant catheter. In some examples, the ventriculoplasty system can be preloaded in the implant catheter. Once the anchors and sutures are positioned in the left ventricle or the right ventricle, the sutures can be tensioned to reduce or maintain the size of the ventricle. Once the sutures have been tensioned, the sutures can be locked, for example as described with respect to FIGS. 21A-21C. In some examples, three anchors and two sutures can be preloaded in the implant catheter. In some examples, at least 2 and/or less than or equal to 5 anchors and at least 1 and/or less than or equal to 5 sutures can be preloaded in the implant catheter. In some examples, at least 2 and/or less than or equal to 8 anchors and at least 1 and/or less than or equal to 8 sutures can be preloaded in the implant catheter.

In some examples, the ventricular anchors 104, 106, the ventricular septum anchor 102, and/or the sutures 112, 114 can be positioned in the heart using a surgical method, for example an open surgical method.

The anchors, for example the ventricular anchors 104, 106 and/or the ventricular septum anchor 102, can include a central body, a lumen, and elements with apexes extending radially outward from the central body. For example, the anchors can include wings that extend from the central body such that they can be compressed within the implant catheter. Once released, the compressible wings can expand radially outward from the central body. The lumen of the central body can allow the anchors to be delivered over a guidewire. The elements with apexes of the anchors can secure the anchors to the ventricular wall, for example from within the pericardium once expanded. In some examples, the anchors can have expandable elements that provide force against the ventricular wall after being delivered.

The first ventricular anchor 104 can be positioned at a first ventricular wall location and the second ventricular anchor 106 can be positioned at a second ventricular wall location. In some embodiments, the first ventricular wall location or second ventricular wall location can be between papillary heads. For example, the first ventricular wall location or second ventricular wall location can be horizontally between papillary heads. In some examples, the ventricular anchors can be positioned between the papillary heads and the ventricular apex. For example, the first ventricular wall location and/or the second ventricular wall location can be in the lower half of the ventricle. In some embodiments, the first ventricular wall location or second ventricular wall location can be between a mitral annulus and papillary heads. For example, the first ventricular wall location or second ventricular wall location can be above the papillary heads and below the mitral annulus. In some implementations, pulling near papillary muscles can treat or resolve mitral regurgitation.

Figures 1C, 1D:
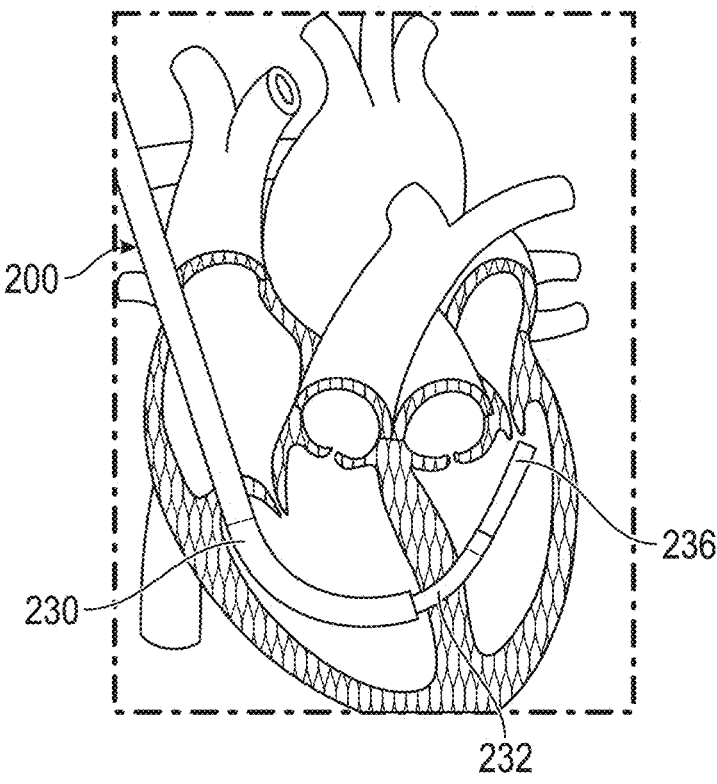
FIG. 1C illustrates an example of a catheter system accessing a patient's heart via the internal jugular vein.
FIG. 1D illustrates a cross-sectional view of the catheter system of FIG. 1C.
Figure 1E:
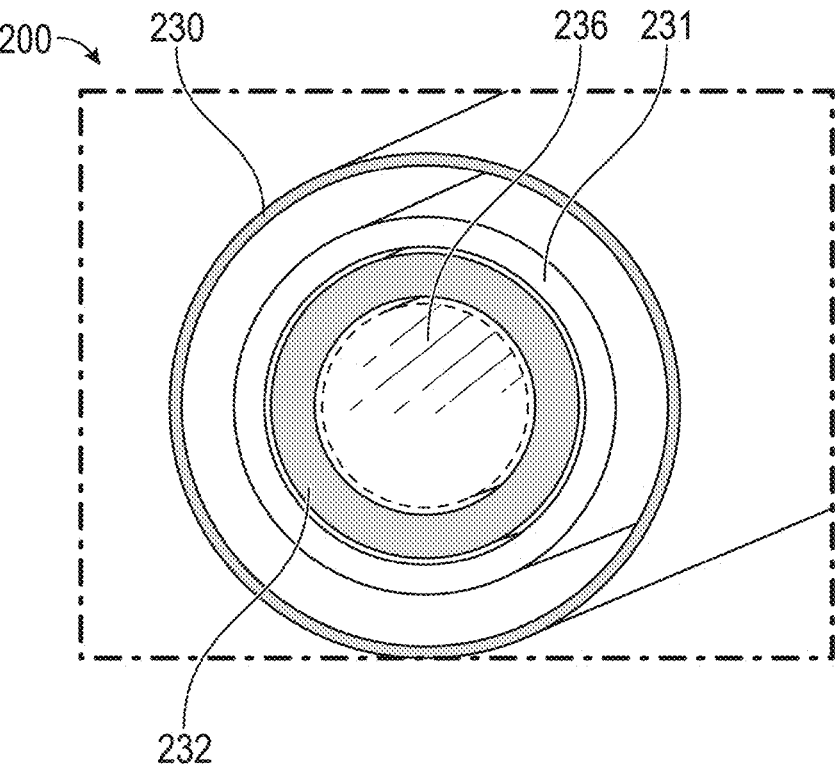
FIG. 1E illustrates a cross-sectional view of another example of a catheter system.
Figure 1F:
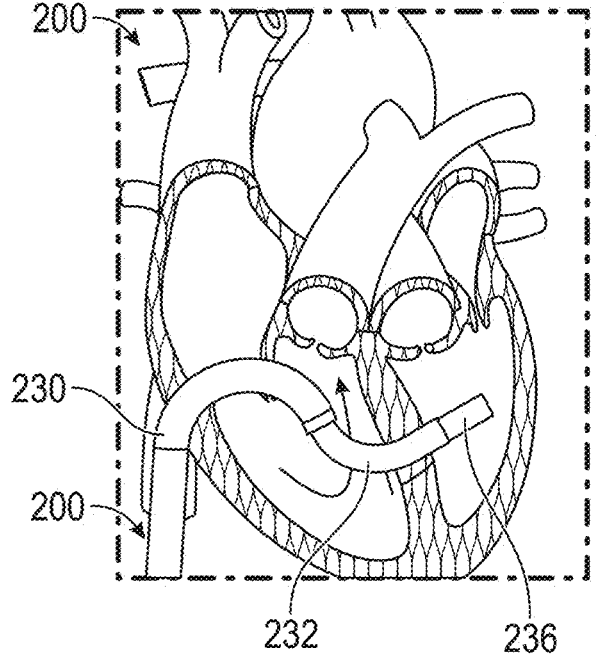
FIG. 1F illustrates an example of a catheter system accessing a patient's heart via the femoral vein.

FIG. 1C illustrates an example of a catheter system 200 accessing a patient's heart via the internal jugular vein. FIG. 1D illustrates a cross-sectional view of the catheter system 200 of FIG. 1C. FIG. 1E illustrates a cross-sectional view of another example of a catheter system. FIG. 1F illustrates an example of a catheter system accessing a patient's heart via the femoral vein The catheter system 200 can be used to perform percutaneous ventriculoplasty.

The catheter system 200 can include one or more catheters. For example, the catheter system 200 can include a guide sheath 230 and/or an implant catheter 236. In some implementations, the catheter system 200 can include a septal crossing catheter 232 when approaching the left ventricle from the right side. In other implementations, the catheter system 200 can enter the left ventricle from the left atrium through the mitral valve. One or more catheters of the catheter system 200 can be delivered over a guidewire 238. Optionally, the catheter system 200 may further include an anchoring catheter 234.

As shown in FIG. 1C, the guide sheath 230 can be introduced percutaneously and advanced from the internal jugular vein to the right atrium, and then to the right ventricle. As shown in FIG. 1F, the guide sheath 230 can be introduced percutaneously and advanced from the femoral vein or femoral artery to the right atrium, and then to the right ventricle. The guide sheath 230 can be independently steerable from any of the other catheters, for example the septal crossing catheter 232. The guide sheath 230 can be set in place to ensure a stable position and septal crossing point. The septal crossing catheter 232 and/or the implant catheter 236 can independently advance through the guide sheath 230 without disrupting the septal puncture or losing the septal crossing position. Advantageously, this can allow the catheters to steer and navigate in the ventricles through the guide sheath 230 without disrupting the ventricular puncture. For example, the implant catheter 236 can steer and navigate in the ventricles through the septal crossing catheter 232 and/or guide sheath 230 without disrupting the ventricular puncture. In some embodiments, the guide sheath 230 may be actively steered using, for example, a pullwire. In other embodiments, the guide sheath 230 may be pre-bent. For example, the guide sheath 230 may be designed to assume a particular configuration upon removal of an inner body. The guide sheath 230 can bend up to approximately 90 degrees or, in some cases, greater than 90 degrees. For example, the guide sheath 230 can bend up to approximately 135 degrees. The guide sheath 230 can be designed to flex in a single direction or in a multiple directions.

In some examples, the catheter system 200, the guide sheath 230, the septal crossing catheter 232, and/or the implant catheter 236 can be robotically guided. In some examples, the catheter system 200, the guide sheath 230, the septal crossing catheter 232, and/or the implant catheter 236 can be remotely guided. In some examples, the catheter system 200, the guide sheath 230, the septal crossing catheter 232, and/or the implant catheter 236 can be controlled by an algorithm, an artificial intelligence, and/or a machine learning algorithm. In some examples, a robotic system can be used to control at least one or all of the catheters of the catheter system 200. For example, a robotic system can be used to position the anchors and/or the sutures in the heart. In some examples, a catheter can be actuated by a robotic control system and/or have functions that are automatically or semi-automatically controlled. For example, in certain embodiments, longitudinal movement and/or rotation of the catheter can be controlled by a robot with linear and/or rotational actuators. Bending and expansion at the distal end of the catheter can also be controlled by a robotic system. In one example embodiment, movement and motion of the catheter can be automatically controlled by the robot system to gather data as described above along radial and longitudinal divisions of the artery. Once information is gathered, the robot system can automatically or semi-automatically move the neuromodulation element to the designated or targeted regions so as to perform ablation as described herein.

The septal crossing catheter 232 can be advanced, for example through the guide sheath, through the ventricular septum into the left ventricle. The septal crossing catheter 232 can pierce the ventricular septum with a dilator or a guidewire. In some embodiments, the dilator can deliver RF energy to pierce the ventricular septum. The septal crossing catheter 232 can be independently steerable from the guide sheath 230. Advantageously, this can allow the septal crossing catheter 232 to steer and navigate in the ventricles without disrupting the ventricular puncture. In some embodiments, the septal crossing catheter 232 is actively steerable. In other embodiments, the septal crossing catheter 232 may simply follow the bent configuration of the guide sheath 230. The septal crossing catheter 232 can bend up to approximately 90 degrees or, in some cases, greater than 90 degrees. For example, the septal crossing catheter 232 can bend up to approximately 135 degrees.

In some embodiments, the catheter system 200 may include an anchoring catheter 234 that can be advanced through the guide sheath 230 and/or the septal crossing catheter 232. The anchoring catheter 234 can anchor the implant catheter 236 to the ventricular wall, for example using an anchoring coil, barb or other anchoring structure on the distal end. The anchoring coil can be advanced into a myocardial wall of the left ventricle to anchor the implant catheter 236 to the wall. The implant catheter 236 can temporarily anchor to the ventricular wall. The anchoring catheter 234 can retract after an anchor is placed in the ventricular wall. In some embodiments, the system does not include a separate anchoring catheter 234. Rather, the implant catheter 236 or anchoring system can include an anchoring structure, for example an anchoring coil on the distal end. The anchoring catheter 234 or implant catheter 236 can be guided using Electrocardiographic Radial Depth Navigation (EDEN) to navigate the anchoring structure at least partially across the myocardial wall. In some examples, the anchoring catheter 234 or implant catheter 236 can be guided using bubble mapping. In some examples, the anchoring catheter 234 or implant catheter 236 can be guided using carbon dioxide mapping or insufflation. The anchoring catheter 234 can be jacketed and only the tip exposed to electrically isolate the anchoring coil for enhancing EDEN navigation.

The implant catheter 236 can be advanced, for example through the guide sheath 230, the anchoring catheter 234, and/or the septal crossing catheter 232, to a location on the ventricular wall. The implant catheter 236 can deliver one or more anchors into the ventricular wall. The anchors can be advanced through the interior of the implant catheter 236. The anchors can be pre-loaded in the implant catheter 236, for example with the sutures already tethered to the anchors.

The implant catheter 236 can deliver one or more anchors between papillary heads on the ventricular wall. The implant catheter 236 can deliver the anchors between the mitral annulus and papillary heads on the ventricular wall. The implant catheter 236 can deliver the anchors below the papillary heads, for example directly into an infarct. A distal tip of the implant catheter 236 can be positioned between the epicardium and the pericardium. In some implementations, the distal end of implant catheter 236 can be positioned in the myocardium. The distal end of the catheter can partially pierce the ventricular wall in order to position the anchors within the ventricular wall. Non-limiting examples of positions of the anchors within the ventricular wall are shown in FIGS. 16A-B. The implant catheter 236 can deploy a hemostasis element in the central lumen of the anchor.

In some implementations, the implant catheter 236 can have multiple lumens. In some implementations, the implant catheter 236 can carry the one or more anchors in a different lumen than the one or more sutures. Advantageously, this can prevent the sutures from becoming embedded in the ventricular wall. In some implementations, the lumen of the implant catheter 236 can include a slit for managing the one or more sutures. Advantageously, the implant catheter 236 having a separate lumen or slit for the suture may allow the anchor to remain crimped in the implant lumen without causing tangling with the suture. The suture lumen or slit may be partially connected to the implant lumen such that the sutures can remain tethered to the implants during insertion.

Optionally, a guidewire 238 can be advanced to the ventricular wall to guide the implant catheter 236. One or more guidewires 238 may be advanced to guide at least one of the guide sheath 230, septal crossing catheter 232, anchoring catheter 234, and implant catheter 236. The one or more guidewires 238 can be inserted before at least one of the guide sheath 230, septal crossing catheter 232, anchoring catheter 234, or implant catheter 236. A distal tip of a guidewire 238 can be positioned between the myocardium and the pericardium, for example to guide the implant catheter 236 into the ventricular wall. The one or more guidewires 238 can navigate using Electrocardiographic Radial Depth Navigation (EDEN). In some examples, the one or more guidewires 238 can be guided using bubble mapping. In some examples, the one or more guidewires 238 can be guided using carbon dioxide mapping or insufflation.

As shown in FIG. 1E, the catheter system 200 can include a right ventricle sheath 231. The right ventricle sheath 231 may be positioned radially within the guide sheath 230 and/or radially outside the septal crossing catheter 232. The right ventricle sheath 231 can rotate within the right ventricle after the guide sheath 230, or an introducer sheath, is used to enter the right ventricle. The right ventricle sheath 231 can be used to navigate such that the implant catheter 236 is positioned toward a particular location for placing the implant in the ventricular wall. The right ventricle sheath 231 can be used to navigate such that the septal crossing catheter 232 is positioned toward a particular location for piercing the ventricular septum.

Figure 2A:
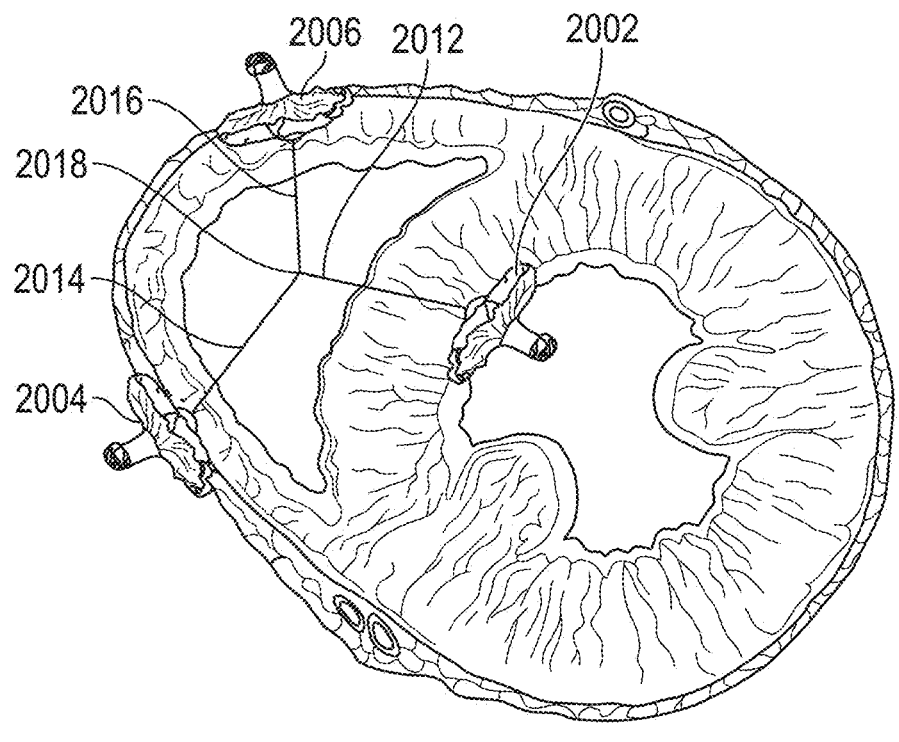
FIG. 2A shows an example of a patient's heart with anchors, sutures, and a suture routing component in the right ventricle.

FIG. 2A shows an example of a patient's heart with a ventricular septum anchor 2002, a first right ventricular wall anchor 2004, a second right ventricular wall anchor 2006, and sutures 2012, 2014, 2016 tethered between the ventricular septum anchor 2002, the right ventricular wall anchors 2004, 2006, and a suture routing component 2018. Fewer or greater number of anchors may be used. For example, there may be only the ventricular septum anchor 2002 and one of the ventricular wall anchors.

Right ventriculoplasty may be performed to treat tricuspid regurgitation or an infection in the right ventricle. The ventricular septum may not need to be pierced with a hole large enough to allow the catheter to cross the septum. The hole in the ventricular septum can only need to be large enough to allow the ventricular septum anchor 2002 to cross the septum in the compressed state. Therefore, the ventricular septum anchor 2002 may be smaller for the right ventriculoplasty compared to left ventriculoplasty. The ventricular septum anchor 2002 only needs to be able to block flow through the smaller hole formed in the septum to allow the placement of the ventricular septum anchor 2002. In some examples, the ventricular septum anchor 2002 may have a diameter of 10 mm when expanded. The ventricular septum anchor 2002 may have a diameter of greater than about 5 mm and/or less than about 15 mm when expanded. The ventricular septum anchor 2002 may have a diameter of greater than about 2 mm and/or less than about 20 mm when expanded.

As shown in FIG. 2A, the size of the right ventricle can be reduced by tensioning a suture 2012, 2014, 2016 tethered to a ventricular septum anchor 2002 and/or the right ventricular wall anchors 2004, 2006. The anchors can be positioned in the heart wall such that when the suture is tensioned, the ventricular wall is pulled closer to the ventricular septum. One or more ventricular wall anchors 2004, 2006 can be embedded in the heart wall, for example between the myocardium and pericardium, to allow the anchors to remain in place while under tension. In some examples, when deployed, the ventricular wall anchor 2004 is not exposed to the exterior of the heart. Additionally, embedding the ventricular wall anchor 2004, 2006 between the myocardium and pericardium can avoid damage to the heart wall. Non-limiting examples of placement of the anchors in the heart wall are shown in FIGS. 16A-16B. The ventricular wall anchors 2004, 2006 can be positioned in a particular location along the ventricular wall to reduce dilation in an affected area.

In some examples, the suture 2012 tethered to the ventricular septum anchor 2002 can be independently tensioned to reduce the size of the right ventricle in particular dimensions. The suture 2014 tethered to the right ventricular anchor 2004 can be independently tensioned to reduce the size of the right ventricle in particular dimensions. The suture 2016 tethered to the right ventricular anchor 2006 can be independently tensioned to reduce the size of the right ventricle in particular dimensions. For example, by tensioning suture 2014 to a greater extent than sutures 2012, 2016, the distance between the routing component 2018 and the right ventricular anchor 2004 can be reduced to a greater extent than the distance between the routing component 2018 and the ventricular septum anchor 2002 and/or the right ventricular anchor 2006. The suture routing component 2018 in the right ventricle can be used to facilitate independent tensioning of the sutures. As non-limiting examples, the sutures can be routed in an arrangement similar to those described with respect to FIG. 7, 8, 9, or 10. As a non-limiting example, the sutures can be routed using a suture routing handle similar to the handle described with respect to FIGS. 25A-25C.

The first ventricular wall anchor 2004 can be positioned at a first ventricular wall location and the second ventricular wall anchor 2006 can be positioned at a second ventricular wall location. In some embodiments, the first ventricular wall location or second ventricular wall location can be between papillary heads. For example, the first ventricular wall location or second ventricular wall location can be horizontally between papillary heads. In some embodiments, the first ventricular wall location or second ventricular wall location can be between a mitral annulus and papillary heads. For example, the first ventricular wall location or second ventricular wall location can be above the papillary heads and below the mitral annulus. In some implementations, pulling near papillary muscles can treat or resolve mitral regurgitation.

The ventricular septum anchor 2002, the first ventricular wall anchor 2004, and/or the third ventricular wall anchor 2006 can include hemostasis components to prevent blood from passing through the ventricular wall or septum. In some examples, the hemostasis elements can be attached to the anchors. In some examples, the hemostasis elements can be attached to the sutures. The ventricular wall anchors 2004, 2006 can be positioned anywhere on the lateral left ventricular wall. The ventricular septum anchor 2002 can be anchored in the intra-ventricular septum.

Figure 2B:
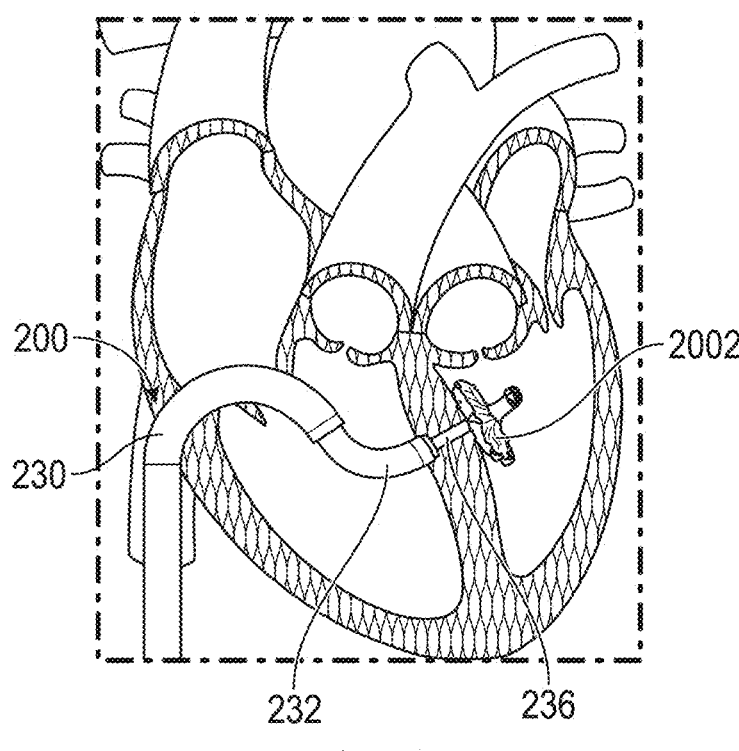
FIG. 2B-2D illustrate an example of a catheter system positioning anchors in a right ventricle of a patient's heart.
Figure 2C:
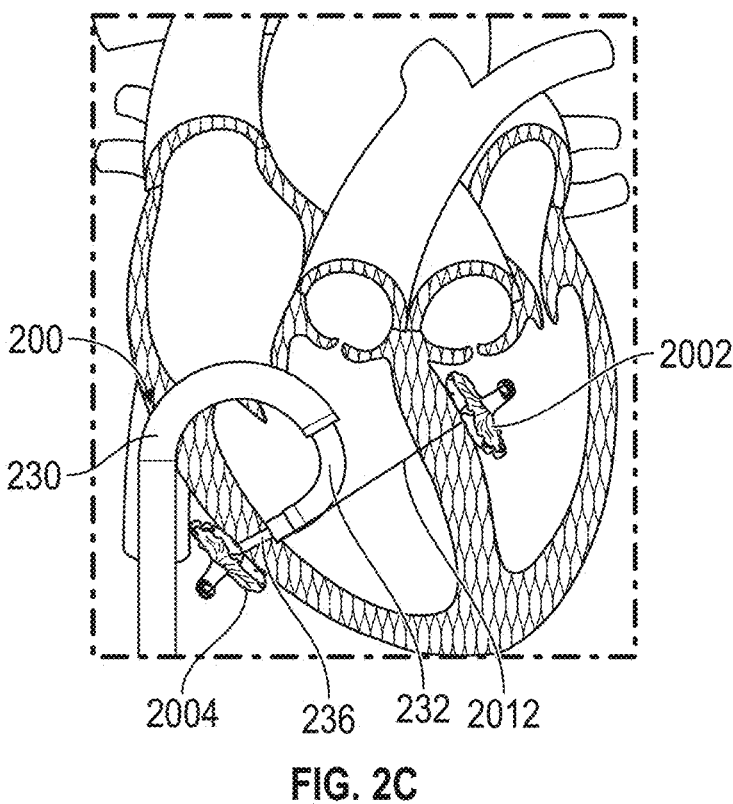
Figure 2D:
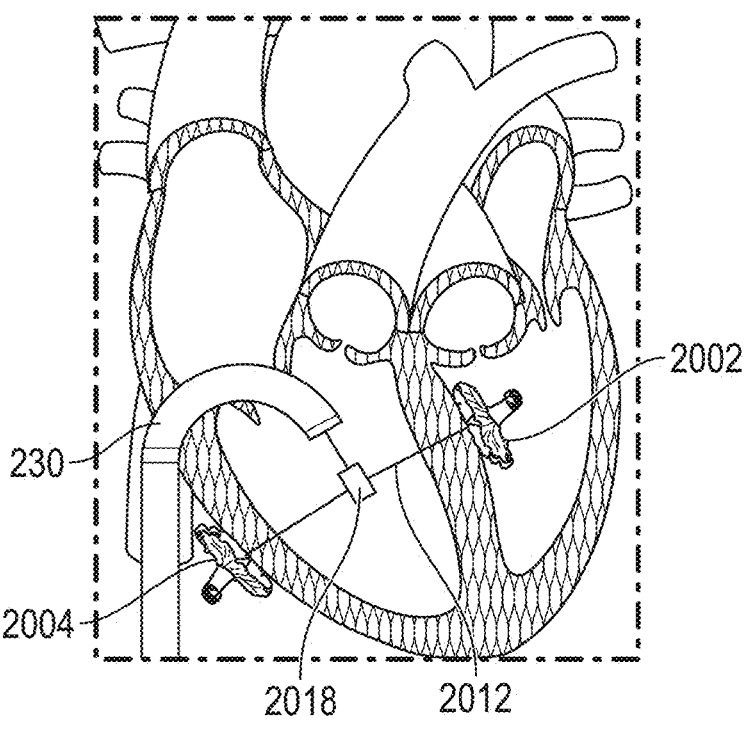

FIG. 2B-2D illustrate an example of a catheter system 200 positioning anchors in a right ventricle of a patient's heart.

The catheter system 200 can include one or more catheters. For example, the catheter system 200 can include a guide sheath 230 and/or an implant catheter 236. In some implementations, the catheter system 200 can include a septal crossing catheter 232. The septal crossing catheter 232 may act as a positioning catheter or secondary catheter for contacting a heart wall or septum. One or more catheters of the catheter system 200 can be delivered over a guidewire 238.

In some examples, the guide sheath 230 can be introduced percutaneously and advanced from the femoral vein or femoral artery to the right atrium. In some examples, the guide sheath 230 can be introduced percutaneously and advanced from the internal jugular vein to the right atrium. In some examples, the guide sheath 230 may be advanced by another venous approach. The guide sheath 230 can be introduced through a femoral vein or femoral artery. The guide sheath 230 can be guided through the external iliac vein and common iliac vein to the inferior vena cava. The guide sheath 230 can be guided through the inferior vena cava to the right atrium. The guide sheath 230 can be independently steerable from any of the other catheters, for example the septal crossing catheter 232. The septal crossing catheter 232 and/or the implant catheter 236 can independently advance through the guide sheath 230. The guide sheath 230 may be angled up to approximately 120 degrees for right ventriculoplasty. In some examples, the guide sheath 230 may be angled up to between approximately 90 degrees and approximately 150 degrees for right ventriculoplasty.

The implant catheter 236 can be advanced, for example through the guide sheath 230 and/or the septal crossing catheter 232 to a location on the ventricular wall. The implant catheter 236 can deliver one or more anchors into the ventricular wall. The anchors can be advanced through the interior of the implant catheter 236. The anchors can be pre-loaded in the implant catheter 236, for example with the sutures already tethered to the anchors. In some examples, the implant catheter 236 can be delivered through the femoral vein or femoral artery, the internal jugular vein, or the radial artery.

The implant catheter 236 can deliver one or more anchors between papillary heads on the ventricular wall. The implant catheter 236 can deliver the anchors between the mitral annulus and papillary heads on the ventricular wall. The implant catheter 236 can deliver the anchors below the papillary heads, for example directly into an infarct. A distal tip of the implant catheter 236 can be positioned between the epicardium and the pericardium. In some implementations, the distal end of implant catheter 236 can be positioned in the myocardium. The distal end of the catheter can partially pierce the ventricular wall in order to position the anchors within the ventricular wall. Non-limiting examples of positions of the anchors within the ventricular wall are shown in FIGS. 16A-B. The implant catheter 236 can deploy a hemostasis element in the central lumen of the anchor.

In some implementations, the implant catheter 236 can have multiple lumens. In some implementations, the implant catheter 236 can carry the one or more anchors in a different lumen than the one or more sutures. Advantageously, this can prevent the sutures from becoming embedded in the ventricular wall. In some implementations, the lumen of the implant catheter 236 can include a slit for managing the one or more sutures.

As shown in FIG. 2B, the catheter system 200 can be used to position a ventricular septum anchor 2002 in the patient's ventricular septum. The guide sheath 230 can be positioned in the right ventricle. The septal crossing catheter 232, or positioning catheter, can contact the ventricular septum. The implant catheter 236 can extend through the ventricular septum from the right ventricle to the left ventricle. The ventricular septum anchor 2002 can be pushed through the implant catheter 236 into the left ventricle. The ventricular septum anchor 2002 can be placed from within the right ventricle.

As shown in FIG. 2C, the septal crossing catheter 232, or positioning catheter, can move and/or rotate such that it contacts a right ventricular wall. The suture 2012 tethered to the ventricular septum anchor 2002 can extend into the implant catheter 236 where it is routed through a suture routing component. The ventricular wall anchor 2004 can be pushed through the implant catheter 236 into the right ventricular wall from within the right ventricle.

As shown in FIG. 2D, the septal crossing catheter 232 and/or the implant catheter 236 can retract into the guide sheath 230. The sutures 2012, 2014 can be routed through the suture routing component 2018. The sutures 2012, 2014 can extend from the suture routing component 2018 into the implant catheter 236. The sutures 2012, 2014 can be independently tensioned. In some examples, as shown in FIG. 2A, a second ventricular wall anchor can be implanted before the suture routing component 2018 is released. The anchors can be positioned distal to the suture routing component 2018, with each anchor being tethered by one or more sutures to the suture routing component 2018.

The systems described herein can be a multi-point, adjustable system. Independently tensioning sutures can adjust the ventricle size in different dimensions based on the locations of the anchors. The anchor specific placement and tensioning mechanism can restore the left or right ventricle to its natural shape acutely. Advantageously, this can impart long-term chronic remodeling effects. Independently tensioning the anchors can achieve an increase in ejection fraction.

The anchors can be placed based on an algorithm. The tension applied to each suture can also be applied based on the algorithm. The algorithm can optimize the placement of the anchors and/or amount of tension applied to each suture based on at least one of free wall strain, global longitudinal strain, radial strain, circumferential strain, ventricular sphericity index, ventricular volume reduction, or force on each anchor. The magnitude of tension applied can also be optimized to reduce the anterior to posterior dimension of the mitral annulus in functional mitral regurgitation patients. These parameters can be measured or determined based on sensors in the left ventricle, right ventricle, catheter system 200, suture routing component 2018, the ventricular septum anchor 2002, and/or the ventricular wall anchors 2004, 2006. In some examples, the sensors can be a pressure sensor, a force sensor, a strain gauge sensor, a piezoelectric sensor, and/or another sensor able to measure a parameter of the ventricle. In some examples, the parameters can be determined by imaging the heart of the patient, for example with echocardiography, cardiac magnetic resonance imaging, coherence tomography imaging, or ultrasound imaging.

A controller can receive the measurements from the one or more sensors and/or the results of the imaging. The algorithm can produce an output based on the measurements of the sensors and/or the results of the imaging. The controller can control the catheter system 200 to position anchor based on the output of the algorithm or direct the clinician to take corrective action. The controller can control the suture tensioning mechanism to tension the sutures based on the output of the algorithm. In some examples, the controller can be implanted subcutaneously or can be external to the patient. The controller may display the output to a user on a display of a user device. A user can position the anchors and/or tension the sutures based on the output of the algorithm.

The suture routing component 2018 can be a tippet ring. The suture routing component 2018 can be used for right or left ventriculoplasty to allow the sutures to be independently tensioned. Each suture can be tied to or routed through the suture routing component 2018. The suture routing component 2018 may be loaded in the implant catheter 236. The suture routing component 2018 can be loaded between the most proximal anchor and the second most proximal anchor in the implant catheter 236. For example, for left ventriculoplasty, the suture routing component can be loaded between the second ventricular wall anchor and the ventricular septum anchor. In an example, for right ventriculoplasty, the suture routing component 2018 can be loaded between the first ventricular wall anchor 2004 and the second ventricular wall anchor 2006.

Figure 3A:
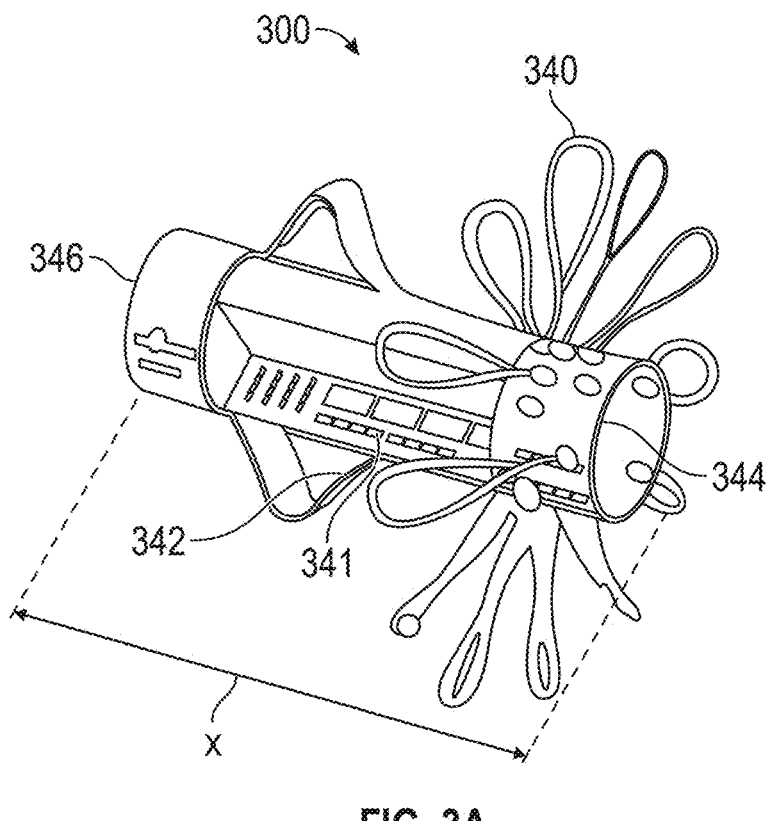
FIG. 3A illustrates an example of a ventricular septum anchor with an integrated suture lock.

FIGS. 3A-B, 4A-C, 5, and 6 illustrate non-limiting examples of ventricular anchors that can be deployed by the above-described catheter system 200. For example, FIG. 3A illustrates an example of a ventricular anchor 300, or a ventricular septum anchor. Optionally, the ventricular anchor 300, or septal anchor, can have an integrated suture lock.

The ventricular anchor 300 can be used as a ventricular septum anchor. In some embodiments, the ventricular anchor 300 can be used as a ventricular wall anchor. The ventricular anchor 300 can include a central body 341 with an anchor on a distal portion of the central body 341 and, optionally, a suture lock 342 on a proximal portion of the central body. As illustrated, the anchor can have a plurality of wings 340 extending radially outward from the central body 341.

The central body 341 can be a tubular body having an opening 344 on the distal end of the central body 341, or the end facing the left ventricle when placed. The ventricular anchor 300 can have an opening 346 on the proximal end of the central body 341, or the end facing the right ventricle when placed. The central body 341 can be cylindrical. In some embodiments, the central body 341 can be a prism.

The ventricular anchor 300 can be made of metal. For example, the ventricular anchor 300 can be made of titanium, steel, or nitinol.

The wings 340 can improve the ability of the ventricular anchor 300 to embed in the heart wall or ventricular septum. The wings 340 can serve as stabilizing elements, ensuring secure attachment to the heart wall or ventricular septum. The wings 340 can be loops or arches with space for cardiac tissue in the center of each loop. The wings 340 can be shaped similar to those of a malecot catheter. The wings 340 can pinch, clamp, or grip the heart wall tissue to keep the anchor in place. The wings 340 can be circumferentially disposed around a central body of the ventricular anchor 300. The ventricular anchor 300 can have twelve wings 340. In some embodiments, the ventricular anchor 300 can have at least five and/or less than or equal to 15 wings 340. In some embodiments, the ventricular anchor 300 can have at least two and/or less than or equal to 20 wings 340. In some embodiments, the ventricular anchor 300 can have only one wing 340. The wings 340 can be curved such that they grip the heart wall or ventricular septum tissue with an increased angle of contact, distributing forces more evenly as the ventricular anchor 300 embeds. Advantageously, this can reduce stress concentrations and enhance compatibility with the tissue.

In some examples, the wings can be double nested, with some wings radially smaller than others. In some embodiments, the smaller wings can be inside the larger wings. This can maximize the surface area of the ventricular anchor 300 in contact with the tissue and increase the holding force. The double nested wings 340 can also minimize the profile of the anchor, reducing the risk of unintentional damage while increase holding potential. The ventricular anchor 300 can be self-expanding. For example, the ventricular anchor 300 can be expanded by advancing the ventricular anchor 300 outside a catheter. The wings may also be connected to each other via radial struts in order to increase holding force.

Figures 4A, 4B, 4C:
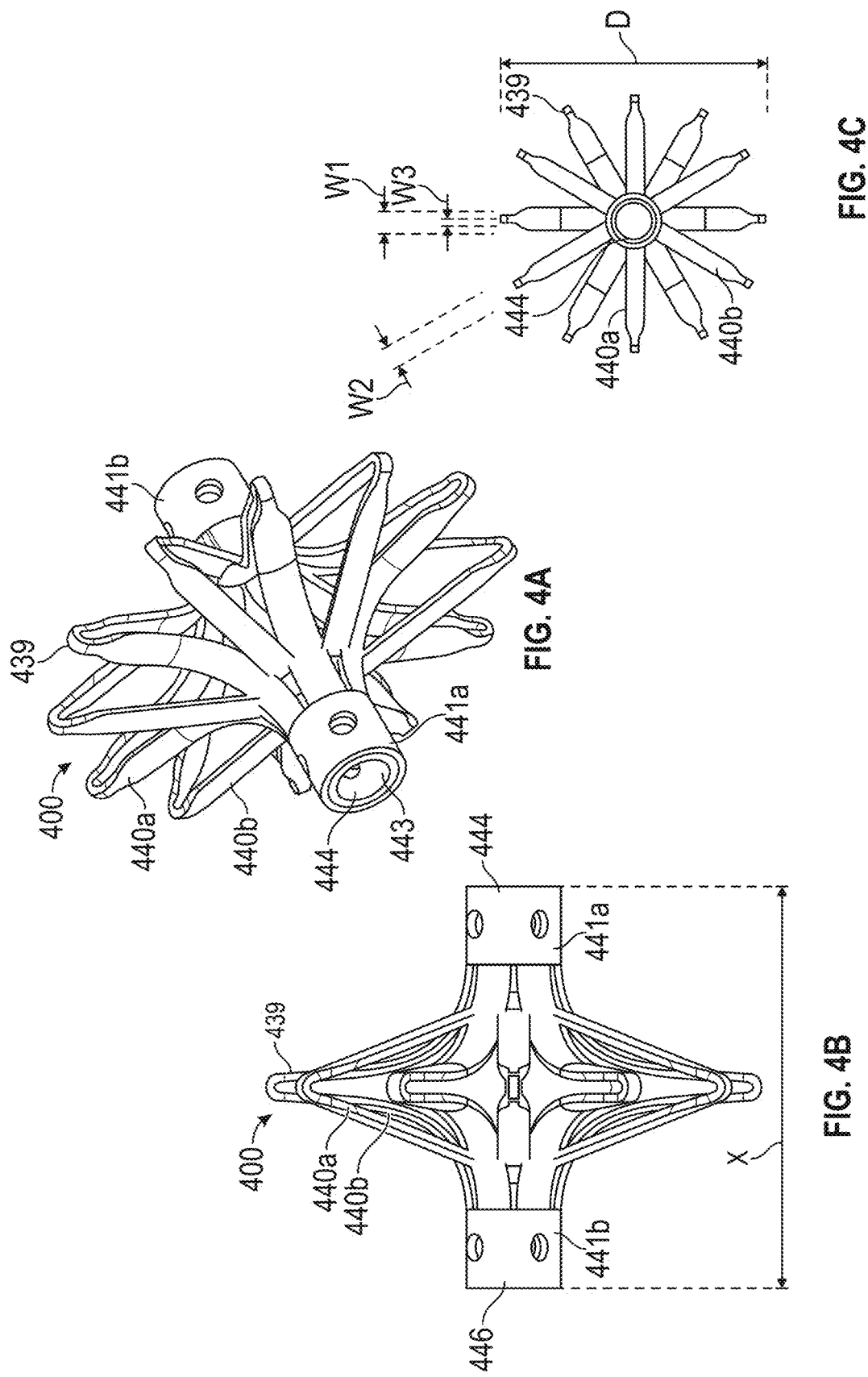
FIG. 4A is a perspective view of another example of a ventricular anchor.
FIG. 4B is a side view of the ventricular anchor of FIG. 4A.
FIG. 4C is a top view of the example of a ventricular anchor of FIG. 4A.

With respect to dimension X in FIG. 3A, or the dimension from the proximal end to the distal end of the anchor 300, the wings 340 can be narrower than the wings 440 of the ventricular anchors 400 of FIGS. 4A-B. This can be advantageous as the ventricular anchor 300 can be designed for use in the ventricular septum, and the ventricular septum can be thinner than the ventricular walls.

Figures 12, 13:
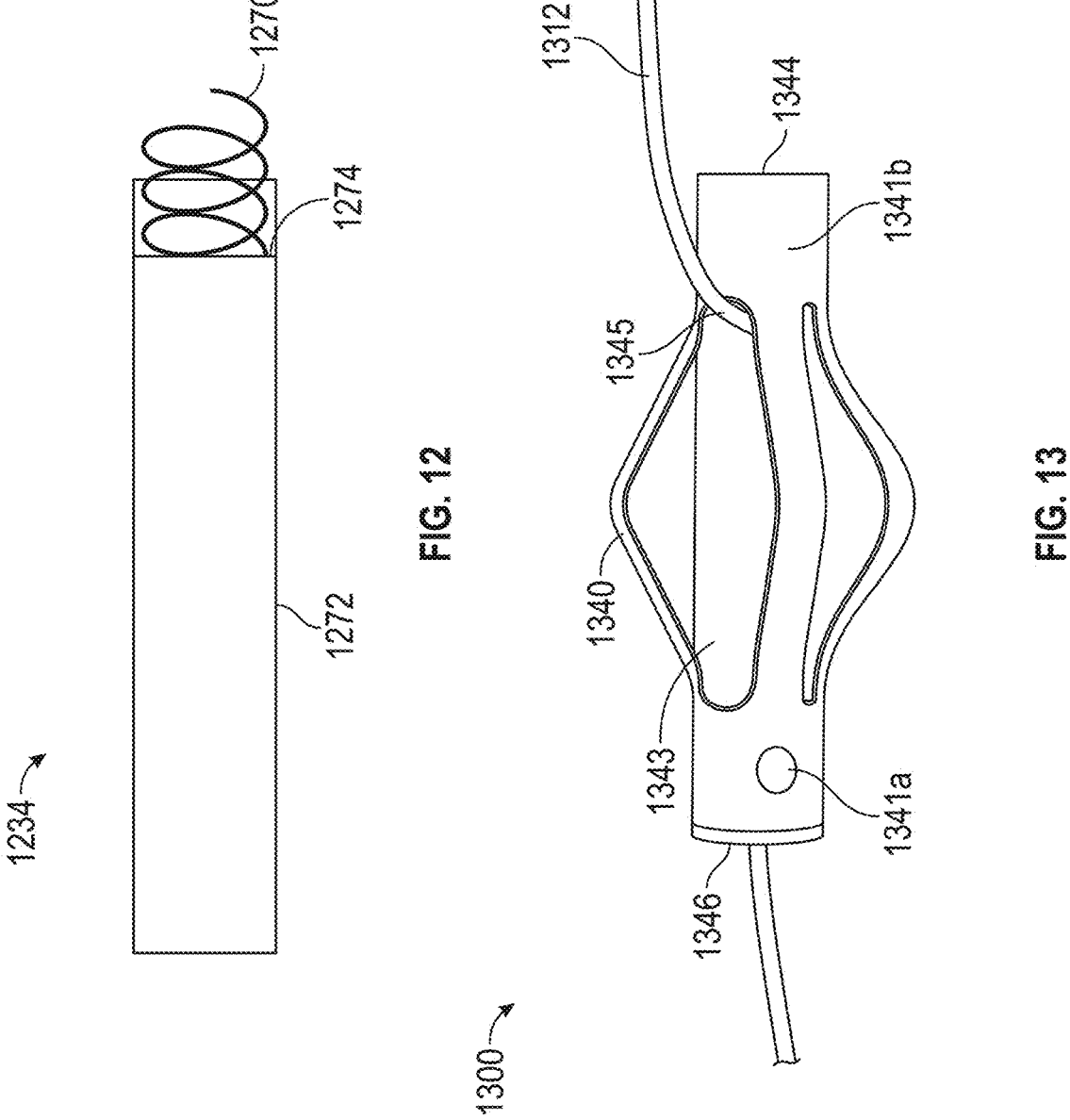
FIG. 12 illustrates a distal end of a jacketed anchoring catheter.
FIGS. 13-15 illustrate examples of suture locks.
Figure 14:
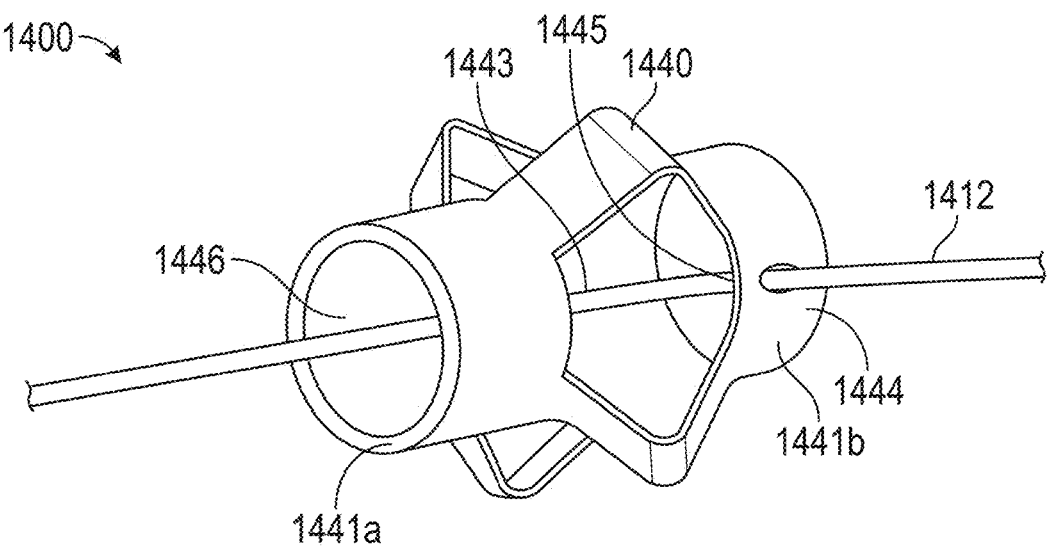
Figure 15:
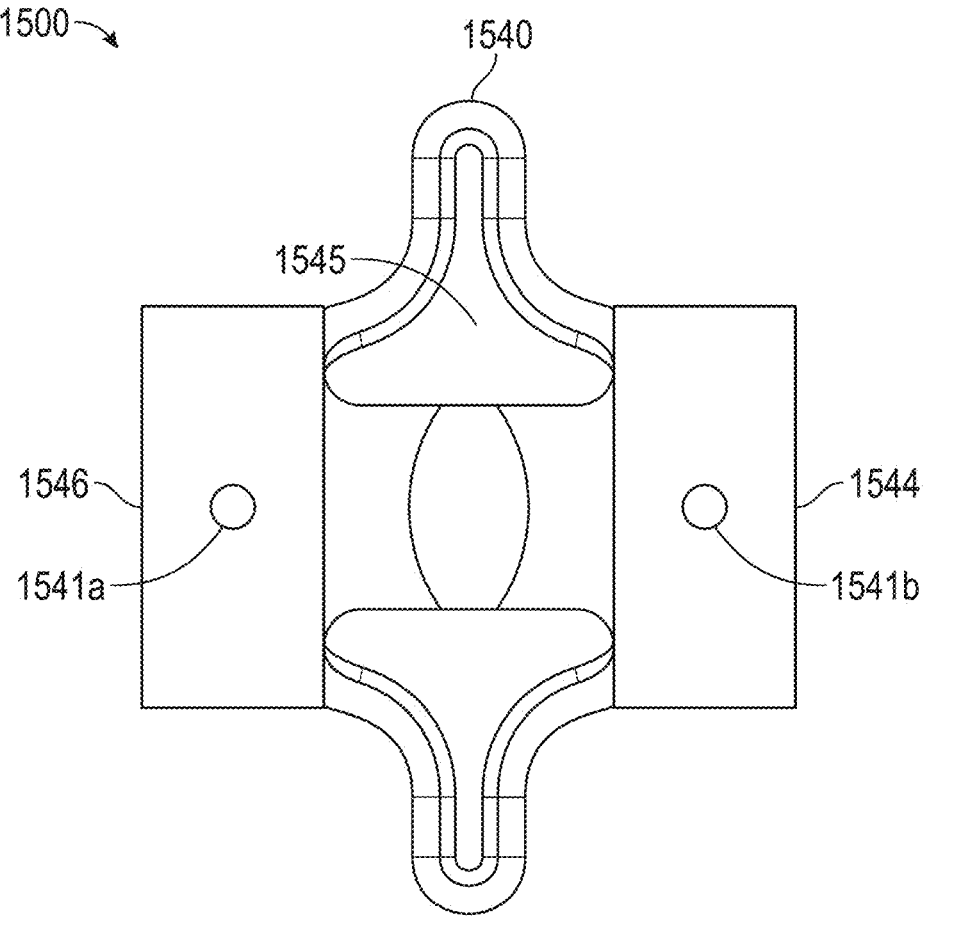

The suture lock 342 can lock the sutures tethered to the ventricular anchor 300 at a desired tension. The suture lock 342 can be positioned in the right ventricle when placed. The suture lock 342 can be engaged once the sutures are tensioned and the suture lock is unsheathed. Non-limiting examples of the suture lock are shown in FIGS. 13 to 15.

The suture lock 342 can be held radially constrained in an unlocked position while the suture lock 342 is sheathed. Once a desired tension has been achieved, the suture lock 342 can be unsheathed to spring the suture lock 342 radially outward to a locked position. Multiple sutures can be run through the suture lock 342. The suture lock 342 can include a plurality of elements, for example two to four, that spring or expand radially outward to a locked position when unsheathed. In some embodiments, the suture lock 342 can include at least one and/or less than or equal to ten elements that spring or expand radially outward to a locked position when unsheathed. When in a locked position, the suture lock 342 can trap or capture the suture between opposing layers. In some embodiments, the suture lock 342 can be unlocked by advancing a sheath over the suture lock 342, or resheathing the suture lock 342.

The ventricular anchor 300 can include a hemostasis element in the central lumen of the anchor, for example between the opening 344 and the opening 346. The hemostasis element can be deployed by the implant catheter into the central lumen. The hemostasis element can be a pad, for example a pad made of collagen, silicon, cellulose, or a polymer. The hemostasis element can be a valve or cap configured to selectively or permanently stop blood flow through the central lumen of the ventricular anchor 300.

Figure 3B:
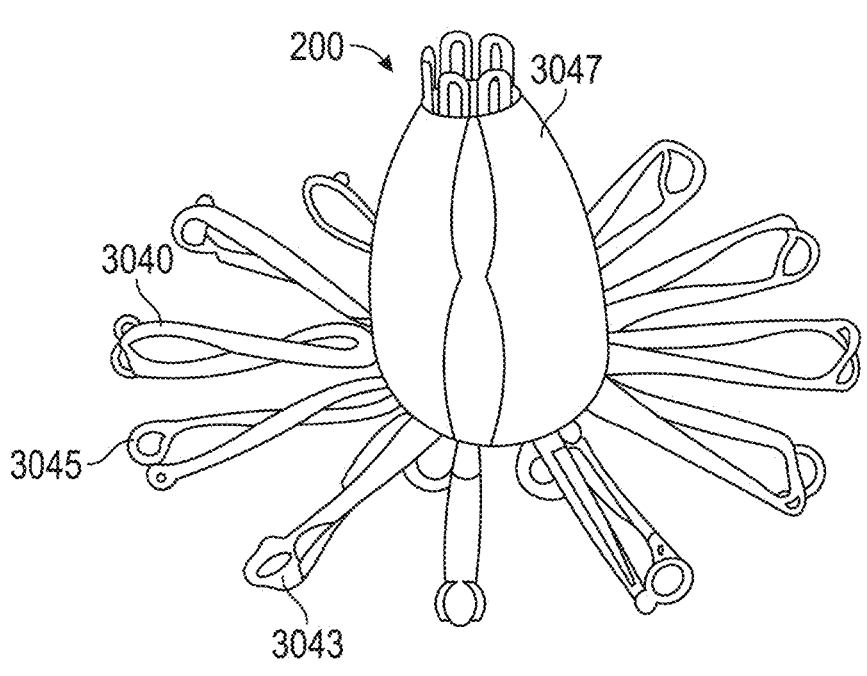
FIG. 3B illustrates an example of a ventricular anchor.

FIG. 3B illustrates an example of a ventricular anchor 301, or a ventricular wall anchor.

The ventricular anchor 301 can include any of the features of the ventricular anchor 300 of FIG. 3A.

The wings 3040 can improve the ability of the ventricular anchor 301 to embed in the heart wall or ventricular septum. The wings 3040 can serve as stabilizing elements, ensuring secure attachment to the heart wall or ventricular septum. The wings 3040 can be loops or arches with space for cardiac tissue in the center of each loop. The wings 3040 can be shaped similar to those of a malecot catheter. The wings 3040 can pinch, clamp, or grip the heart wall tissue to keep the anchor in place. The wings 3040 can be circumferentially disposed around a central body of the ventricular anchor 301. The ventricular anchor 301 can have twelve wings 3040. In some embodiments, the ventricular anchor 301 can have at least five and/or less than or equal to 15 wings 3040. In some embodiments, the ventricular anchor 301 can have at least two and/or less than or equal to 20 wings 3040. In some embodiments, the ventricular anchor 301 can have only one wing 3040. The wings 3040 can be curved such that they grip the heart wall or ventricular septum tissue with an increased angle of contact, distributing forces more evenly as the ventricular anchor 301 embeds. Advantageously, this can reduce stress concentrations and enhance compatibility with the tissue.

The wings 3040 can include an opening 3043 on the distal tip of each wing 3040. The opening 3043 can be defined by outward facing arms 3045 that allow the wing 3040 to better grip the heart wall. For example, the outward facing arms 3045 can grip the pericardium and myocardium from within the pericardial space.

The ventricular anchor 301 can include a hemostasis element 3047 on a proximal end of the ventricular anchor 301. The hemostasis element 3047 is described with respect to FIG. 29.

The ventricular anchor 301 can include another hemostasis element in the central lumen of the anchor. The hemostasis element can be deployed by the implant catheter into the central lumen. The hemostasis element can be a pad, for example a pad made of collagen, silicon, cellulose, or a polymer. The hemostasis element can be a valve or cap configured to selectively or permanently stop blood flow through the central lumen of the ventricular anchor 301.

FIG. 4A is a perspective view of another example of a ventricular anchor 400. FIG. 4B is a side view of the example of a ventricular anchor 400 of FIG. 4A. FIG. 4C is a top view of the example of a ventricular anchor 400 of FIG. 4A. The ventricular anchor 400 can include any of the features of the ventricular anchor 300.

The ventricular anchor 400 can be used as a ventricular wall anchor. In some embodiments, the ventricular anchor 400 can be used as a ventricular septum anchor. The ventricular anchor 400 can include a plurality of wings 440.

The ventricular anchor 400 can have an opening 444 on the distal body 441a, or the end facing the wall or exterior of the ventricle when placed. The ventricular anchor 400 can have an opening 446 on the proximal body 441b, or the end facing the interior of the left ventricle when placed. The distal body 441a can be cylindrical. In some embodiments, the distal body 441a can be a prism. The proximal body 441b can be cylindrical. In some embodiments, the proximal body 441b can be a prism.

The ventricular anchor 400 can be made of metal. For example, the ventricular anchor 400 can be made of titanium, steel, nitinol, or other biocompatible material.

The wings 440 can improve the ability of the ventricular anchor 300 to embed in the heart wall or ventricular septum. The wings 440 can serve as stabilizing elements, ensuring secure attachment to the heart wall or ventricular septum. The wings 440 can be loops or arches with space for cardiac tissue in the center of each loop. The wings 440 can be shaped similar to those of a malecot catheter. The wings 440 can pinch, clamp, or grip the heart wall tissue to keep the anchor in place. The wings 440 can be circumferentially disposed around a central body of the ventricular anchor 400. The ventricular anchor 400 can have 12 wings 440. In some embodiments, the ventricular anchor 400 can have 5-15 wings 440. In some embodiments, the ventricular anchor 400 can have 2-20 wings 440. In some embodiments, the ventricular anchor 400 can have one wing 440. The wings 440 can be curved such that they grip the heart wall or ventricular septum tissue with an increased angle of contact, distributing forces more evenly as the ventricular anchor 400 embeds. Advantageously, this can reduce stress concentrations and enhance compatibility with the tissue.

In some examples, the wings 440 can be double nested, with some wings radially smaller than others. In some embodiments, the smaller wings, or inner wings, can be inside the larger wings, or outer wings. This can maximize the surface area of the ventricular anchor 400 in contact with the tissue and increase the holding force. The double nested wings 440 can also minimize the profile of the anchor, reducing the risk of unintentional damage while increase holding potential.

In some implementations, the wings 440 can be cut from multiple smaller tubes. For example, the wings 440 can be cut from two smaller cutes to form a smaller crimped profile. In some implementations, the double nested anchor 400 can have a crimped profile of at least 1 mm and/or less than or equal to 3 mm, for example between 1.5 mm and 2 mm. In some implementations, the double nested anchor 400 can have 15-20 wings. In some implementations, the double nested anchor 400 can have 10-30 wings. In some implementations, an anchor that is not double nested may be cut from a larger tube. In some implementations, the anchor that is not double nested can have a crimped profile of at least 2 mm and/or less than or equal to 5 mm, for example between 3 mm and 4 mm. The double nested anchor 400 and the anchor that is not double nested may offer comparable levels of stiffness and tissue engagement.

With respect to dimension X of FIG. 4B, or the dimension from the proximal end to the distal end of the anchor 400, the wings 440 can be wider than the wings 340 of the ventricular anchors 300 of FIG. 3A. This can be advantageous as the ventricular anchor 400 can be designed for use in the ventricular walls, and the ventricular walls can be thicker than the ventricular septum.

In some implementations, the anchor 400 can have a length along dimension X of at least about 2.5 mm and/or less than or equal to about 12.7 mm, for example between 6.35 mm and 7.62 mm. In some implementations, the diameter of the distal body 441*a* of the anchor 400 can be at least about 12.7 mm and/or less than or equal to 25.4 mm. In some implementations, the diameter of the distal body 441*a* of the anchor 400 can be at least 2.5 mm and/or less than or equal to 50.8 mm. In some implementations, the diameter of the proximal body 441*b* of the anchor 400 can be at least 2.5 mm and/or less than or equal to 50.8 mm, for example between 12.7 mm and 25.4 mm.

When the anchor 400 is expanded, the largest diameter D of the anchor 400 can be the distance from the end of a wing 440*a,b* to the end of an opposite wing 440*a,b*. In some implementations, the anchor 400 can have a largest diameter D of at least 2.5 mm and/or less than or equal to 19.05 mm, for example between 6.35 mm and 12.7 mm.

The ventricular anchor 400 can have a low profile along dimension X. The profile of the ventricular anchor 400 can include the overall length, the length that extends from the wing 440 to the distal tip of the anchor 400, and/or the length from the proximal side of the wing 440 to the proximal end of the anchor 400. In some implementations, the wings 440*a,b* of the anchor 400 can be made of wire with a width along dimension X of at least 0.025 mm and/or less than or equal to 2.5 mm, for example between 0.08 mm and 0.25 mm. In some implementations, each wing 440*a* can have a width W1 of at least 1.27 mm and/or less than or equal to 25.4 mm, for example between 2.5 mm and 12.7 mm. In some implementations, each wing 440*b* can have a width W2 of at least 1.27 mm and/or less than or equal to 25.4 mm, for example between 2.5 mm and 12.7 mm. The length of the anchor 400 from the wing 440 to the distal tip can be minimized, so this length can sit in the pericardial space without damaging surrounding tissue. In some examples, the anchor 400 can have a length from the wing 440 to the distal tip of around 3 mm. The anchor 400 can have a length from the wing 440 to the distal tip of greater than about 1.27 mm and/or less than about 12.7 mm. The anchor 400 can have a length from the wing 440 to the distal tip of greater than about 0.25 mm and/or less than about 25.4 mm. The length of the anchor 400 from the wing 440 to the proximal tip can be minimized, so this length does not protrude into the left ventricle. In some examples, the anchor 400 can have a length from the wing 440 to the proximal tip of around 3.048 mm. The anchor 400 can have a length from the wing 440 to the proximal tip of greater than about 1.27 mm and/or less than about 12.7 mm. The anchor 400 can have a length from the wing 440 to the proximal tip of greater than about 0.25 mm and/or less than about 25.4 mm. Advantageously, the ventricular anchor 400 can be forgiving to the myocardium, but offer superior retention force.

At least one of the wings 440 can include a thin portion 439 at the most radially outward point of each wing 440. The thin portion 439 can have a smaller thickness than the radially inward portion of each wing 440. In some embodiments, the thin portion 439 can be a tapered portion of the wing 440. In some embodiments, the ventricular anchor 400 can include a suture lock similar to the ventricular anchor 300 as described in FIG. 3A. The ventricular anchor 400 can be self-expanding. For example, the ventricular anchor 400 can be expanded by advancing the ventricular anchor 400 outside a catheter. In some implementations, the thin portion 439 can have a width along the dimension X of at least 1.27 mm and/or less than or equal to 25.4 mm, for example between 2.5 mm and 12.7 mm. In some implementations, the thin portion 439 can have a width W3 of at least 0.25 mm and/or less than or equal to 25.4 mm, for example between 1.27 mm and 12.7 mm.

The ventricular anchor 400 can include a hemostasis element in the central lumen of the anchor, for example between the opening 444 and the opening 446. The hemostasis element can be deployed by the implant catheter into the central lumen. The hemostasis element can be a pad, for example a pad made of collagen, silicon, cellulose, or a polymer. The hemostasis element can be a valve or cap configured to selectively or permanently stop blood flow through the central lumen of the ventricular anchor 400. The hemostasis element can be a nitinol piece which can selectively or permanently stop blood flow through the central lumen of the ventricular anchor 400.

The ventricular anchor 400 can include an inner body 443. The inner body 443 can be radially inside the outer distal body 441*a*. The inner body 443 can be radially inside the outer proximal body 441*b*. The inner body 443 can include an inner distal body and an inner proximal body. The inner wings 440*a* can be part of the inner body 443, fixed to the inner distal body and an inner proximal body. The outer wings 440*b* can be part of the outer body, fixed to the outer distal body 441*a* and an outer proximal body 441*b*.

Figure 5:
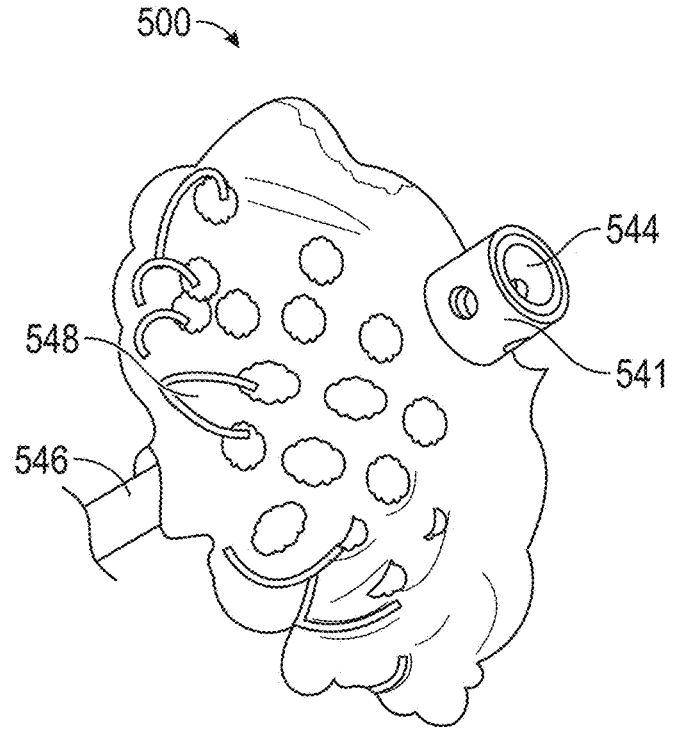
FIG. 5 illustrates another example of a ventricular anchor.

FIG. 5 illustrates another example of a ventricular anchor 500. The ventricular anchor 500 can include any of the features of the ventricular anchors 300, 400 of FIGS. 3 and 4A-B. The ventricular anchor 500 can have wings, an opening 544 on the distal end of the central body 541, and an opening 546 on the proximal end of the central body 541. The central body 541 can be cylindrical. In some embodiments, the central body 541 can be a prism. In some embodiments, the central body 541 can have a gap in the center, between the wings 540. In some embodiments, the central body 541 can be extend through the space between the wings 540.

The ventricular anchor 500 can be covered with a soft material 548. For example, the soft material 548 can cover the wings of the ventricular anchor 500. The soft material 548 can be silicone, polyurethane, hydrogel, collagen-based material, a polymeric layer, or an elastomer. The soft material 548 can reduce tissue damage, for example by reducing the risk of irritation, inflammation, or rejection. The soft material 548 can enhance anchoring by conforming to the irregular surface of the heart tissue, providing greater stability. The soft material 548 can allow for greater flexibility and adaptability of the anchor as the heart tissue flexes. The soft material 548 can promote stable ingrowth. For example, the soft material 548 can promote stable ingrowth long-term. In some embodiments, the soft material 548 can promote stable ingrowth over a period of at least 1 year or at least 5 years. In some embodiments, the soft material 548 can promote stable ingrowth over a period of at least 6 months or at least 10 years.

Figure 6:
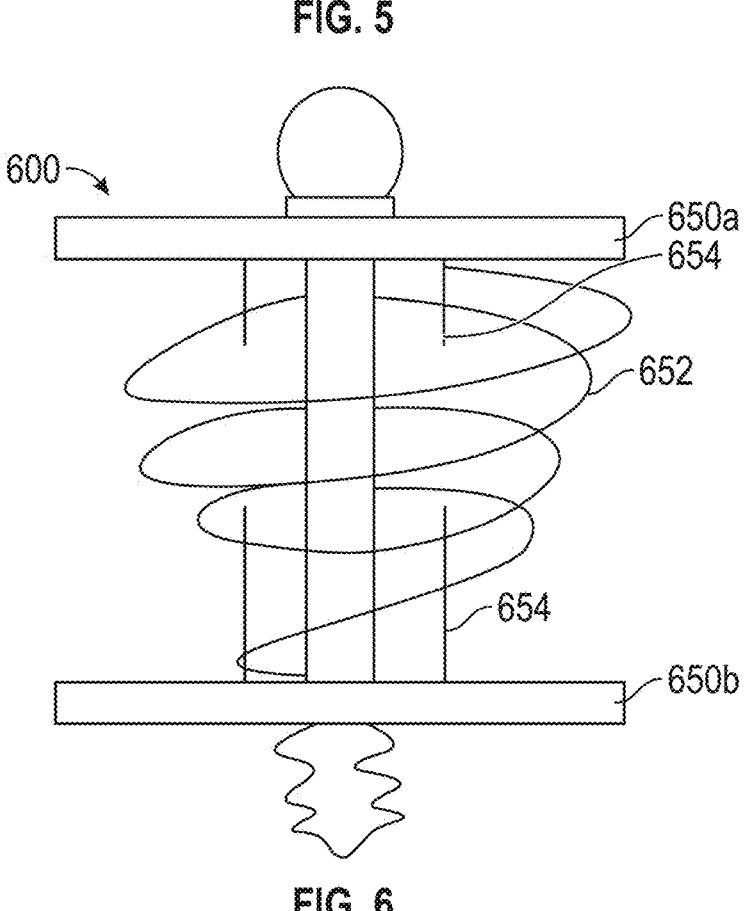
FIG. 6 illustrates another example of a ventricular anchor with integrated pledgets.

FIG. 6 illustrates another example of a ventricular anchor 600 with integrated pledgets. The ventricular anchor 600 can include an inner pledget 650a and an outer pledget 650b. The inner pledget 650a can be positioned on the inner surface of the ventricular wall and the outer pledget 650b can be positioned on the outer surface of the ventricular wall. The helical component 652 can allow the ventricular anchor 600 to embed in the tissue of the ventricular wall. The tubular supports 654 can support the helical component 652. The tubular supports 654 can be positioned on the inner surfaces of the outer pledget 650a and inner pledget 650b.

FIG. 7 illustrates an example of a suture tensioning arrangement 700 that can be used with any of the above-described anchors. One or more sutures can be routed through one or more of the anchors and through the suture routing component 760. The one or more sutures can be routed in a manner such that the one or more sutures may be independently tensioned and/or at the same time.

The suture 712 can be tethered to a first ventricular wall anchor 704 and a suture routing component 760. The suture routing component 760 can be a ring about which multiple sutures can be tied. In some embodiments, the suture routing component 760 can be a cylinder, a prism, or a component with multiple openings. In some embodiments, the suture routing component can be a round smooth ring. In some embodiments, the suture routing component can be a ring without edges. The suture routing component 760 can be pre-loaded in the implant catheter. The suture 712 can be untethered from a second ventricular wall anchor 706. Tightening the suture 712 can reduce the size of the ventricle in the dimension between the first ventricular wall location and the ventricular septum without significantly reducing the size of the ventricle in the dimension between the second ventricular wall location and the ventricular septum. Advantageously, if the ventricle of the patient is more dilated in the dimension between the first ventricular wall location and the ventricular septum than the dimension between the second ventricular wall location and the ventricular septum, this suture tensioning arrangement 700 can allow a user to correct the more dilated area of the ventricle.

The suture 714 can be tethered to a second ventricular wall anchor 706 and the suture routing component 760. The suture 714 can be untethered from a first ventricular wall anchor 704. Tightening the suture 714 can reduce the size of the ventricle in the dimension between the second ventricular wall location and the ventricular septum without significantly reducing the size of the ventricle in the dimension between the first ventricular wall location and the ventricular septum. Advantageously, if the ventricle of the patient is more dilated in the dimension between the second ventricular wall location and the ventricular septum than the dimension between the first ventricular wall location and the ventricular septum, this suture tensioning arrangement 700 can allow a user to correct the more dilated area of the ventricle.

The suture 717 can be tethered to the suture routing component 760. Pulling the suture 717 can tension both sutures 712 and 714. Sutures 712, 714, 716 can be routed through a ventricular septum anchor. The sutures 712, 714, 716 can be tensioned independently proximal to the ventricular septum anchor to enhance user control over the dimensions in which the ventricle diameter is reduced. The suture routing component 760 can keep the sutures away from the chordae, reducing potential complications resulting from contact with the chordae.

FIG. 8 illustrates an example of a suture tensioning arrangement 800. The suture 812 can be tethered to a first ventricular wall anchor 804, a second ventricular wall anchor 806, and a suture routing component 860. The suture routing component 860 can be a ring about which multiple sutures can be tied. In some embodiments, the suture routing component 860 can be a cylinder, a prism, or a component with multiple openings. The suture routing component 860 can be pre-loaded in the implant catheter. Tightening the suture 812 can reduce the size of the ventricle in the dimension between the first ventricular wall location and the ventricular septum without significantly reducing the size of the ventricle in the dimension between the second ventricular wall location and the ventricular septum. Tightening the suture 812 can also reduce the size of the ventricle in the dimension between the first ventricular wall location and the second ventricular wall location without significantly reducing the size of the ventricle in the dimension between the second ventricular wall location and the ventricular septum. Advantageously, if the ventricle of the patient is more dilated in the dimension between the first ventricular wall location and the ventricular septum than the dimension between the second ventricular wall location and the ventricular septum, this suture tensioning arrangement 800 can allow a user to correct the more dilated area of the ventricle. Advantageously, if the ventricle of the patient is more dilated in the dimension between the first ventricular wall location and the second ventricular wall location than the dimension between the second ventricular wall location and the ventricular septum, this suture tensioning arrangement 800 can allow a user to correct the more dilated area of the ventricle.

The suture 814 can be tethered to a first ventricular wall anchor 804, a second ventricular wall anchor 806, and a suture routing component 860. Tightening the suture 814 can reduce the size of the ventricle in the dimension between the second ventricular wall location and the ventricular septum without significantly reducing the size of the ventricle in the dimension between the first ventricular wall location and the ventricular septum. Tightening the suture

812 can also reduce the size of the ventricle in the dimension between the second ventricular wall location and the first ventricular wall location without significantly reducing the size of the ventricle in the dimension between the first ventricular wall location and the ventricular septum. Advantageously, if the ventricle of the patient is more dilated in the dimension between the second ventricular wall location and the ventricular septum than the dimension between the first ventricular wall location and the ventricular septum, this suture tensioning arrangement 800 can allow a user to correct the more dilated area of the ventricle. Advantageously, if the ventricle of the patient is more dilated in the dimension between the second ventricular wall location and the first ventricular wall location than the dimension between the first ventricular wall location and the ventricular septum, this suture tensioning arrangement 800 can allow a user to correct the more dilated area of the ventricle.

The suture 817 can be tethered to the suture routing component 860. Pulling the suture 817 can tension both sutures 812 and 814. Sutures 812, 714, 816 can be routed through a ventricular septum anchor. The sutures 812, 814, 816 can be tensioned independently proximal to the ventricular septum anchor to enhance user control over the dimensions in which the ventricle diameter is reduced. The suture routing component 860 can keep the sutures away from the chordae, reducing potential complications resulting from contact with the chordae.

FIG. 9 illustrates another example of a suture tensioning arrangement 900. Unlike the prior arrangements, the suture tensioning arrangement 900 does not need a separate routing component in the left ventricle. One or more sutures can be routed through one or more of the ventricular wall anchors and back to the ventricular septum anchor, for example through a suture lock.

The suture 912 can be tethered to a first ventricular wall anchor 904, a ventricular septum anchor 902, and a second ventricular wall anchor 906. Tightening the suture 912 can reduce the size of the ventricle in the dimension between the first ventricular wall location and the ventricular septum. Tightening the suture 912 can reduce the size of the ventricle in the dimension between the second ventricular wall location and the ventricular septum. A proximal end 913 of the suture 912 can be in the right ventricle, proximal to a suture lock of the ventricular septum anchor 902. Tensioning a first side of the proximal end 913 of the suture 912 can more significantly reduce the dimension between the first ventricular wall location and the ventricular septum. Tensioning a second side of the proximal end 913 of the suture 912 can more significantly reduce the dimension between the second ventricular wall location and the ventricular septum. Tensioning the proximal end 913 of the suture 912 evenly can reduce the dimension between the first ventricular wall location and the ventricular septum and the dimension between the second ventricular wall location and the ventricular septum evenly.

FIG. 10 illustrates an example of a suture tensioning arrangement 1000. The suture 1016 can be tethered to a first ventricular wall anchor 1004 and a second ventricular wall anchor 1006. The suture 1018 can be tethered to the suture 1016, for example the center of the suture 1016, and a ventricular wall anchor 1002. Tensioning the proximal end 1013 of the suture 1016 can reduce the dimension between the first ventricular wall location, the second ventricular wall location, and the ventricular septum.

Figures 11A, 11B:
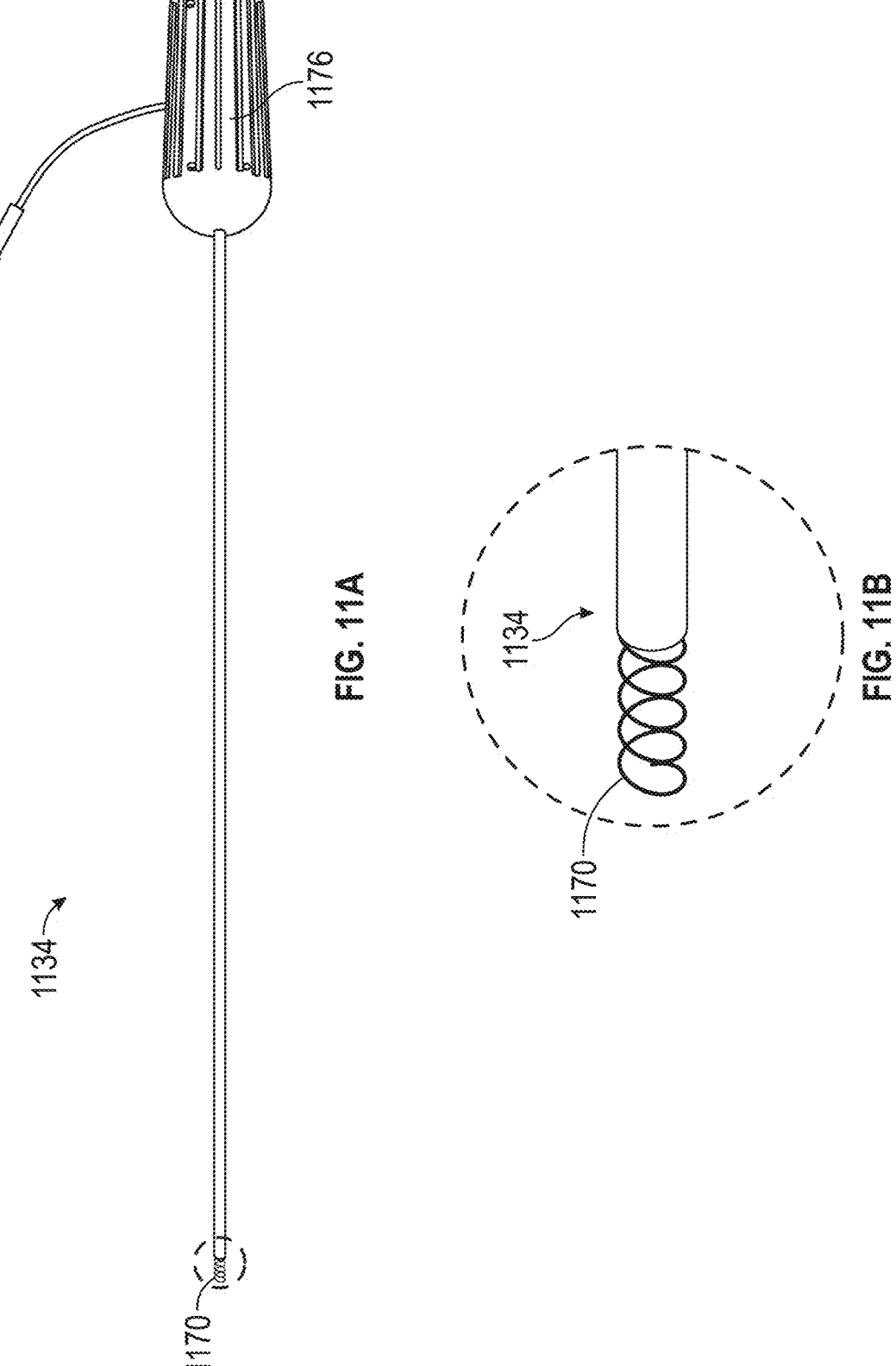
FIG. 11A illustrates an example of an anchoring catheter.
FIG. 11B illustrates a distal end of the anchoring catheter of FIG. 11A.

FIG. 11A illustrates an example of an anchoring catheter 1134. FIG. 11B illustrates a distal end of the anchoring catheter 1134 of FIG. 11A.

The anchoring catheter 1134 can include or carry an anchoring coil 1170, barb, or other anchoring structure on the distal end. The anchoring coil 1170 can be used to anchor the catheter system in the heart wall. The anchoring of the anchoring catheter 1134 to the heart wall can be temporary. The anchoring coil 1170 can be advanced into the heart wall, for example the ventricular wall. The anchoring coil 1170 can rotate during insertion into the heart wall to embed in the pericardium and myocardium. The anchoring coil 1170 can rotate in the opposite direction during retraction to avoid damaging the heart wall tissue. The anchors can be advanced from the implant catheter such that they are positioned distal to the anchoring coil 1170. In some embodiments, non-limiting examples of the guide sheath, septal crossing catheter, guidewire, or implant catheter, are shown in FIGS. 1C-D and 17A-B, can include the features of the anchoring catheter 1134, for example the anchoring coil 1170. Alternatively, the anchoring structure may be incorporated into one of the implantable anchors.

The anchoring catheter 1134 can be made of metal, for example aluminum or steel. The anchoring catheter 1134 can include a cylindrical tube, for example a laser cut tube. The anchoring catheter 1134 can stabilize the catheter system to improve predictability. The anchoring catheter 1134 can be guided by the known coil pitch and the distance advanced by the catheter stand. The anchoring catheter 1134 can be guided with a short coil and strain relief. The anchoring coil 1170 can have a length of at least 0.1 mm and/or less than or equal to 10 mm, for example between 1 mm and 5 mm. In some implementations, the anchoring coil 1170 can have a length that allows it to extend into the ventricular wall at least 0.1 mm and/or less than or equal to 10 mm, for example between 1 mm and 5 mm. Current devices often use shorter screws to anchor in the heart wall. Advantageously, the anchoring coil 1170 can provide more mechanical stability than a shorter screw due to the greater length and/or surface area.

Figure 17A:
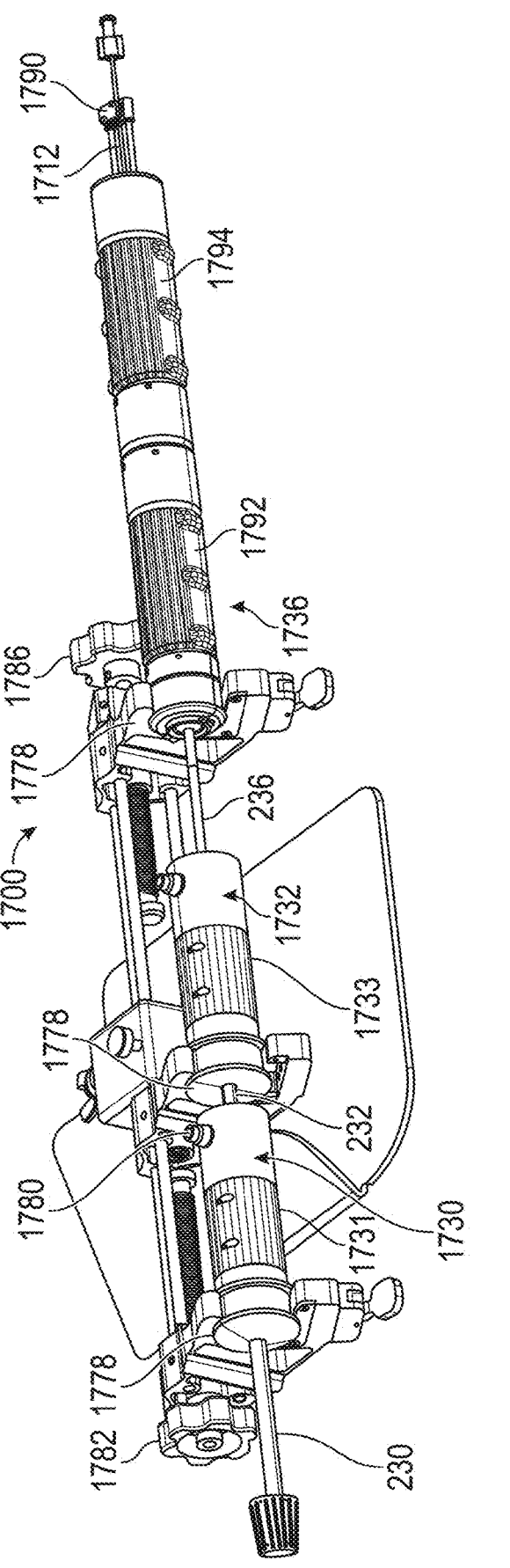
FIG. 17A illustrates an example of a catheter stand for guiding a catheter system.
Figure 17B:
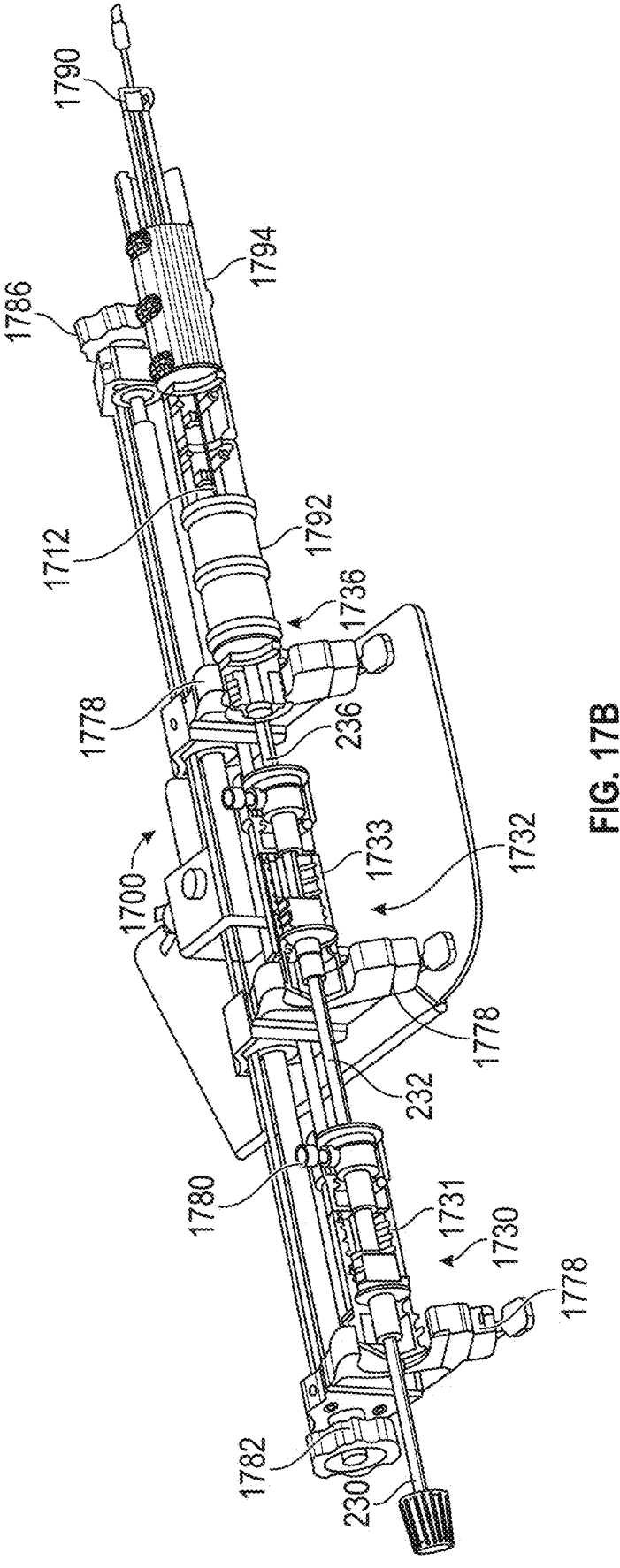
FIG. 17B illustrates a cross-sectional view of the catheter stand of FIG. 17A.

A user can guide the anchoring catheter 1134 using the proximal portion 1176. A user can move the proximal portion 1176 and advance the anchoring catheter 1134 into the desired position. In some embodiments, the proximal portion 1176 of the anchoring catheter 1134 can connect to a catheter stand. Non-limiting examples of the catheter stand are shown in FIGS. 17A-B. The proximal portion 1176 of the anchoring catheter 1134 can allow user control of the anchoring catheter 1134.

FIG. 12 illustrates a distal end of a jacketed anchoring catheter 1234. The jacketed anchoring catheter 1234 can be similar to the anchoring catheter 1134 of FIGS. 11A-B. The jacketed anchoring catheter 1234 can include a jacket 1272 over the tube portion of the catheter. A jacket liner 1274 can extend onto the anchoring coil 1270. The jacket liner 1274 can be a strain relief. The jacket 1272, or coat, can electrically isolate the anchoring coil 1270. Advantageously, the electrical isolation can improve EDEN navigation, for example to minimize the depth the anchoring coil 1270 is advanced into the ventricular wall.

FIG. 13 illustrates an example of a suture lock 1300, which may be separate from or integrated with any of the above-described anchors.

The suture lock 1300 can include a distal portion 1341a and a proximal portion 1341b connected by a plurality of wings 1340. A separate central component 1343 can be radially inward of the distal portion 1341a and proximal portion 1341b. The central component 1343 can be a cylinder or prism. The central component 1343 can be fixed to the suture lock 1300. For example, the central component 1343 can be attached to the distal portion 1341*a* of the suture lock 1300 with a screw or adhesive. In some implementations, the central component 1343 can be fixed to the proximal portion 1341*b* of the suture lock 1300. For example, the central component 1343 can be attached to the proximal portion 1341*b* of the suture lock 1300 with a screw or adhesive.

The suture lock 1300 can have a proximal opening 1344, a distal opening 1346, and one or more peripheral openings 1345. The suture 1312 can be positioned through the distal opening 1346 and a peripheral opening 1345. When sheathed in a catheter, for example the implant catheter, the wings 1340 of the suture lock 1300 can be collapsed such that the suture lock 1300 unlocked. The wings 1340 of the suture lock 1300 can be collapsed such that they flex radially outward. In the unlocked position, the distal portion 1341*a* and the proximal portion 1341*b* can be further apart than in a locked position. The suture 1312 can be routed through the peripheral opening 1345 and the distal opening 1346. In some implementations, the suture 1312 can be routed through the proximal opening 1344 and the peripheral opening 1345. In the peripheral opening, the suture 1312 can be routed through a space between the central component 1343 and the proximal portion 1341*b*. In some implementations, in the peripheral opening, the suture 1312 can be routed through a space between the central component 1343 and the distal portion 1341*a*. With the suture lock 1300 in the unlocked state, the suture 1312 can be tensioned and loosened by advancing and retracting the suture 1312 relative to the suture lock 1300.

The suture lock 1300 can be self-expanding, such that when the suture lock 1300 is unsheathed, the wings 1340 expand such that the suture lock 1300 is locked. Locking the suture lock 1300 can cause the suture lock 1300 to foreshorten, such that the proximal portion 1341*b* and the distal portion 1341*a* move toward each other. The suture 1312 can be trapped or pinched between the central component 1343 and the proximal portion 1341*b*. In some implementations, the suture 1312 can be trapped or pinched between the central component 1343 and the distal portion 1341*a*. With the suture lock 1300 in the locked state, the suture 1312 cannot be tensioned or loosened. The point at which the suture 1312 is trapped between opposing layers can determine the tension at which the suture 1312 is locked.

FIG. 14 illustrates another example of a suture lock 1400. The suture lock 1400 can include a distal portion 1441*a* and a proximal portion 1441*b* connected by a plurality of wings 1440. A separate central component 1443 can be radially inward of the distal portion 1441*a* and proximal portion 1441*b*. The central component 1443 can be a cylinder or prism. The central component 1443 can be fixed to the distal portion 1441*a* of the suture lock 1400. For example, the central component 1443 can be attached to the distal portion 1441*a* of the suture lock 1400 with a screw or adhesive. In some implementations, the central component 1443 can be fixed to the proximal portion 1441*b* of the suture lock 1400. For example, the central component 1443 can be attached to the proximal portion 1441*b* of the suture lock 1400 with a screw or adhesive.

The suture lock 1400 can have a proximal opening 1444, a distal opening 1446, and one or more peripheral openings 1445. The suture 1412 can be positioned through the distal opening 1446 and a peripheral opening 1445. When sheathed in a catheter, for example the implant catheter, the wings 1440 of the suture lock 1400 can be collapsed such that the suture lock 1400 unlocked. The wings 1440 of the suture lock 1400 can be collapsed such that they flex radially outward. In the unlocked position, the distal portion 1441*a* and the proximal portion 1441*b* can be further apart than in a locked position. The suture 1412 can be routed through the peripheral opening 1445 and the distal opening 1446. In some implementations, the suture 1412 can be routed through the proximal opening 1444 and the peripheral opening 1445. In the peripheral opening, the suture 1412 can be routed through a space between the central component 1443 and the proximal portion 1441*b*. In some implementations, in the peripheral opening, the suture 1412 can be routed through a space between the central component 1443 and the distal portion 1441*a*. With the suture lock 1400 in the unlocked state, the suture 1412 can be tensioned and loosened by advancing and retracting the suture 1412 relative to the suture lock 1400.

The suture lock 1400 can be self-expanding, such that when the suture lock 1400 is unsheathed, the wings 1440 expand such that the suture lock 1400 is locked. Locking the suture lock 1400 can cause the suture lock 1400 to foreshorten, such that the proximal portion 1441*b* and the distal portion 1441*a* move toward each other. The suture 1412 can be trapped or pinched between the central component 1443 and the proximal portion 1441*b*. In some implementations, the suture 1412 can be trapped or pinched between central component 1443 and the distal portion 1441*a*. With the suture lock 1400 in the locked state, the suture 1412 cannot be tensioned or loosened. The point at which the suture 1412 is trapped between opposing layers can determine the tension at which the suture 1412 is locked.

FIG. 15 illustrates another example of a suture lock 1500 portion without a central component. The suture lock 1500 can include a distal portion 1541*a* and a proximal portion 1541*b* connected by a plurality of wings 1540. A separate central component can be radially inward of the distal portion 1541*a* and proximal portion 1541*b*. The central component can be a cylinder or prism. The central component can be fixed to the distal portion 1541*a* of the suture lock 1500. For example, the central component can be attached to the distal portion 1541*a* of the suture lock 1500 with a screw or adhesive. In some implementations, the central component can be fixed to the proximal portion 1541*b* of the suture lock 1500. For example, the central component can be attached to the proximal portion 1541*b* of the suture lock 1500 with a screw or adhesive.

The suture lock 1500 can have a proximal opening 1544, a distal opening 1546, and one or more peripheral openings 1545. The suture 1512 can be positioned through the distal opening 1546 and a peripheral opening 1545. When sheathed in a catheter, for example the implant catheter, the wings 1540 of the suture lock 1500 can be collapsed such that the suture lock 1500 unlocked. The wings 1540 of the suture lock 1500 can be collapsed such that they flex radially outward. In the unlocked position, the distal portion 1541*a* and the proximal portion 1541*b* can be further apart than in a locked position. The suture 1512 can be routed through the peripheral opening 1545 and the distal opening 1546. In some implementations, the suture 1512 can be routed through the proximal opening 1544 and the peripheral opening 1545. In the peripheral opening, the suture 1512 can be routed through a space between the central component and the proximal portion 1541*b*. In some implementations, in the peripheral opening, the suture 1512 can be routed through a space between the central component and the distal portion 1541*a*. With the suture lock 1500 in the unlocked state, the suture 1512 can be tensioned and loosened by advancing and retracting the suture 1512 relative to the suture lock 1500.

The suture lock 1500 can be self-expanding, such that when the suture lock 1500 is unsheathed, the wings 1540 expand such that the suture lock 1500 is locked. Locking the suture lock 1500 can cause the suture lock 1500 to fore-shorten, such that the proximal portion 1541*b* and the distal portion 1541*a* move toward each other. The suture 1512 can be trapped or pinched between the central component and the proximal portion 1541*b*. In some implementations, the suture 1512 can be trapped or pinched between the central component and the distal portion 1541*a*. With the suture lock 1500 in the locked state, the suture 1512 cannot be tensioned or loosened. The point at which the suture 1512 is trapped between opposing layers can determine the tension at which the suture 1512 is locked. FIG. 16A illustrates an example of an anchor 1604 embedded between the pericardium 1662 and myocardium 1664.

The wings 1640 of the anchor 1604 can be embedded in the space between the pericardium 1662 and myocardium 1664. In some implementations, the anchor 1604 can be embedded between the parietal layer of the serous pericardium and the visceral layer of the myocardium 1664, or the epicardium. The distal end of the anchor 1604 can be embedded in the tissue of the pericardium 1662. The proximal end of the anchor 1604 can be embedded in the tissue of the myocardium 1664. In some implementations, the anchor 1604 can be entirely embedded in the pericardium 1662. In some implementations, the anchor 1604 can be entirely embedded in the myocardium 1664.

An implant catheter delivering the anchor 1604 can pierce the endocardium 1666 and the myocardium 1664 in order to advance the anchor 1604 into the space between the pericardium 1662 and the myocardium 1664. The implant catheter can pierce the endocardium 1666 and myocardium 1664 from inside the left ventricle. In some implementations, a guidewire can pierce the endocardium 1666 and the myocardium 1664 in order to advance the anchor 1604 into the space between the pericardium 1662 and the myocardium 1664.

The suture 1612 tethered to the anchor 1604 can be routed through the myocardium 1664 and the endocardium 1666. The suture 1612 can be positioned in the space created by piercing the endocardium 1666 and myocardium 1664. Tension on the suture 1612 can pull the wings 1640 of the anchor 1604 against the myocardium 1664, or epicardium, to reduce dilation of the ventricle.

FIG. 16B illustrates an example of an anchor 1604 positioned outside a ventricular wall. The wings 1640 of the anchor 1604 can be positioned outside the ventricular wall. For example, the wings 1640 of the anchor 1604 can be positioned outside the pericardium 1662. The distal end of the anchor 1604 can be outside the heart wall. The proximal end of the anchor 1604 can be embedded in the tissue of the pericardium 1662. For example, the proximal end of the anchor 1604 can be embedded in the fibrous pericardium. In some implementations, the anchor 1604 can be entirely embedded in the pericardium 1662.

An implant catheter delivering the anchor 1604 can pierce the endocardium 1666, the myocardium 1664, and the pericardium 1662 in order to advance the anchor 1604 outside the heart wall. The implant catheter can pierce the endocardium 1666, myocardium 1664, and pericardium 1662 from inside the left ventricle. In some implementations, a guidewire can pierce the endocardium 1666, the myocardium 1664, and the pericardium 1662 in order to advance the anchor 1604 outside the heart wall.

The suture 1612 tethered to the anchor 1604 can be routed through the pericardium 1662, myocardium 1664, and endocardium 1666. The suture 1612 can be positioned in the space created by piercing the through the pericardium 1662, myocardium 1664, and endocardium 1666. Tension on the suture 1612 can pull the wings 1640 of the anchor 1604 against the pericardium 1662 to reduce dilation of the ventricle. For example, tension on the suture 1612 can pull the wings 1640 of the anchor 1604 against the fibrous pericardium to reduce dilation of the ventricle. Tension on the suture 1612 can pull the wings 1640 of the anchor 1604 against the outside of the heart wall to reduce dilation of the ventricle.

FIG. 17A illustrates an example of a catheter stand 1700 and catheter modules (also referred to herein as handles) of the catheter system 200 of FIGS. 1C and 1D. FIG. 17B illustrates a cross-sectional view of the catheter stand 1700 of FIG. 17A.

The catheter stand 1700 and catheter modules can stabilize the catheter system 200 while enabling controlled and independent movement of one or more catheters in the catheter system 200. The catheter stand 1700 and catheter modules can be positioned at a proximal end of the catheter system 200. In use, at least one catheter of the catheter system 200 may be advanced over a guidewire into the heart and then secured within the catheter stand 1700 and catheter modules. Depending on the approach, the catheter system 200 may be secured when the catheter system 200 is introduced into the right ventricle or the left ventricle. In some configurations, the catheter stand 1700 and catheter modules may be fully assembled or pre-loaded with each catheter before being advanced over the guidewire. In some implementations, the catheter stand 1700 and catheter modules can be used to advance the catheters of the catheter system 200 into the patient's heart. The catheter stand 1700 can advance and retract each catheter in the catheter system 200 independently. In some implementations, the catheter stand 1700 can advance and retract multiple catheters in the catheter system 200 simultaneously. The catheter modules can control movements of the catheters in different directions. The catheter modules can advance and retract elements within the catheters. The catheter stand 1700 and catheter modules can be operated by a user to control the catheters. In some implementations, the catheter stand 1700 and catheter modules can be controlled remotely or automatically.

The catheter stand 1700 can include one or more clamps to secure one or more of the catheter modules. For example, the catheter stand 1700 can include a separate clamp for each of one or more catheter modules. The catheter modules can control individual catheters of the catheter system 200 including the guide sheath 230, septal crossing catheter 232, and/or implant catheter 236, when present. For example, the catheter modules can include a guide sheath module 1730, a septal crossing catheter module 1732, and/or an implant catheter module 1736.

The catheter stand 1700 can allow for the independent movement of the individual catheters. For example, the guide sheath 230 can be advanced into the heart, for example the right ventricle of a patient when using a right side approach. In some implementations, the catheter stand 1700 can include a guide sheath knob or actuator for advancing and retracting the guide sheath 230. In some implementations, once the guide sheath 230 is in the heart, the guide sheath module 1730 can be positioned in a clamp 1778.

When present, a septal crossing catheter knob 1782, or other septal crossing catheter actuator, on the catheter stand 1700 can be used to advance and retract the septal crossing catheter 232. The septal crossing catheter knob 1782 can be positioned on the distal end of the catheter stand 1700. The septal crossing catheter knob 1782 can advance the septal crossing catheter 232 through the guide sheath, into the right ventricle, and across a ventricular septum into a left ventricle. The septal crossing catheter knob 1782 can be positioned between the septal crossing catheter knob 1782 and the implant catheter knob 1786. When using a left side approach, the septal crossing catheter may not be present.

An implant catheter knob 1786, or other implant catheter actuator, on the catheter stand 1700 can be used to advance and retract the implant catheter 236. The implant catheter knob 1786 can advance the implant catheter 236 through the septal crossing catheter into the left ventricle and to the ventricular wall. The implant catheter knob 1786 can be positioned on the proximal end of the catheter stand 1700. Any of the knobs can advance a catheter of the catheter system 200 when rotated in a first direction. Any of the knobs can retract a catheter of the catheter system 200 when rotated in a direction opposite the first direction. The knobs can be connected to threaded components in threaded holes, such that the knob is advanced or retracted when rotated. The knobs can be connected to the catheters such that the movement of the knobs is translated to movement of the catheters.

The catheter stand 1700, or catheter rack, can control the rotation and depth of each catheter. The catheter stand 1700 can simultaneously move two catheters together while the other catheters are stationary. For example, the septal crossing catheter knob 1782 can be set to advance and retract the guide sheath 230 and the septal crossing catheter 232 simultaneously. In some embodiments, the catheter stand 1700 can simultaneously move any subset of catheters together while other catheters are stationary. The movement of any one of the catheters can be limited by the distance between clamps or actuators.

The catheter delivery system handle can include a module or handle portion for each catheter in the system. For example, the handle can include a guide sheath module 1730, septal crossing catheter module 1732, and implant catheter module 1736. The guide sheath module 1730, septal crossing catheter module 1732, and implant catheter module 1736 can be gripped by clamps 1778 that hold them in place. As described below, a user can control the catheter system 200 by operating handles or actuators on one or more of the catheters modules. Any of the catheters and guidewires described herein can be guided using EDEN, bubble mapping, and/or carbon dioxide mapping. The guide sheath 230, septal crossing catheter 232, and implant catheter 236 can be independently steerable relative to the other catheters.

The handles or actuators can be intuitive such that the user experience resembles actual movement and rotation of the catheters. The user's movement of the handles can be translated into movement of the catheters. In some embodiments, the handles of the catheter stand 1700 can be controlled remotely or automatically. The handles or actuators, for example the guide sheath module 1730 and the septal crossing catheter module 1732, can include one or more vents 1780. The vents 1780 can allow the catheters to be deaired. A user can couple a syringe to a vent 1780 and remove the air from the catheter.

The guide sheath handle or module 1730 can be positioned on a distal portion of the catheter stand 1700. The guide sheath module 1730 can include a flex knob 1731 to control the angle at which the guide sheath 230 bends. The flex knob 1731, or guide sheath flex actuator, can flex the guide sheath 230. The flex knob 1731 can engage a portion of the guide sheath 230. The flex knob 1731 can cause the guide sheath 230 to flex when the flex knob 1731 rotates. The guide sheath module 1730 and flex knob 1731 can be used to advance the guide sheath 230 into the right ventricle. The flex knob 1731 can be used to bend the guide sheath 230 at approximately a 90 degree angle. In some embodiments, the flex knob 1731 can be used to bend the guide sheath 230 at an angle between 45 degrees and 135 degrees. In some embodiments, the flex knob 1731 can be used to bend the guide sheath 230 at an angle between 5 degrees and 175 degrees.

The septal crossing catheter handle or module 1732 can be positioned proximal to the guide sheath module 1730. The septal crossing catheter module 1732 can include a flex knob 1733 to control the angle at which the septal crossing catheter 232 bends. The flex knob 1733, or septal crossing catheter flex actuator, can flex the septal crossing catheter 232. The flex knob 1733 can engage a portion of the septal crossing catheter 232. The flex knob 1733 can cause the septal crossing catheter 232 to flex when the flex knob 1733 rotates. The septal crossing catheter module 1732, septal crossing catheter knob 1782, and flex knob 1733 can be used to advance the septal crossing catheter 232 into the right ventricle. In some embodiments, the septal crossing catheter 232 can be advanced through the guide sheath 230. The septal crossing catheter 232 can be advanced through the ventricular septum, for example using a dilator or piercing member. The flex knob 1733 can be used to bend the septal crossing catheter 232 at approximately a 90 degree angle. In some embodiments, the flex knob 1733 can be used to bend the septal crossing catheter 232 at an angle between 45 degrees and 135 degrees. In some embodiments, the flex knob 1733 can be used to bend the septal crossing catheter 232 at an angle between 5 degrees and 175 degrees.

The septal crossing catheter 232 can pierce the ventricular septum using a dilator. In some embodiments, the dilator can puncture the ventricular septum using RF energy delivered from the dilator. In some embodiments, the septal crossing catheter 232 can puncture the ventricular septum with a needle, screw, or sharp edge. In some embodiments, the ventricular septum can be pierced with a guidewire. The guidewire can be further advanced such that a distal tip is positioned between the epicardium and the pericardium of the ventricular wall.

In some embodiments, the catheter stand 1700 can include a module and knob for guiding a separate anchoring catheter, for example between the septal crossing catheter module 1732 and the implant catheter module 1736. The anchoring catheter module and knob can be similar to the other described modules and knobs. The anchoring coil can be advanced through the septal crossing catheter 232 and/or the guide sheath 230. A non-limiting example of the anchoring catheter is shown in FIGS. 11A and 11B.

The implant catheter handle module 1736 can be positioned proximal to the septal crossing catheter module 1732. An implant catheter knob 1786 that can move the implant catheter 236 distally and proximally. The implant catheter module 1736 and implant catheter knob 1786 can be used to advance the implant catheter 236 through the anchoring catheter, septal crossing catheter 232, and/or the guide sheath 230 into the left ventricle. The implant catheter module 1736 and implant catheter knob 1786 can be used to advance the implant catheter 236 to the ventricular wall. The implant catheter 236 can be positioned such that a distal tip is positioned between the epicardium and the pericardium of the ventricular wall.

In some implementations, the guide sheath 230, the septal crossing catheter 232, and/or the implant catheter 236 can be advanced into the patient with a dilator. In some implementations, the dilator can be removed from the catheter before another catheter is advanced into the patient. In some implementations, the dilator can be removed from the catheter once the catheter is in the desired position.

The implant catheter 236 can include an anchor knob 1792 and a suture knob 1794. The anchor knob 1792, or anchor actuator, can advance an anchor through the implant catheter 236. The anchor knob 1792 can unsheathe the anchor by retracting an outer sheath of the implant catheter 236. In some implementations, the anchor knob 1792 can retract the outer sheath of the implant catheter 236 to expose an anchor, a suture, and/or a hemostasis element. In some embodiments, the anchor knob 1792 can advance, deliver, or release anchors through the implant catheter 236. In some embodiments, the anchor knob 1792 can rotate to advance the anchors without advancing the implant catheter 236, delivering the anchors from the implant catheter 236. In some embodiments, the anchor knob 1792 can move the outer sheath of the implant catheter 236 proximally. The anchor knob 1792 can be used to unsheathe the anchor by advancing the anchor distal to the implant catheter 236. Unsheathing the anchor can lock the suture 1712 in the suture lock of the ventricular septum anchor.

The suture knob 1794, or suture actuator, can tension the suture 1712 in the implant catheter 236. The suture knob 1794 can pull back on the suture 1712 to tension or tighten the suture 1712. The suture 1712 can be tethered to the anchors in the implant catheter. A proximal end of the suture 1712 can be tied or otherwise fixed to a suture hook 1790. The suture hook 1790 can keep the suture 1712 in tension and fixed to a point proximal to the implant catheter.

In some examples, after the suture 1712 is tightened to a desired tension, a cutting catheter can be used to cut the suture proximal to the ventricular septum anchor. A non-limiting example of the cutting catheter is shown in FIGS. 18A-E. In some examples, a pushing catheter can be used to advance the anchors through the implant catheter 236.

In some embodiments, the implant catheter 236 can be advanced to a first ventricular wall location. An anchor can be advanced into the first ventricular wall location through the implant catheter 236 using the anchor knob 1792. The implant catheter 236 can then be advanced to a second ventricular wall location. An anchor can be advanced into the second ventricular wall location through the implant catheter 236 using the anchor knob 1792. The first ventricular wall location and the second ventricular wall location can be between papillary heads or between a mitral annulus and papillary heads. In some embodiments, an anchor can be placed in 1-10 locations in the ventricular wall. The implant catheter 236 can place the ventricular septum anchor after being retracted into the right ventricle. The suture 1712 can be tensioned using the suture knob 1794, the suture lock on the ventricular septum anchor can be locked, and the suture 1712 can be cut using the cutting catheter. Then, the implant catheter 236 can be removed from the patient. In some embodiments, the cutting catheter can cut the suture 1712 after the implant catheter 236 is removed from the patient. The cutting catheter can be advanced through the guide sheath 230.

Figure 18D:
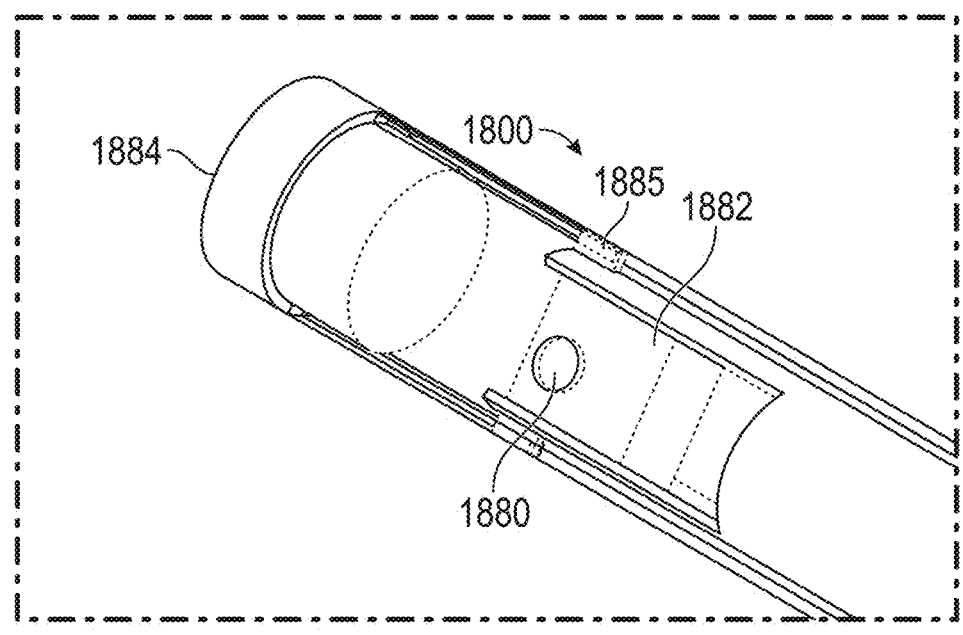
FIG. 18D illustrates a side view of the distal end of the cutting catheter of FIG. 18A with the blade advanced.

FIG. 18A illustrates a transparent view of a distal end of a cutting catheter 1800 with the blade 1882 advanced. FIG. 18B illustrates a transparent perspective view of the distal end of the cutting catheter 1800 of FIG. 18A with a blade 1882 advanced. FIG. 18C illustrates an example of a proximal end of the cutting catheter 1800 of FIG. 18A. FIG. 18D illustrates a side view of the distal end of the cutting catheter

Figure 18E:
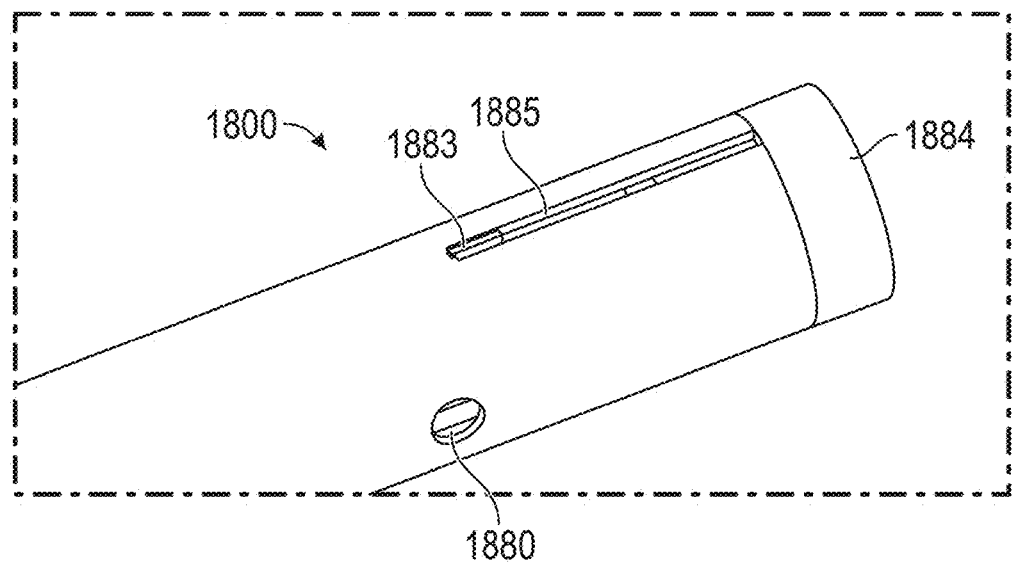
FIG. 18E illustrates a side view of the distal end of the cutting catheter of FIG. 18A with the blade retracted.

1800 of FIG. 18A with the blade 1882 advanced. FIG. 18E illustrates a side view of the distal end of the cutting catheter 1800 of FIG. 18A with the blade 1882 retracted.

The cutting catheter 1800 can include a blade 1882 that can cut a suture once it has been tightened to the desired tension. The suture can be pulled through holes 1880 on either side of the cutting catheter 1800, for example using a snare or guidewire. Before cutting the suture, the blade 1882 can be spring loaded forward toward the distal end. Once the suture is through the holes 1880, the handle 1886 on the proximal end of the cutting catheter 1800 can be used to retract the blade 1882 relative to the rest of the cutting catheter 1800. Pulling on the handle 1886 can pull the blade 1882 toward the suture. The blade 1882 can cut the suture near the proximal end of the suture lock in the right ventricle.

The cutting catheter 1800 can have a stopper 1884 to enhance movement through the vasculature and heart. The cutting catheter 1800 can have a slot 1885 that limits movement of the blade 1882. A portion 1883 of the blade 1882 can move within the slot 1885 while the blade 1882 is being retracted. The cutting catheter 1800 can be operated from the proximal end, as shown in FIG. 18C. The cutting catheter 1800 can be guided using a catheter stand or catheter module. In some implementations, elements of the cutting catheter 1800 may be included in the suture lock. For example, the suture lock may include a blade to cut a suture.

Figure 19A:
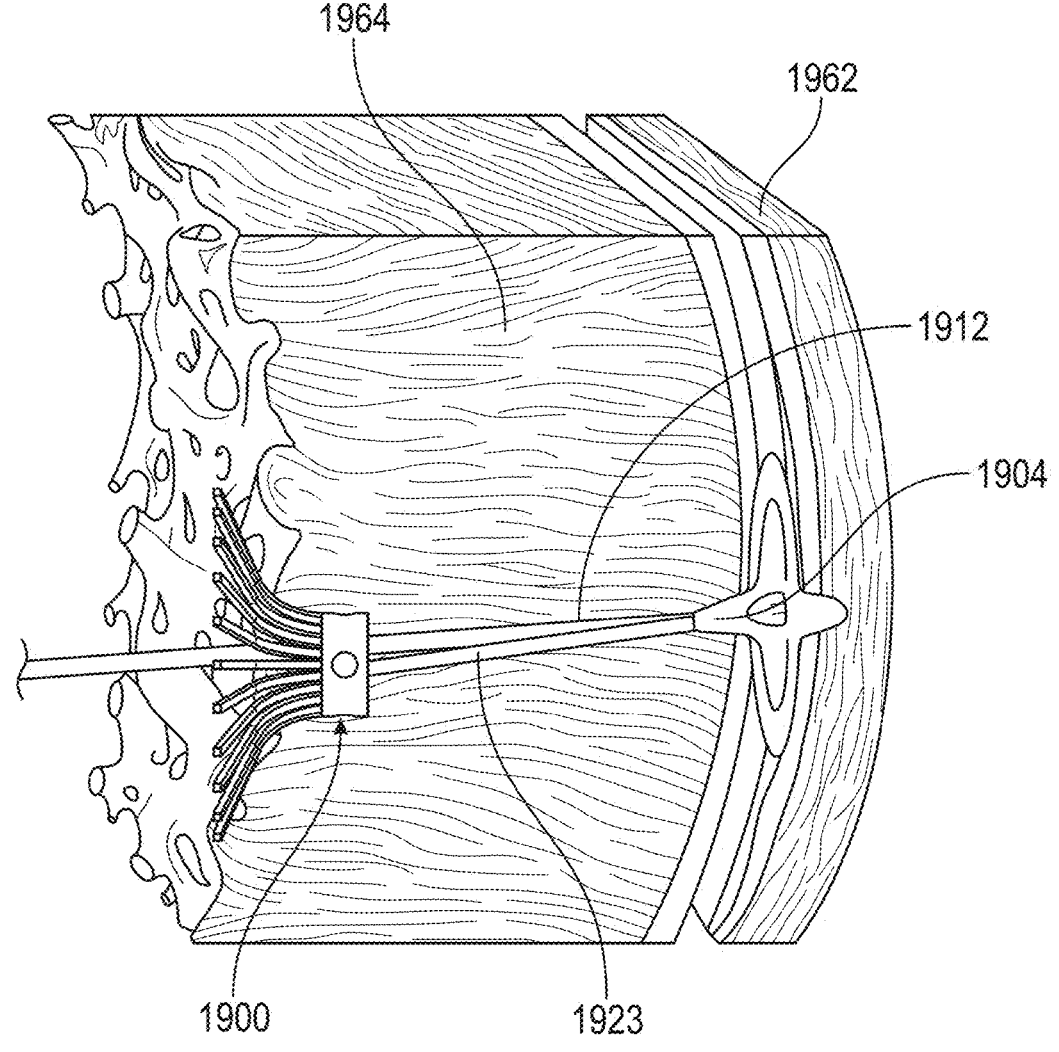
FIG. 19A illustrates an example of a hemostasis element deployed in the myocardium.
Figures 19B, 19C:
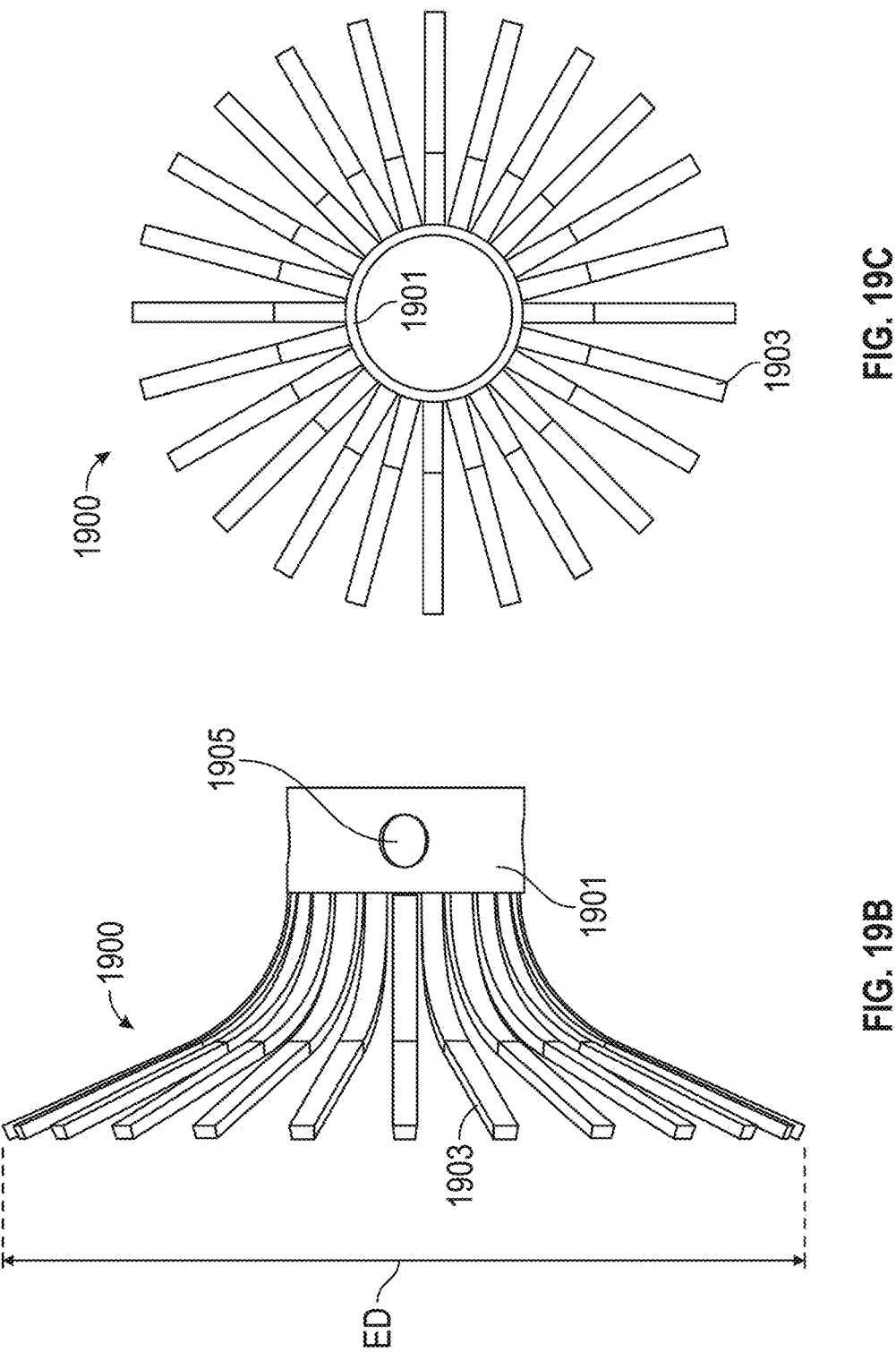
FIG. 19B shows a side view of the example of the hemostasis element of FIG. 19A in an expanded state.
FIG. 19C shows a front view of the example of the hemostasis element of FIG. 19A in an expanded state.
Figure 19D:
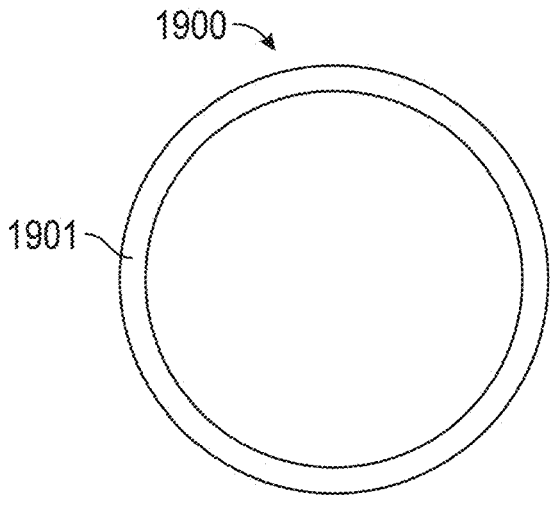
FIG. 19D shows a front view of the example of the hemostasis element of FIG. 19A in a collapsed state.
Figure 19E:
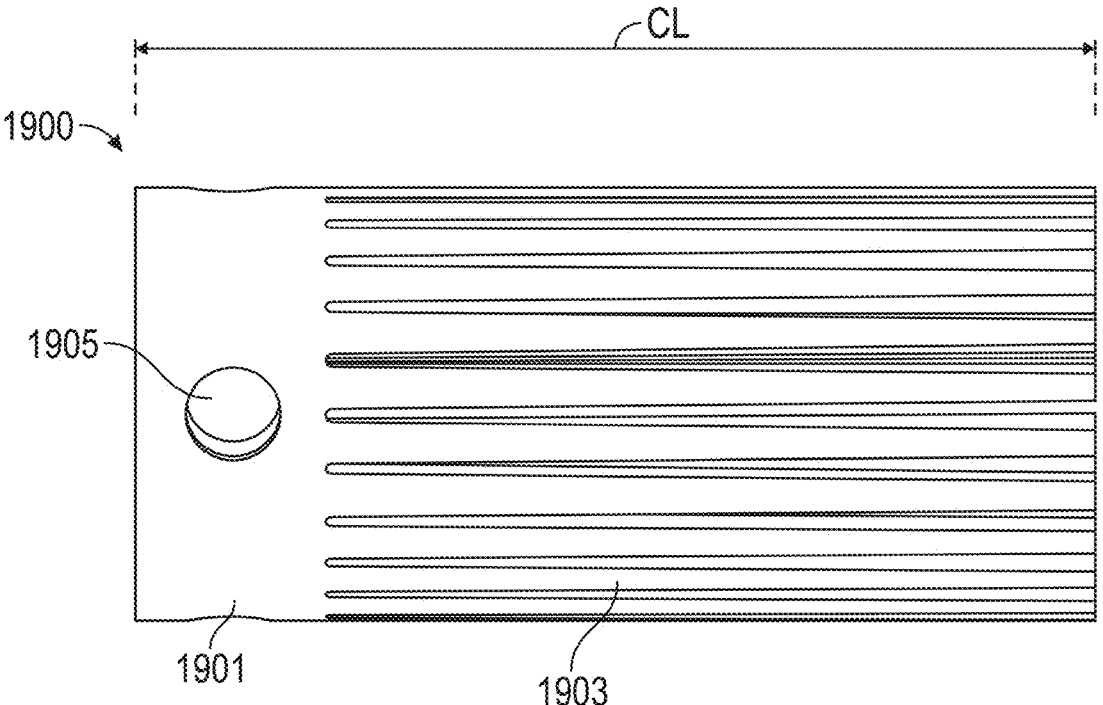
FIG. 19E shows a side view of the example of the hemostasis element of FIG. 19A in a collapsed state.

FIG. 19A illustrates an example of a hemostasis element 1900 deployed in the myocardium. FIG. 19B shows a side view of the example of the hemostasis element 1900 of FIG. 19A in an expanded state. FIG. 19C shows a front view of the example of the hemostasis element 1900 of FIG. 19A in an expanded state. FIG. 19D shows a front view of the example of the hemostasis element 1900 of FIG. 19A in a collapsed state. FIG. 19E shows a side view of the example of the hemostasis element 1900 of FIG. 19A in a collapsed state.

In some implementations, a guidewire can form a passageway in the myocardium 1964 so an anchoring catheter can cross to the space between the myocardium 1964 and the pericardium 1962. In some implementations, when the anchor 1904 is placed between the myocardium 1964 and the pericardium 1962, the anchoring catheter can form the passageway through the myocardium 1964. Forming a tunnel in the myocardium may cause blood to leak through the myocardium 1964 to the space between the myocardium 1964 and pericardium 1962. A hemostasis element 1900 can be used to prevent blood from passing through the passageway into the space between the myocardium 1964 and pericardium 1962. The hemostasis element 1900 can be deployed in the ventricular wall to prevent blood from passing through the ventricular wall. A suture 1923 can be tethered to the anchor 1904 and the hemostasis element 1900. In some examples, the hemostasis element 1900 can be made of nitinol or another self-expanding material. The hemostasis element 1900 can be covered in ePTFE, PET, and/or another soft, biocompatible, conformable material. The hemostasis element 1900 can have a small enough lumen in the distal body 1901 to prevent a significant amount of blood from flowing through the hemostasis element when tethered to the suture 1923. The prongs 1903 can expand to prevent the flow of blood through the tunnel formed in the ventricular wall by expanding to fill the space in the tunnel.

The hemostasis element 1900 can be expandable. The hemostasis element 1900 can be delivered in a collapsed state. The hemostasis element 1900 can be carried by the implant catheter. Once deployed, the hemostasis element 1900 can expand to prevent blood from traversing the myocardium 1964 by expanding to seal the tunnel. The hemostasis element 1900 can be self-expanding. Exposing the hemostasis element 1900 from the implant catheter can cause the hemostasis element 1900 to expand in the passageway. In some implementations, the hemostasis element 1900 can fully expand in the passageway. For example, the hemostasis element 1900 can fully expand at the proximal end of the passageway. In some implementations, the hemostasis element 1900 can partially expand in the passageway. For example, the hemostasis element 1900 can partially expand when embedded further in the myocardium 1964.

The hemostasis element 1900 can include a distal body 1901. In some implementations, the distal body 1901 can have a diameter of at least 0.01 inches and/or less than or equal to 0.1 inches, for example between 0.04 inches and 0.06 inches. The distal body 1901 can include holes 1905. In some implementations, sutures can be tethered to the holes 1905. The hemostasis element 1900 can include one or more prongs 1903. The one or more prongs 1903 may be circumferentially spaced apart from other.

As shown in FIG. 19B, when expanded, the prongs 1903 can extend radially outward to form a conical shape. The one or more prongs 1903 and the space therebetween may be coated with a polymeric material such that the polymeric material forms a substantially continuous surface. When covered with the polymeric material, the hemostasis element 1900 can have an umbrella-like shape. The prongs 1903 may comprise a shape memory material such as nitinol, while the polymeric material can be PTFE, ECTFE, ETFE, FEP, or PFA. In the expanded state, the prongs 1903 can extend to cover a diameter ED of at least 0.05 inches and/or less than or equal to 0.5 inches, for example between 0.1 inches and 0.2 inches.

As shown in FIG. 19E, when collapsed, the prongs 1903 can extend straight, or perpendicular to the distal body 1901. In the collapsed state, the prongs 1903 can extend a length CL of at least 0.01 inches and/or less than or equal to 0.2 inches, for example between 0.05 and 0.15 inches.

The anchor 1904 can have multiple sutures 1912, 1923 tethered to the anchor 1904 for connection to the hemostasis element 1900 and one or more other anchors. In some implementations, one suture can connect the anchor to another anchor and include a hemostasis element. In some implementations, a hemostasis element can be positioned in the septal anchor to prevent blood flow through the septal hole. The septal hemostasis element can be larger than the ventricular hemostasis element.

Figure 20:
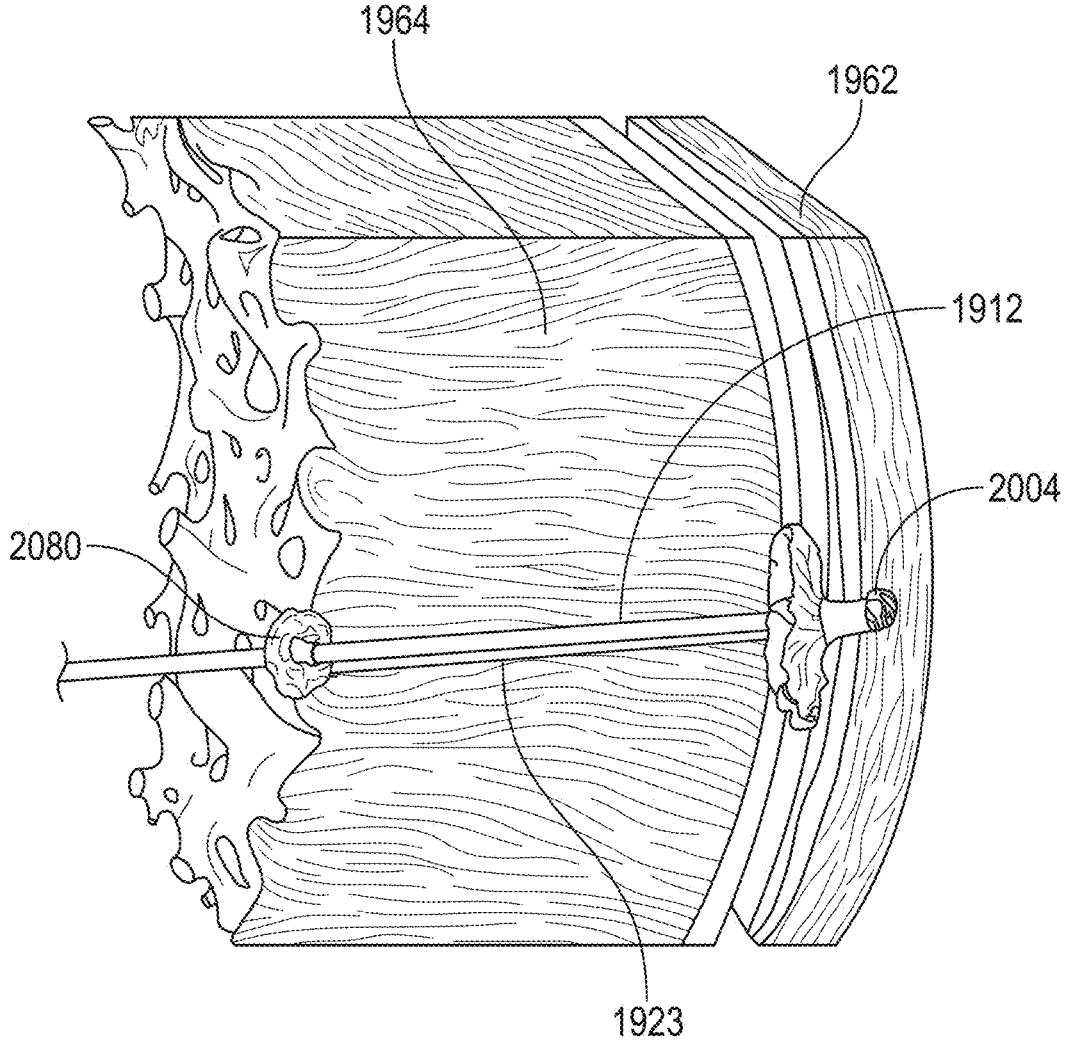
FIG. 20 shows an example of another embodiment of a hemostasis element deployed in the myocardium.

FIG. 20 shows an example of another embodiment of a hemostasis element 2080 deployed in the myocardium.

The anchor 2004 and hemostasis element 2080 can include any of the features of the anchor 1904 and hemostasis element 1900 of FIGS. 19A-E.

The anchor 2004 can engage the pericardial space. Advantageously, the anchor 2004 can provide improved retention force and flexibility. The anchor 2004 can be a low-profile anchor, for example a low-profile 8 Fr anchor. In some examples, the anchor 2004 can have a profile of between 5 Fr and 10 Fr. In some examples, the anchor 2004 can have a profile of between 2 Fr and 15 Fr. The anchor 2004 can have adequate holding force without piercing the pericardium 1962.

The hemostasis element 2080 can be an elliptical member. For example, the hemostasis element 2080 can be circular or ovoid. The hemostasis element 2080 can have a circumference sufficient to prevent blood from entering the tunnel formed in the myocardium 1964 by the implant catheter.

Figure 21A:
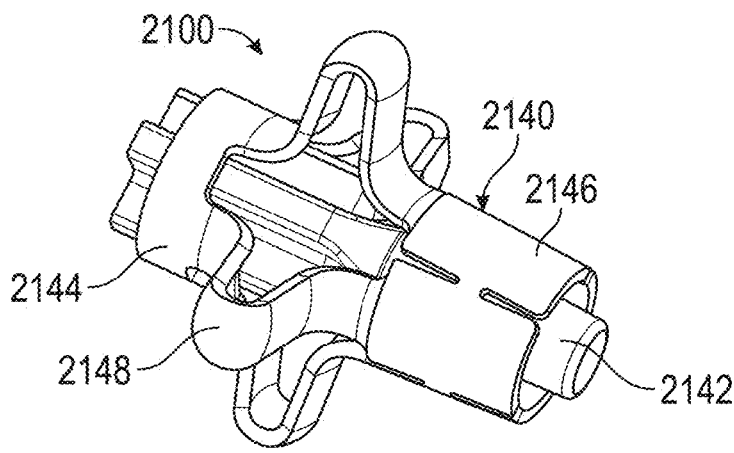
FIG. 21A is a perspective view of an example of a suture lock.
Figure 21B:
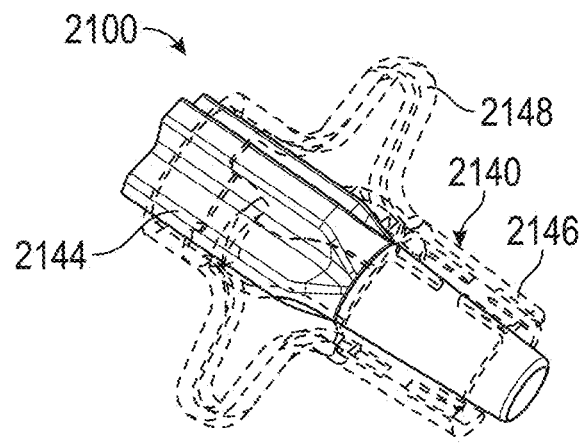
FIG. 21B is a perspective view of the example of the suture lock of FIG. 21A with the sheath transparent.
Figure 21C:
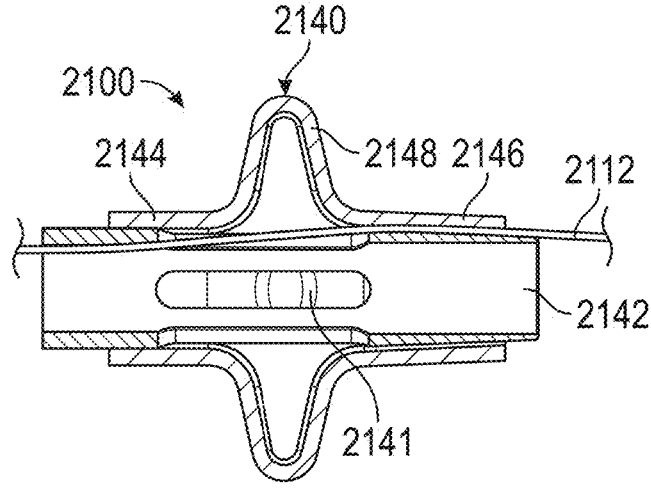
FIG. 21C is a cross-sectional view of the example of the suture lock of FIG. 21A with a suture locked.

FIG. 21A is a perspective view of an example of a suture lock 2100. FIG. 21B is a perspective view of the example of the suture lock 2100 of FIG. 21A with the sheath 2140 transparent. FIG. 21C is a cross-sectional view of the example of the suture lock 2100 of FIG. 21A with a suture 2112 locked.

The suture lock 2100 can include any of the features of the suture locks described with respect to FIGS. 13-15. The suture lock 2100 can be coupled with and/or integrated with an end of an anchor described herein.

The suture lock 2100 can include a sheath 2140 and an inner body 2142. The inner body 2142 can be a tapered pin core. The distal portion 2144 of the sheath 2140 can be fixed to a position on the inner body 2142. The proximal portion 2146 of the sheath 2140 can be moveable along the longitudinal axis of the inner body 2142. The proximal portion 2146 of the sheath 2140 can advance toward the distal portion 2144 when the suture lock 2100 is locked. The suture lock 2100 can be locked by applying tension to the sheath 2140. The suture lock 2100 can be locked when the wings 2148 of the sheath 2140 expand, shortening the distance between the proximal portion 2146 and the distal portion 2144. The proximal portion 2146 of the sheath 2140 can be formed to taper inward such that it conforms to the shape of the inner body 2142. The length of the suture engaged by the suture lock 2100 can be at least 0.5 mm and/or less than or equal to 1 mm. The length of the suture engaged by the suture lock 2100 can be at least 0.1 mm and/or less than or equal to 3 mm. The length of the suture engaged by the suture lock 2100 can be at least 0.05 mm and/or less than or equal to 5 mm. The length of the at least one suture of the plurality of sutures can be locked between an inwardly facing surface of the sheath 2140 and an outwardly facing surface of the inner body 2142.

As shown in FIG. 21C, a suture 2112 can be routed from a lumen of the inner body 2142 to a space radially between the inner body 2142 and the proximal portion 2146 of the sheath 2140. The suture 2112 can be routed through an aperture 2141 in the wall of the inner body 2142. The force between the inner body 2142 and the proximal portion 2146 of the sheath 2140 can lock the suture 2112 in place. Advantageously, the suture 2112 is locked by force applied along a length of the suture 2112 rather than at one point on the suture 2112. This can prevent damage and/or fatigue to the suture 2112. The proximal portion 2146 of the sheath 2140 and the inner body 2142 can have a close fit to prevent the suture 2112 from slipping. The proximal portion 2146 of the sheath 2140 can be formed to the inner body 2142, or pin, during assembly.

In some examples, the suture engagement length, or the length of the proximal portion 2146 of the sheath 2140 along the longitudinal axis, can be at least 0.5 mm. The suture engagement length can be greater than about 0.5 mm and/or less than about 3 mm. The suture engagement length can be greater than about 0.1 mm and/or less than about 5 mm.

Figure 22A:
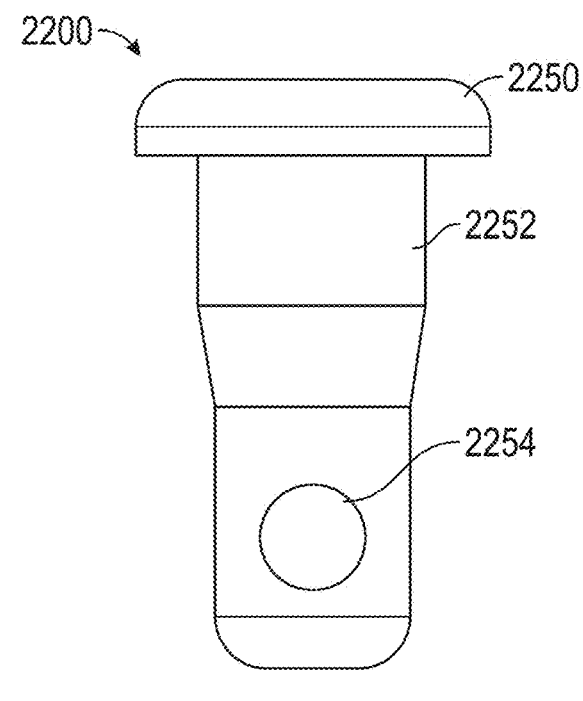
FIG. 22A is a side view of a distal pin for retaining a suture.
Figure 22B:
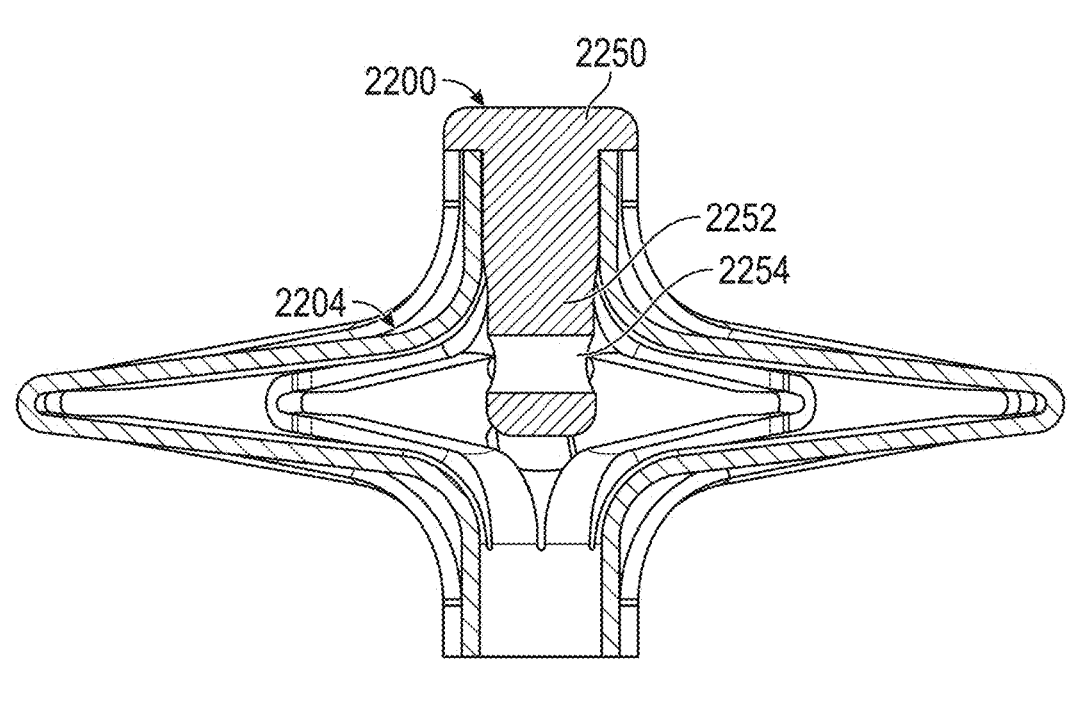
FIG. 22B is a cross-sectional side view of an example of a ventricular anchor coupled and/or integrated with the distal pin of FIG. 22A.

FIG. 22A is a side view of a distal pin 2200. FIG. 22B is a cross-sectional side view of an example of a ventricular anchor 2204 coupled and/or integrated with the distal pin 2200 of FIG. 22A.

The ventricular anchor 2204 can include any of the features of the ventricular anchors 300, 400 of FIGS. 3, and 4A-B.

The distal pin 2200 can include a cap 2250, an elongate body 2252, and an aperture 2254. The aperture 2254 can be formed through the elongate body 2252 orthogonal to the longitudinal axis of the elongate body 2252. The elongate body 2252 can be substantially cylindrical. The elongate body 2252 can taper inward at a mid-section of the elongate body 2252. The aperture 2254 can be near a proximal end of the elongate body 2252 of the distal pin 2200.

As shown in FIG. 22B, the distal pin 2200 can fit into an anchor 2204 such that the cap 2250 seals to a distal end of the anchor 2204 and the elongate body 2252 extends into the anchor 2204. The aperture 2254 can be used to retain a suture. A user can route a suture through the aperture 2254 of the distal pin 2200. Advantageously, when tension is applied to a suture routed through the aperture 2254 of the distal pin 2200, the anchor 2204 can distribute the force to the heart wall or septum without causing the anchor 2204 to invert or hyperextend. The aperture 2254 of the distal pin 2200 can be positioned near the center of the anchor 2204 such that the force from the suture is applied near the center of the anchor 2204.

Figures 23A, 23B:
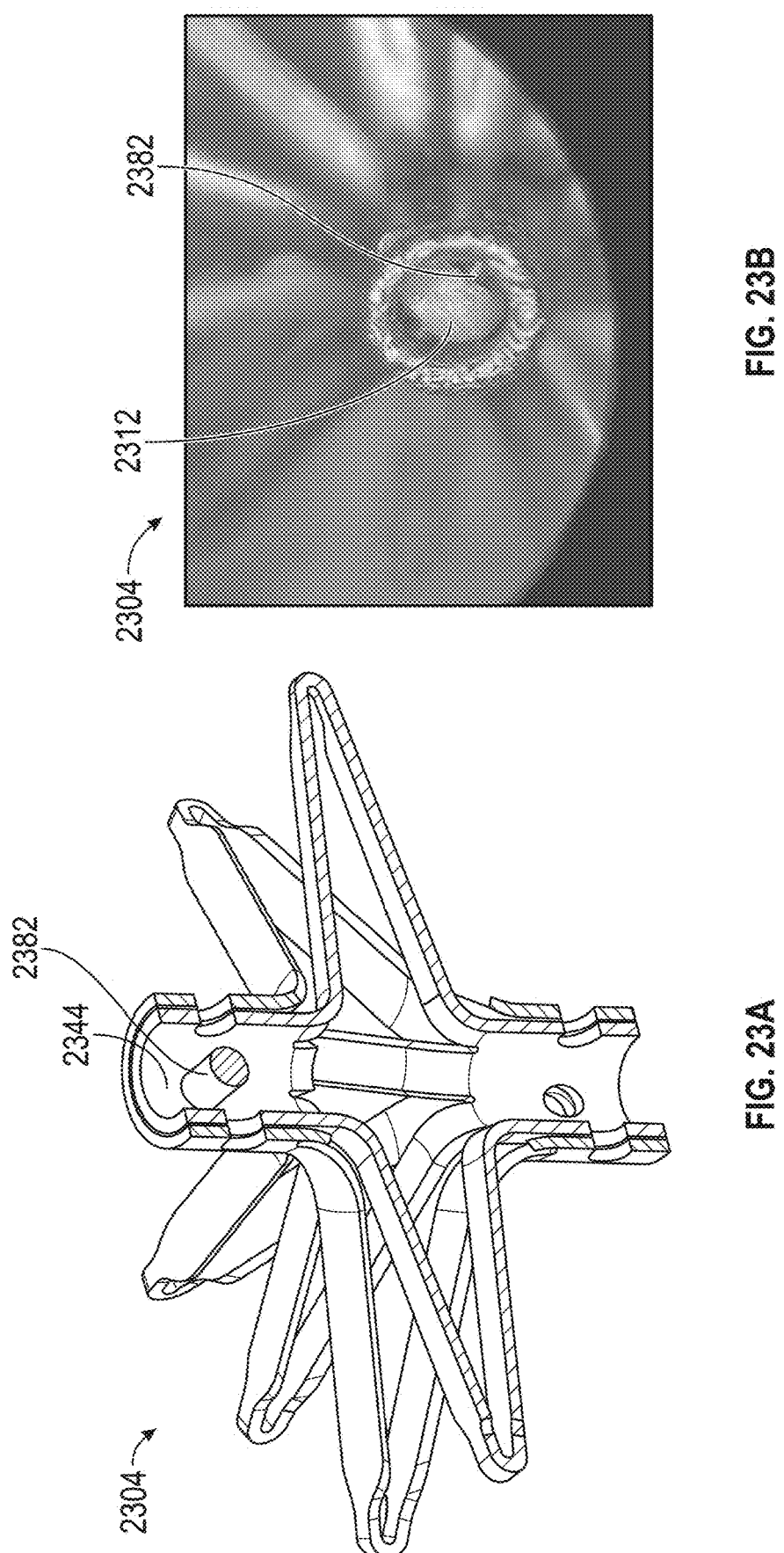
FIG. 23A is a cross-sectional perspective view of an example of a ventricular anchor with a suture crossbar.
FIG. 23B shows an example of a distal end of a ventricular anchor of FIG. 23A with a suture around the suture crossbar.
Figures 23C, 23D:
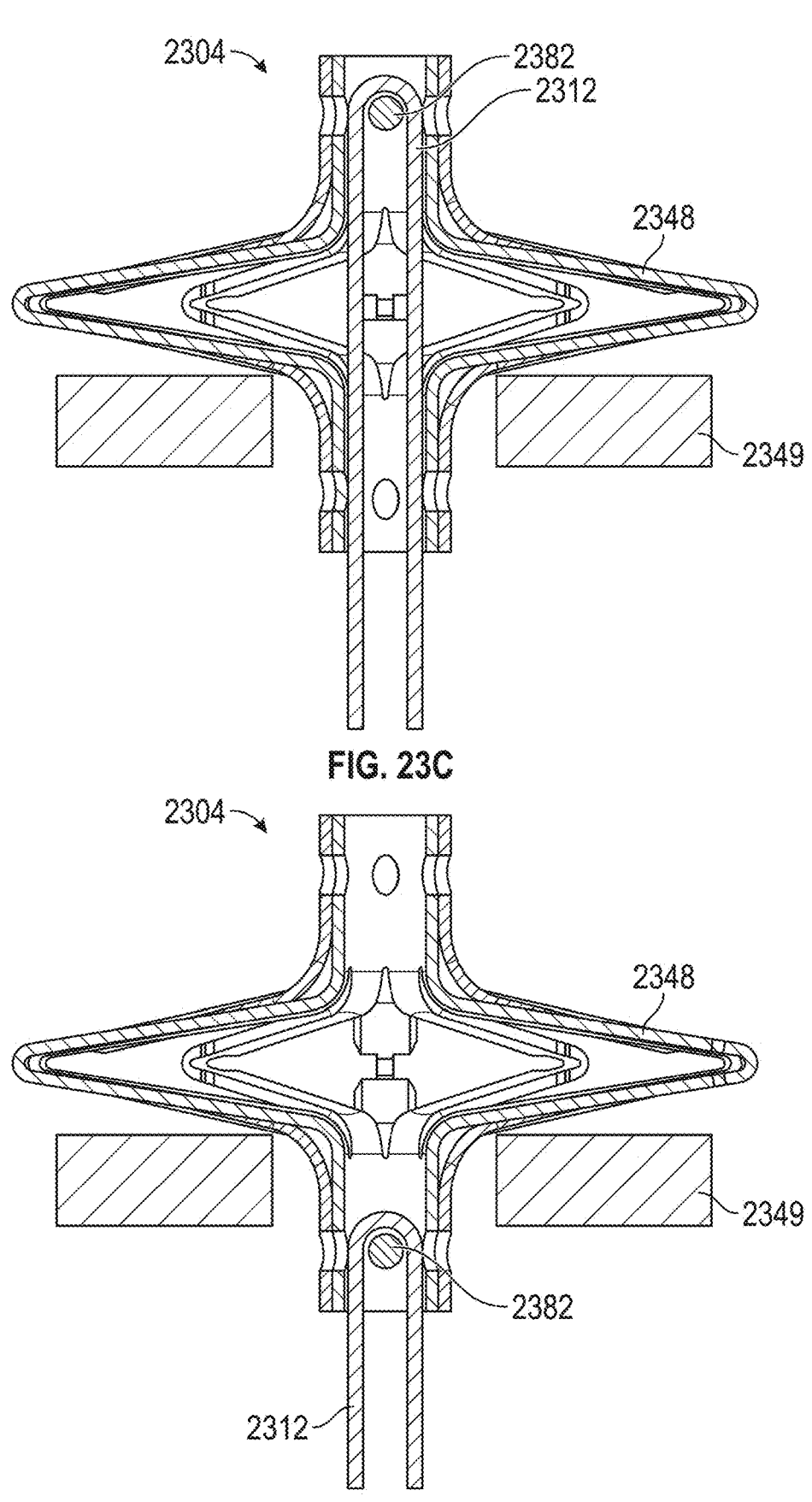
FIG. 23C shows an example of a ventricular anchor of FIG. 23A positioned such that a suture is around the suture crossbar on a distal end.
FIG. 23D shows an example of a ventricular anchor of FIG. 23A positioned such that a suture is around the suture crossbar on a proximal end.

FIG. 23A is a cross-sectional perspective view of an example of a ventricular anchor 2304 with a suture crossbar 2382. FIG. 23B shows an example of a distal end of a ventricular anchor 2304 of FIG. 23A with a suture 2312 around the suture crossbar 2382. FIG. 23C shows an example of a ventricular anchor 2304 of FIG. 23A positioned such that a suture 2312 is around the suture crossbar 2382 on a distal end. FIG. 23D shows an example of a ventricular anchor 2304 of FIG. 23A positioned such that a suture 2312 is around the suture crossbar 2382 on a proximal end.

The ventricular anchor 2304 can include any of the features of the ventricular anchors 300, 400, 2204 of FIGS. 3, 4A-4B, and 22B.

The ventricular anchor 2304 can include a suture crossbar 2382 within the lumen of the inner body 2344. The suture crossbar 2382 can be a bar that extends across the lumen of the anchor 2304. The suture crossbar 2382 can be cylindrical, a rectangular prism, or another elongate shape.

As shown in FIG. 23B, a suture 2312 can be routed around the suture crossbar 2382. Applying tension to the suture 2312 can cause the suture 2312 to apply force to the suture crossbar 2382, which can cause the anchor 2304 to apply force to the heart wall or septum.

As shown in FIG. 23C, the anchor 2304 can be positioned such that the suture crossbar 2382 is on a distal end of the anchor 2304. This can cause the force from the suture to apply to the distal end of the anchor 2304, which distributes the force to the wings 2348. The wings 2248 distribute this force to the tissue 2349. The tissue 2349 can be the heart wall or septum.

As shown in FIG. 23D, the anchor 2304 can be positioned such that the suture crossbar 2382 is on a proximal end of the anchor 2304. This can cause the force from the suture to apply to the proximal end of the anchor 2304, which distributes the force to the wings 2348. The wings 2248 distribute this force to the tissue 2349. The tissue 2349 can be the heart wall or septum.

Figure 24A:
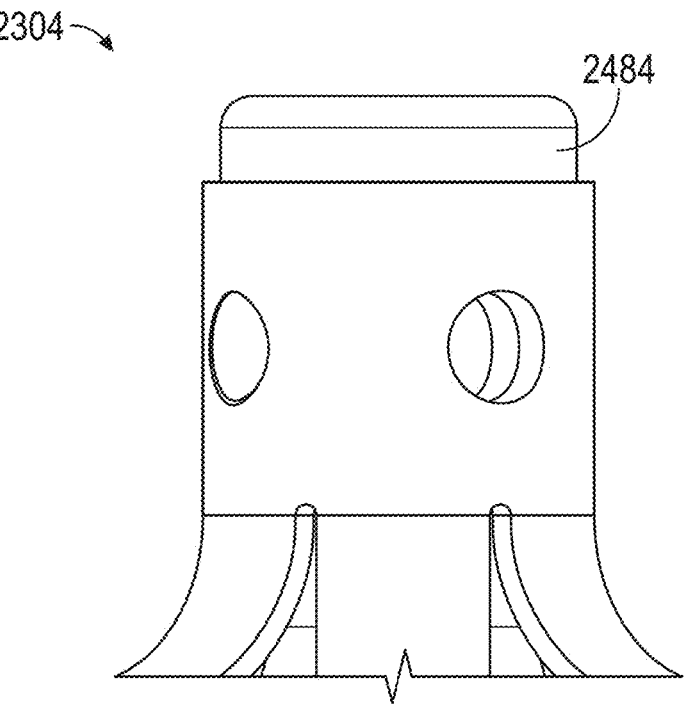
FIG. 24A shows an example of a distal end of a ventricular anchor with an atraumatic tip welded to the ventricular anchor.
Figure 24B:
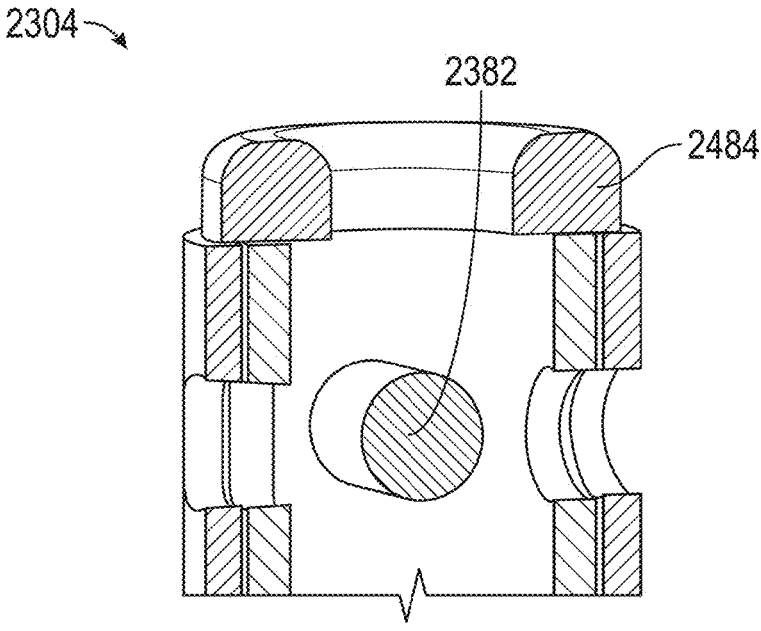
FIG. 24B is a cross-sectional view of the example of the distal end of the ventricular anchor of FIG. 24A with an atraumatic tip welded to the ventricular anchor.

FIG. 24A shows an example of a distal end of a ventricular anchor 2304 with an atraumatic tip 2484 welded to the ventricular anchor 2304. FIG. 24B is a cross-sectional view of the example of the distal end of the ventricular anchor 2304 of FIG. 24A with an atraumatic tip 2484 welded to the ventricular anchor 2304.

The atraumatic tip 2484 can be welded to the distal end of the anchor 2304. In some examples, as shown in FIG. 24B, the tip 2484 can be welded to the side of the anchor 2304 with the suture crossbar 2382. In some examples, the tip 2484 can be welded to the side of the anchor 2304 without the suture crossbar 2382. The tip 2484 can be welded, coupled, or integrated to whichever side will be used as the distal end of the anchor 2304.

The atraumatic tip 2484 can be positioned such that there is space to route a suture between the tip 2484 and the suture crossbar 2382. The atraumatic tip 2484 can have heavy electropolish so it is smooth. The atraumatic tip 2484 can ensure pericardial interaction does not harm the pericardium.

Figure 25A:
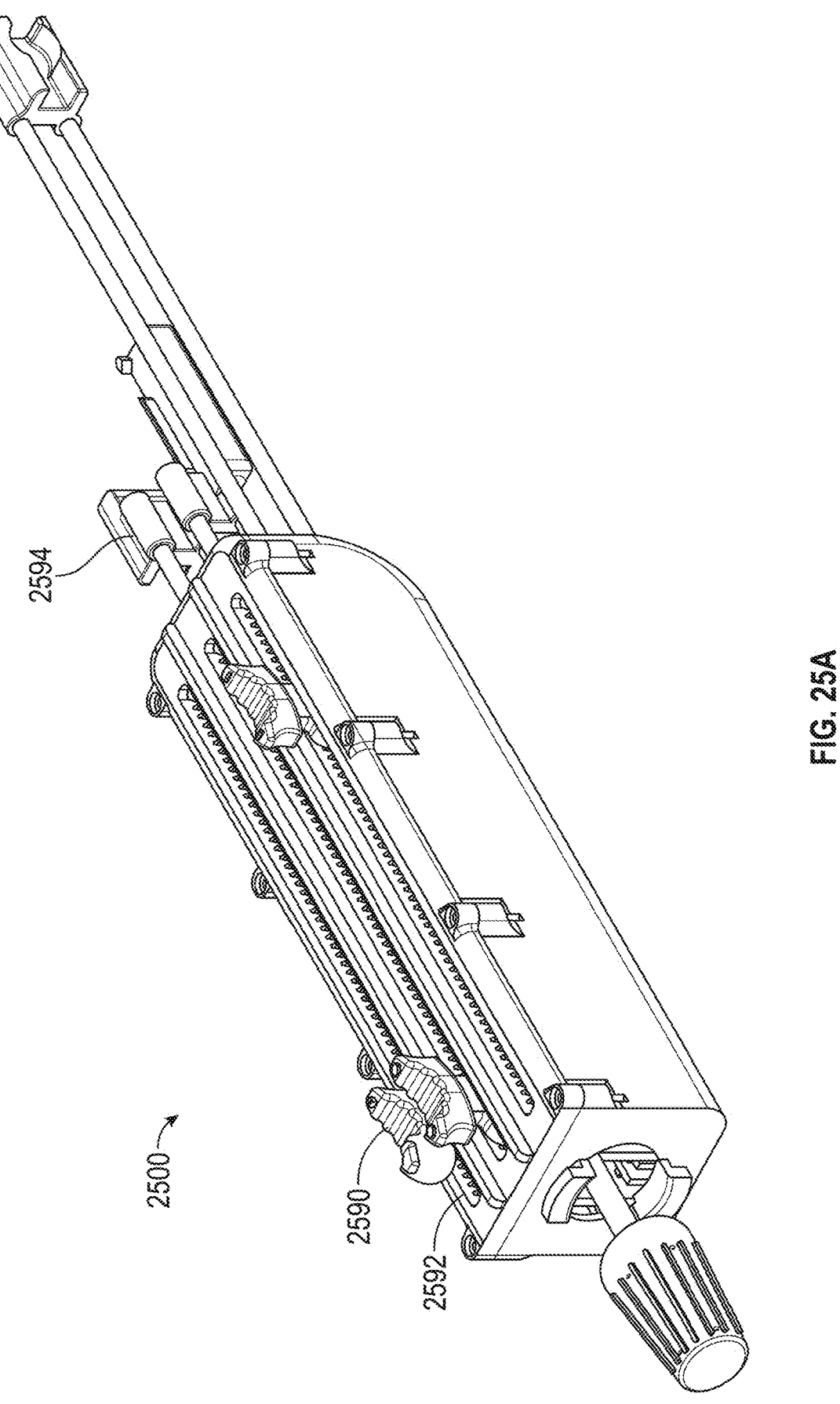
FIG. 25A-C show an example of a suture tensioning handle.
Figure 25B:
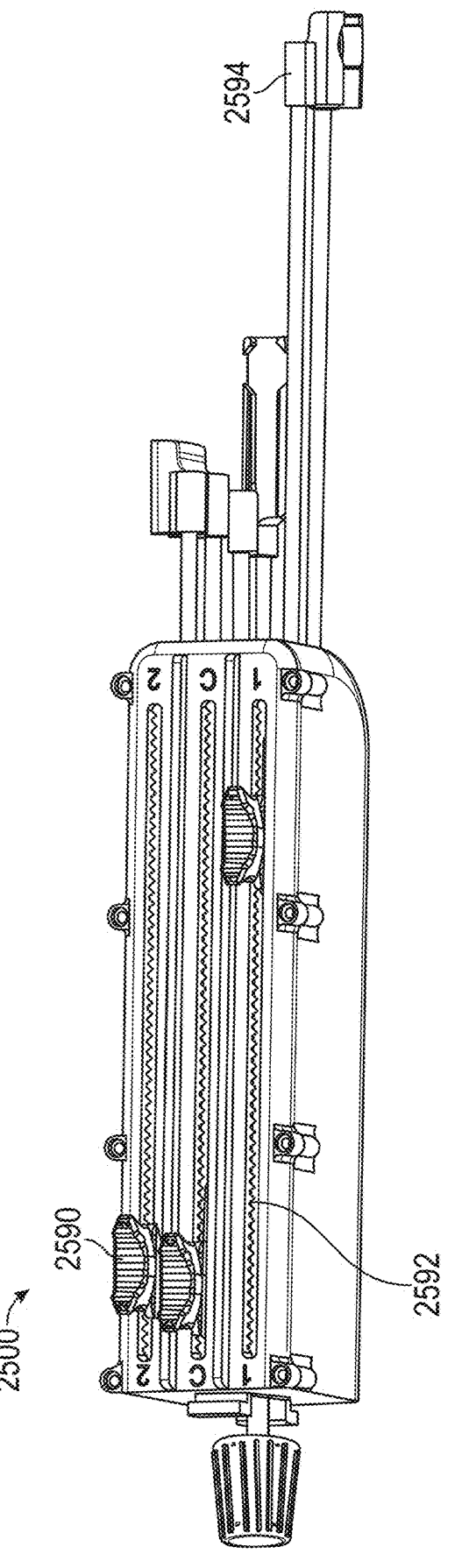
Figure 25C:
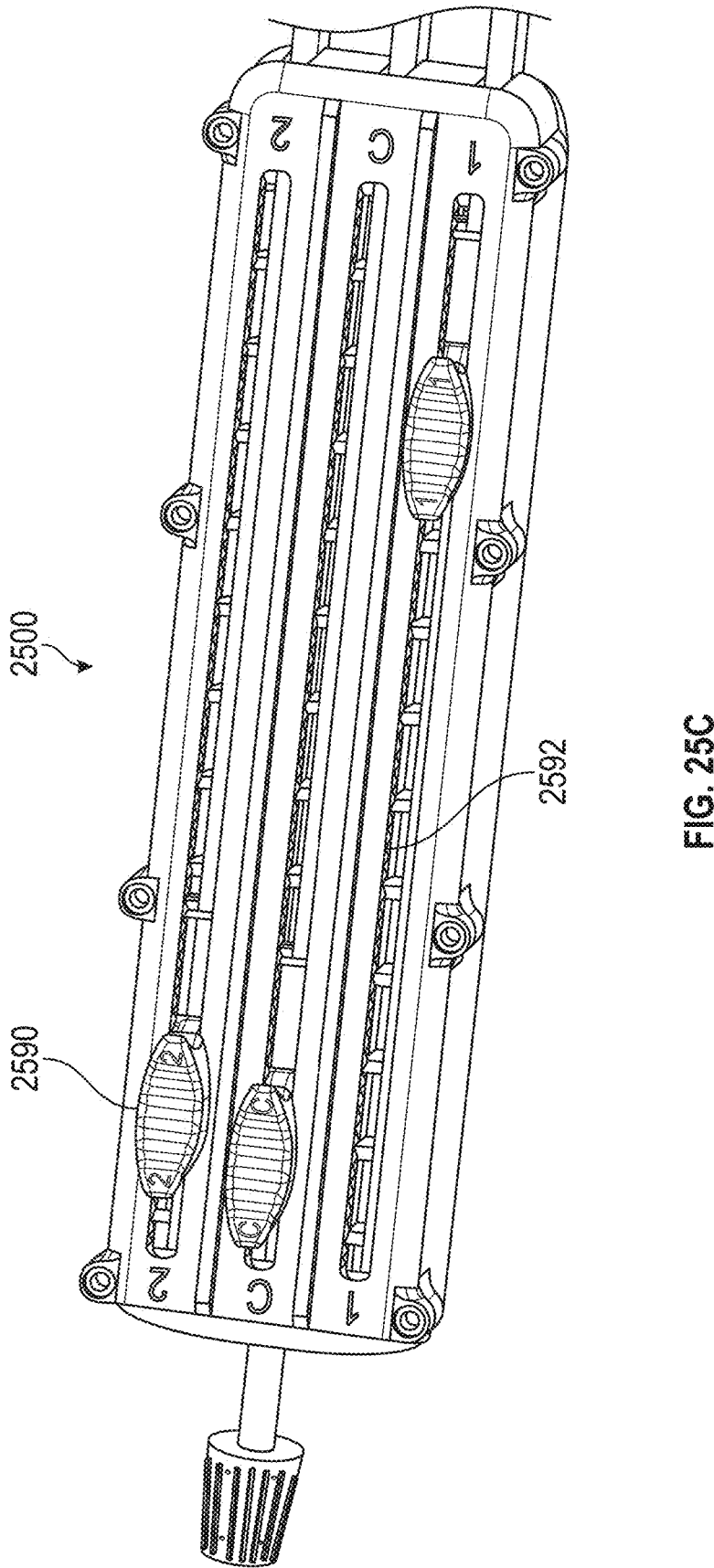

FIG. 25A-C show an example of a suture tensioning handle 2500.

The suture tensioning handle 2500 can include actuators 2590. The actuators 2590 can be knobs, buttons, switches, or levers. The actuators 2590 can be along a groove 2592. As shown, the handle 2500 can have three actuators 2590. In some examples, the handle 2500 can have 1-5 actuators 2590. In some examples, the handle 2500 can have 1-10 actuators 2590.

Each actuator 2590 can be connected to one or more sutures. Using the actuators 2590, the sutures can be independently tensioned. The distance between anchors can be reduced without affecting or significantly affecting other dimensions. Each actuator 2590 can be translated or moved along the groove 2592 or track. In some examples, a user can push the actuator 2590 in toward the groove 2592 to unlock the actuator 2590. The user can pull the actuator 2590 away from the groove 2592 to lock the actuator 2590. Locking and unlocking the actuator 2590 can result from engaging and disengaging a notch within the groove 2592. When the actuator 2590 is unlocked, the actuator 2590 can be moved distally, or advanced, along the groove 2592 to loosen the suture. The actuator 2590 can be moved proximally, or retracted, along the groove 2592 to tighten the suture. Although the actuators 2590 are illustrated as sliders, the actuators 2590 may take on other configurations such as dials, buttons, separate handles, etc.

In some examples, each actuator 2590 can be connected with a suture retainer 2594 at the proximal end of the handle 2500. The suture retainers 2594 can move along with the actuators 2590 such that the sutures are pulled tighter or loosened. The distance from the suture retainers 2594 to the groove 2592 can indicate a tension of the suture.

The suture tensioning handle 2500 can be a part of a catheter handle, for example as described with respect to FIGS. 17A-B. The suture tensioning handle 2500 can be proximal to the implant catheter handle.

Figure 26A:
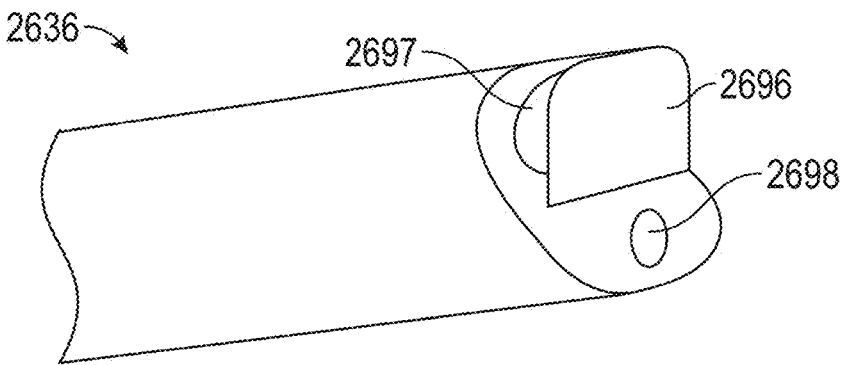
FIG. 26A-C show an example of a lumen cover on an implant catheter.
Figure 26B:
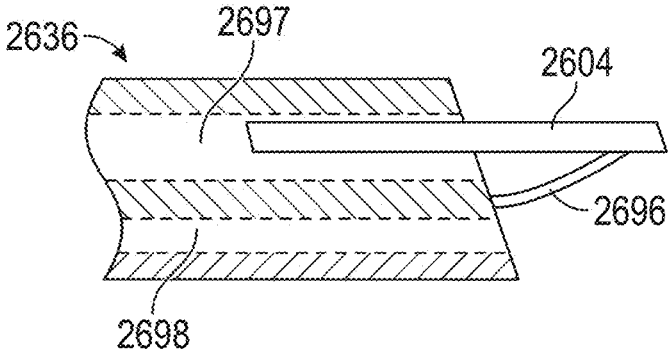
Figure 26C:
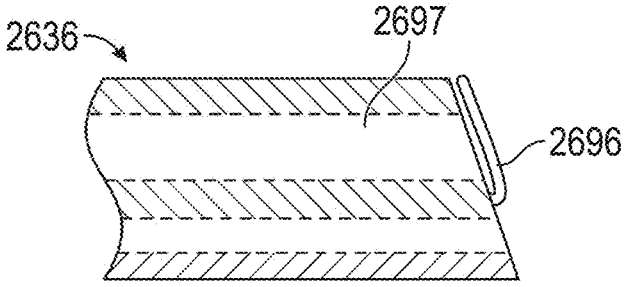

FIG. 26A-C show an example of a lumen cover 2696 on an implant catheter 2636.

The lumen cover 2696 can cover an implant lumen 2697 opening on the implant catheter 2636. The implant catheter 2636 can have a separate guidewire lumen 2698.

The lumen cover 2696 can cover the implant lumen 2697 opening while the implant catheter 2636 is being advanced through the patient's vasculature. Because the implant lumen 2697 has a large opening on the distal end of the implant catheter 2636, the lumen cover 2696 can prevent the opening from coring out tissue.

As shown in FIG. 26B, when an implant 2604 is released from the implant lumen 2697, the lumen cover 2696 can open. Once the implant 2604 is released from the implant lumen 2697, the lumen cover 2696 can close. The lumen cover 2696 may be pivotable such that it can be opened from the force of the implant 2604 being released. The lumen cover 2696 may be biased to the closed position such that it closes once the implant 2604 is released.

FIG. 27 shows an example of a ventricular anchor 2704 covered with a coating 2748.

The ventricular anchor 2704 can be similar to the ventricular anchors described herein, for example with respect to FIG. 3B. The ventricular anchor 2704 can be at least partially covered with a coating 2748. For example, coating 2748 can be a cloth coating. The coating 2748 can conform to the shape of the ventricular anchor 2704. The coating 2748 can prevent damage to the surrounding tissue.

FIG. 28 shows an example of a ventricular septum anchor 2802 covered with a coating 2848.

The ventricular septum anchor 2802 can be similar to the ventricular septum anchors described herein, for example with respect to FIG. 3A. The ventricular septum anchor 2802 can be at least partially covered with a coating 2848. For example, the coating 2848 can be a cloth coating. The coating 2848 can conform to the shape of the ventricular septum anchor 2802. The coating 2848 can prevent damage to the surrounding tissue. The suture lock can be at least partially exposed from the coating 2848.

FIG. 29A shows an example of a ventricular anchor 2904 with a hemostasis element 2937. FIG. 29B shows the example of the ventricular anchor 2904 of FIG. 29A with the hemostasis element 2937 bent inward.

The ventricular anchor 2904 can be similar to other ventricular anchors described herein. The hemostasis element 2937 can be a plurality of arms that extend from the proximal end of the ventricular anchor 2904. Each arm of the hemostasis element 2937 can include a tab 2938 on the distal end of the arm. The hemostasis element 2937 can collapse radially inward to be delivered through the implant catheter. The hemostasis element 2937 can expand radially outward when released from the implant catheter. The hemostasis element 2937 can contact the inner surface of the heart wall to stabilize the position of the ventricular anchor 2904. The hemostasis element 2937 can contact the inner surface of the heart wall to prevent blood from leaking around the ventricular anchor 2904 through the heart wall by keeping the incision in the heart wall small.

As shown in FIG. 29A, the hemostasis element 2937 can be biased toward a configuration in which the arms are curved with the tabs 2938 contacting the inner surface of the heart wall. As shown in FIG. 29B, the hemostasis element 2937 can be biased toward a configuration in which the arms are bent inward. The hemostasis element 2937, in the expanded state, can be bent such that a portion of each arm contacts the inner surface of the heart wall. The arms of the hemostasis element 2937 can engage the heart wall to prevent blood from leaking around the ventricular anchor 2904.

FIG. 30A shows an example of an anchor cap 3050 for routing a suture. FIG. 30B shows a cross-sectional view of the example of the anchor cap 3050 of FIG. 30A.

The anchor cap 3050 can be positioned on a distal end of a ventricular anchor 3004. The ventricular anchor 3004 can be similar to the ventricular anchors described herein, for example with respect to FIGS. 3B, 4A-C, 27, 28, and 29. The anchor cap 3050 can be used to route a suture across a distal end of the ventricular anchor 3004.

The anchor cap 3050 can include protrusions 3055 on at least one side of the anchor cap 3050. The protrusions 3055 can be configured to deform as the anchor cap 3050 is being positioned in the distal end of the ventricular anchor 3004. The protrusions 3055 can fit within apertures 3056 in the side of the ventricular anchor 3004 to lock the anchor cap 3050 in place.

The anchor cap 3050 can include openings 3054 on either side of the anchor cap 3050. The suture can be routed through each opening 3054. The suture can be routed from within the ventricular anchor 3004, through one opening 3054 to the outside of the ventricular anchor 3004, across the anchor cap 3050, and into the opening 3054 on the other side of the anchor cap 3050. Two ends of the suture can extend through the ventricular anchor 3004 and to a suture routing mechanism or another anchor. The suture can apply force across a diameter of the anchor cap 3050. Advantageously, this distribution of force can allow the anchor 3004 to be securely pulled via tension and can avoid fraying of the suture.

The anchor cap 3050 can include a distal opening 3057. The distal opening 3057 can allow the ventricular anchor 3004 to be delivered over a wire. The wire can pass through the ventricular anchor 3004 and extend through the distal opening 3057. The ventricular anchor 3004 can be pushed along the wire.

FIG. 31A shows an example of an anchor cap 3150 with a suture 3112 routed across the anchor cap 3150. FIG. 31B shows a side view of the example of the anchor cap 3150 with a suture 3112 routed across the anchor cap 3150 of FIG. 31A with a wire 3138 extending from the distal end. FIG. 31C shows another side view of the example of the anchor cap 3150 with a suture 3112 routed across the anchor cap 3150 of FIG. 31A with a wire 3138 extending from the distal end.

The anchor cap 3150 can be similar to the anchor cap 3050 of FIGS. 30A-B. The suture 3112 can extend from each side of the anchor cap 3150 and be wrapped around the distal end of the anchor cap 3150. The anchor can be delivered over the wire 3138. The wire 3138 can extend through the distal end of the anchor cap 3150 without interfering with the suture 3112.

FIG. 32 shows an example of a ventricular anchor 3200 for delivery over a wire 3238.

The ventricular anchor 3200 can be similar to the ventricular anchors described herein, for example with respect to FIGS. 3B, 4A-C, 27, 28, 29, and 30A-B. The ventricular anchor 3200 can include wings 3240.

A suture 3212 can extend through a lumen of the ventricular anchor 3200. The ventricular anchor 3200 can include a tube 3261 inside the lumen of the ventricular anchor 3200. In some examples, the tube 3261 can be a nitinol hypotube. The wire 3238, for example a guidewire, can extend through the lumen of the ventricular anchor 3200 and/or through the tube 3261. At the distal opening 3257 of the ventricular anchor 3200, the ventricular anchor 3259 can include members 3259 configured to retain the wire 3238. The members 3259 can block at least part of the distal opening 3257. The suture 3212 can be retained radially outside of the wire 3238. The ventricular anchor 3200 can include jaws 3259 configured to retain the wire 3238 at the distal end of the ventricular anchor 3200.

In some examples, the opening in the distal jaws 3259 can be approximately 0.85 mm. In some examples, the opening in the distal jaws 3259 can be at least 0.5 mm and/or less than or equal to 1 mm. In some examples, the opening in the distal jaws 3259 can be at least 0.25 mm and/or less than or equal to 1.5 mm. In some examples, the inner diameter of the anchor lumen can be approximately 1 mm. In some examples, the inner diameter of the anchor lumen can be at least 0.5 mm and/or less than or equal to 1.5 mm. In some examples, the inner diameter of the anchor lumen can be at least 0.25 mm and/or less than or equal to 2 mm. In some examples, the inner diameter of the tube 3261 can be approximately 0.5 mm. In some examples, the inner diameter of the tube 3261 can be at least 0.25 mm and/or less than or equal to 1 mm. In some examples, the inner diameter of the tube 3261 can be at least 0.1 mm and/or less than or equal to 1.5 mm. In some examples, the wire 3238 can have a diameter of approximately 0.4 mm. In some examples, the wire 3238 can have a diameter of at least 0.1 mm and/or less than or equal to 1 mm.

FIG. 33A shows an example of an anchor 3300 with bearing balls 3363 disposed around a guidewire 3328. FIG. 33B shows the example of an anchor 3300 with bearing balls 3363 of FIG. 33A with the guidewire removed.

The ventricular anchor 3300 can be similar to the ventricular anchors described herein, for example with respect to FIGS. 3B, 4A-C, 27, 28, 29, 30A-B, and 32.

The bearing balls 3363 can retain the ventricular anchor 3300 against the wire 3328. The bearing balls 3363 can be disposed on or in a guidewire lumen. As the wire 3328 is pushed through, the bearing balls 3363 can interfere with the implant, or ventricular anchor 3300. The bearing balls 3363 can keep the ventricular anchor 3300 from being deployed unintentionally. When the wire 3328 is removed, the bearing balls 3363 can move closer together, for example being biased radially inward. When the wire 3328 is removed, the ventricular anchor 3300 can be released due to the movement of the bearing balls 3363. For example, a retainer can keep the anchor from being released until the bearing balls 3363 move toward the central axis due to the removal of the wire 3328. In some examples, the bearing balls 3363 can roll as the wire 3328 moves proximally or distally to allow movement of the wire 3328 while restricting movement of the ventricular anchor 3300. The bearing balls can be retained against a wall 3336. The wall 3336 radially outward of the bearing balls 3363 can be a catheter wall, for example an implant catheter wall.

Figures 34A, 34B, 34C, 35:
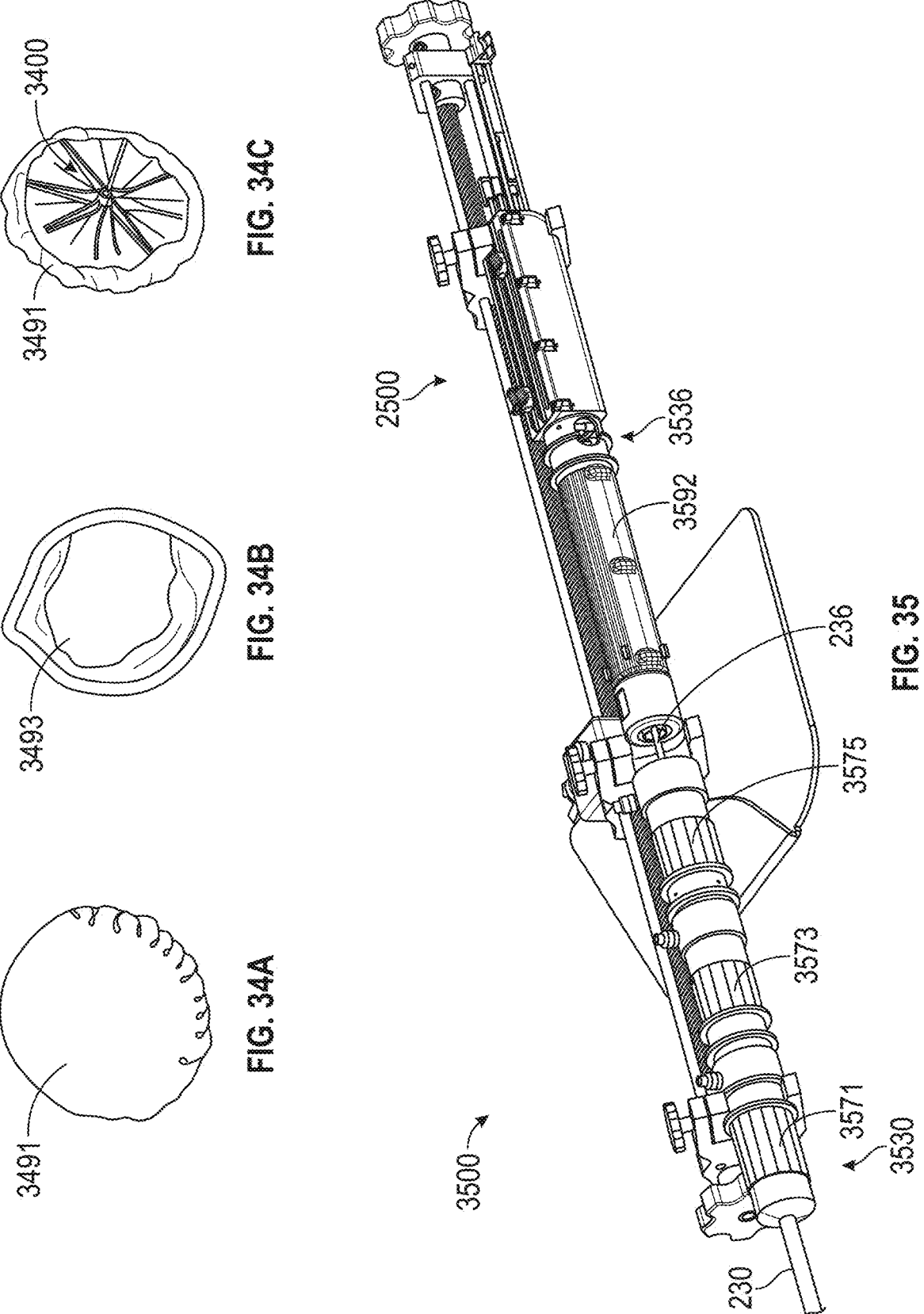
FIG. 34A shows an example of a septal pad for use with a septal anchor.
FIG. 34B shows another example of a septal pad for use with a septal anchor.
FIG. 34C shows the example of the septal pad of FIG. 34A in use with the septal anchor.
FIG. 35 shows an example of a catheter stand for guiding a right ventricular catheter system.

FIG. 34A shows an example of a septal pad 3491 for use with a septal anchor. FIG. 34B shows another example of a septal pad 3493 for use with a septal anchor. FIG. 34C shows the example of the septal pad 3491 of FIG. 34A in use with the septal anchor 3400.

The septal pad 3491, 3493 can increase the holding force of the septal anchor 3400. The septal anchor 3400 can be disposed at or near the center of the septal pad 3491, 3493. The septal pad 3491, 3493 can be expandable. In some examples, the septal pad 3491 can be a shape memory ring covered in polymer mesh. In some examples, the septal pad 3491 can be a nitinol ring covered in ePTFE mesh. In some examples, the septal pad 3493 can be made out of pericardium.

FIG. 35 shows an example of a catheter stand 3500 for guiding a right ventricular catheter system.

The catheter stand 3500 can be similar to the catheter stand 1700 described with respect to FIGS. 17A-B. The catheter stand 3500 and catheter modules can stabilize a catheter system while enabling controlled and independent movement of one or more catheters in the catheter system. The catheter stand 3500 and catheter modules can be positioned at a proximal end of the catheter system. The catheter stand 3500 can include the suture handle 2500 described with respect to FIGS. 25A-C.

The catheter stand 3500 can include one or more clamps to secure one or more of the catheter modules. For example, the catheter stand 3500 can include a separate clamp for each of one or more catheter modules. The catheter modules can control individual catheters of the catheter system 200 including the guide sheath 230 and/or implant catheter 236. The catheter stand 3500 can include a guide sheath module 3530. The guide sheath knob 3571, or access sheath knob, can control movement of the guide sheath 230. The right ventricular guide sheath knob 3573 can be used to bring the distal end of at least one catheter of the catheter system 200 perpendicular to the septal wall. The septal crossing catheter knob 3575 can control movement of the septal crossing catheter 232. The implant catheter knob 3592 can control movement of the implants through the implant catheter 236.

Figure 36A:
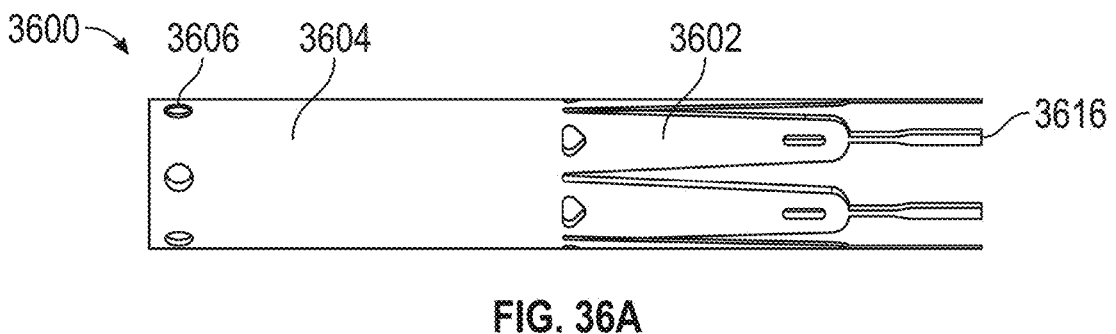
FIG. 36A shows an example of a capsule configured to be mounted on a distal end of the implant catheter.
Figure 36B:
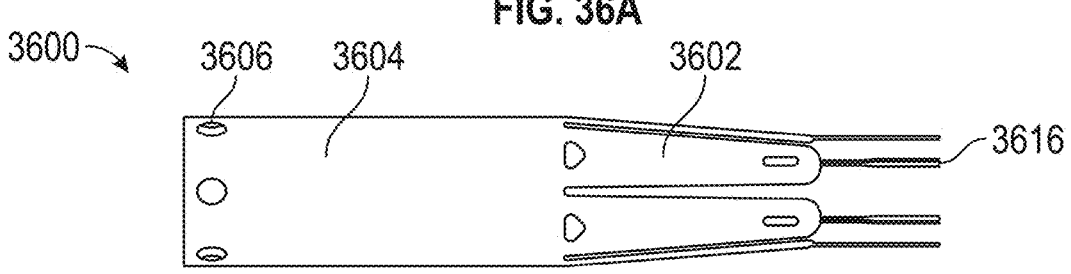
FIG. 36B shows the example of the capsule of FIG. 36A with the distal portion partially closed.
Figure 36C:
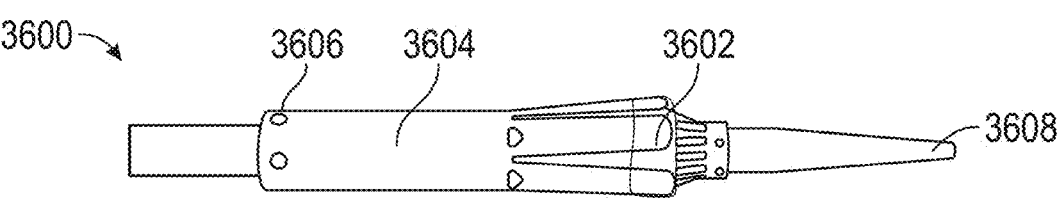
FIG. 36C shows the example of the capsule of FIG. 36A with a rigid tip.
Figure 36D:
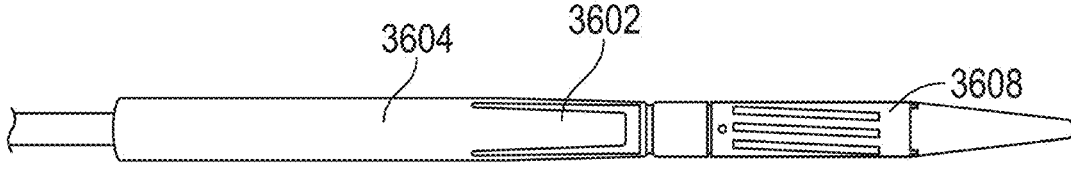
FIG. 36D shows the example of the capsule of FIG. 36A with a rigid tip and an implant.
Figure 36E:
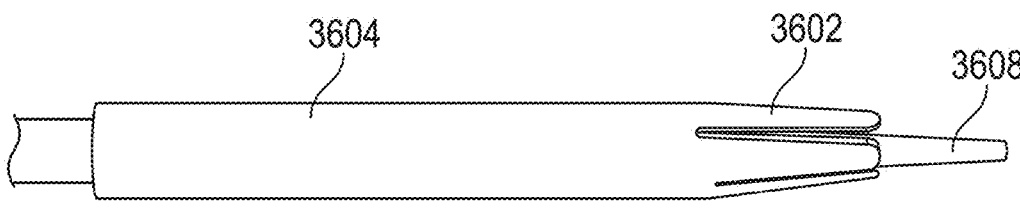
FIG. 36E shows the example of the capsule of FIG. 36A with a rigid tip and the distal portion of the capsule partially closed.
Figure 36F:
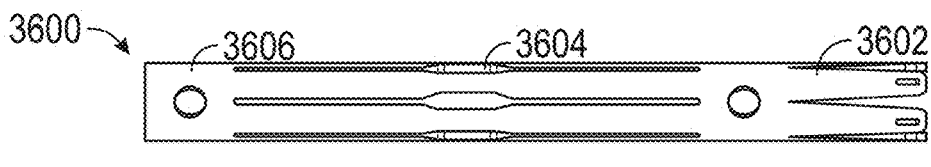
FIG. 36F shows an example of the capsule of FIG. 36A with slits in the implant home portion.
Figure 36G:
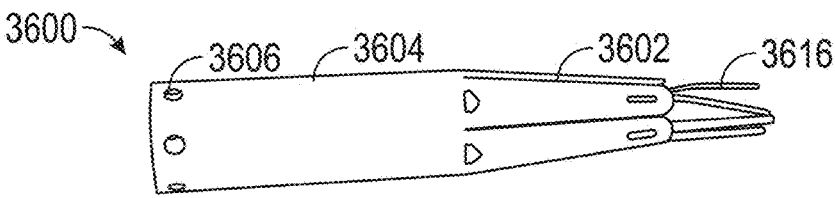
FIG. 36G shows the example of the capsule of FIG. 36A with the distal portion further closed.

FIG. 36A shows an example of a capsule 3600 configured to be mounted on a distal end of the implant catheter. FIG. 36B shows the example of the capsule 3600 of FIG. 36A with the distal portion 3602 partially closed. FIG. 36C shows the example of the capsule 3600 of FIG. 36A with a rigid tip 3608. FIG. 36D shows the example of the capsule 3600 of FIG. 36A with a rigid tip 3608 and an implant 3610. FIG. 36E shows the example of the capsule 3600 of FIG. 36A with a rigid tip 3608 and the distal portion 3602 of the capsule 3600 partially closed. FIG. 36F shows an example of the capsule 3600 of FIG. 36A with slits 3614 in the implant home portion 3604. FIG. 36G shows the example of the capsule 3600 of FIG. 36A with the distal portion 3602 further closed.

The capsule 3600 can be mounted at the distal end of the implant catheter to open and close to allow the implants to be retained or released. The capsule 3600 can be made of a shape memory material. In some examples, the capsule 3600 can be made of nitinol. In some examples, the capsule 3600 can be made of steel, or stainless steel. The capsule 3600 can include a rigid tip 3608 to allow the implant catheter to navigate a bend in the dilator core. The capsule 3600 can include a distal portion 3602 configured to open and close. The distal portion 3602 can be tapered. The capsule 3600 can include an implant home portion 3604. The capsule 3600 can include a mount portion 3606 configured to allow the capsule 3600 to mount to the implant catheter. The capsule 3600 can include slits 3614 in the implant home portion 3604 as shown in FIG. 36F. As shown in FIG. 36G, the distal portion 3602 of the capsule 3600 can include nested and twisted fingers 3616. The fingers 3616 can help retain the implant.

The outer diameter of the capsule 3600 can be approximately 5 mm. In some examples, the outer diameter of the capsule 3600 can be at least 2 mm and/or less than or equal to 8 mm. In some examples, the outer diameter of the capsule 3600 can be at least 1 mm and/or less than or equal to 10 mm. The inner diameter of the capsule 3600 can be approximately 4.7 mm. In some examples, the inner diameter of the capsule 3600 can be at least 4.6 mm and/or less than or equal to 4.8 mm. In some examples, the inner diameter of the capsule 3600 can be at least 4.5 mm and/or less than or equal to 5 mm. In some examples, the inner diameter of the capsule 3600 can be at least 2 mm and/or less than or equal to 7 mm. The capsule 3600 can have a length of approximately 23.5 mm. In some examples, the capsule 3600 can have a length of at least 20 mm and/or less than or equal to 30 mm. In some examples, the capsule 3600 can have a length of at least 10 mm and/or less than or equal to 40 mm.

Figure 37:
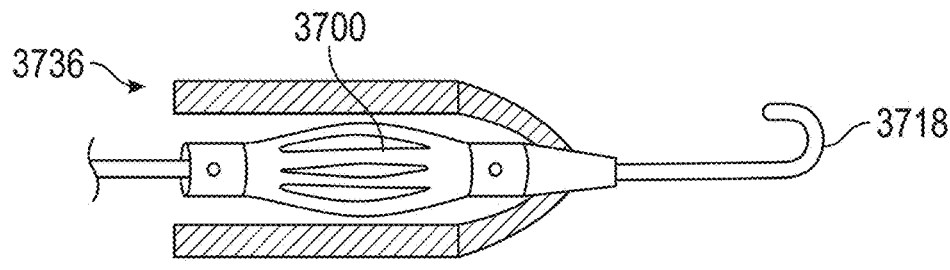
FIG. 37 shows an implant catheter with a tapered tip.

FIG. 37 shows an implant catheter 3736 with a tapered tip 3637.

An implant 3700 can be delivered through the implant catheter 3736 over a wire 3718. The wire 3718 can extend past the distal end of the tapered tip 3637.

Figure 38A:
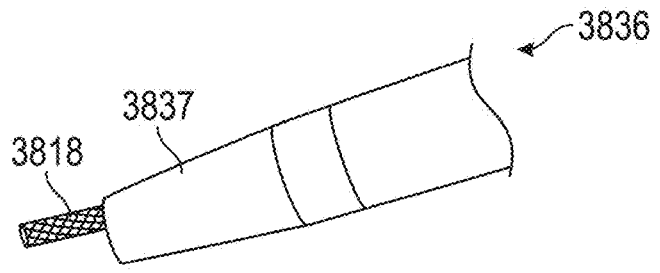
FIG. 38A-38B show an example of a distal tip of an implant catheter.
Figure 38B:
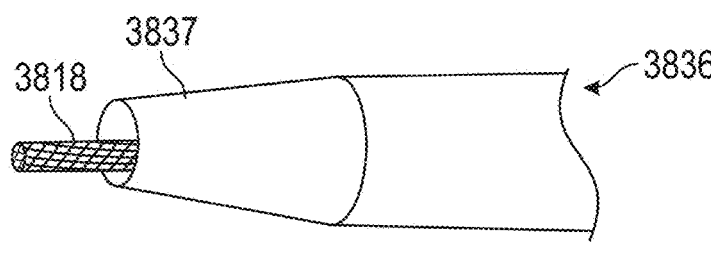

FIGS. 38A-38B show an example of a distal tip 3837 of an implant catheter 3836.

A wire 3818 can extend through the distal tip 3837 of the implant catheter 3836. The distal tip 3837 can be made of an elastomer. The distal tip 3837 can be made of low durometer pebax. The distal tip 3837 can expand and when the implant is passing through and contract once the implant exits the implant catheter 3836.

Some of the features or advantages encompassed by one or more of the above embodiments, or other aspects of the present application, include, but are not limited, to one or more of the following:

Reducing the size of a dilated left ventricle to improve cardiac function;

Improving long-term functioning of the heart and reducing chronic malfunctioning;

Correcting the sphericity index;

Resolving mitral regurgitation by pulling near the papillary muscles;

Increasing the pumping capacity, cardiac output, and stroke volume of the heart;

Reducing the risk of heart failure or arrythmias due to dilated cardiomyopathy;

Reducing the need for invasive cardiac intervention; and

Reducing the size of a dilated right ventricle, left atrium, or right atrium to improve cardiac function.

EXAMPLES

Example 1. A method for percutaneous ventriculoplasty, the method comprising: advancing a catheter across a ventricular septum into a left ventricle; advancing a first anchor through the catheter into a first ventricular wall location, the first anchor tethered to at least one suture; after the first anchor is advanced into the first ventricular wall location, advancing the catheter to a second ventricular wall location; advancing a second anchor through the catheter into the second ventricular wall location, the second anchor tethered to the at least one suture; after the second anchor is advanced into the second ventricular wall location, retracting the catheter to a right ventricle; advancing a third anchor through the catheter into the ventricular septum, the third anchor tethered to the at least one suture; and tightening the at least one suture to a desired tension.

Example 2. The method of example 1, further comprising anchoring the catheter in at least one of the first ventricular wall location, the second ventricular wall location, or the ventricular septum.

Example 3. The method of example 2, wherein the anchoring of the catheter is temporary.

Example 4. The method of any one of examples 2 or 3, wherein anchoring the catheter comprises: exposing an anchoring coil from a distal end of the catheter; and advancing the anchoring coil into a myocardial wall of the left ventricle.

Example 5. The method of any one of examples 1-4, further comprising cutting the at least one suture in the right ventricle.

Example 6. The method of any one of examples 1-5, further comprising removing the catheter.

Example 7. The method of any one of examples 1-6, further comprising expanding at least one of the first anchor, the second anchor, or the third anchor by advancing at least one of the first anchor, the second anchor, or the third anchor from the catheter.

Example 8. The method of any one of examples 1-7, further comprising piercing the ventricular septum with a dilator or a guidewire.

Example 9. The method of example 8, wherein piercing the ventricular septum comprises puncturing the ventricular septum with RF energy delivered from the dilator.

Example 10. The method of any one of examples 1-9, wherein the first ventricular wall location is between papillary heads.

Example 11. The method of any one of examples 1-10, wherein the first ventricular wall location is between a mitral annulus and papillary heads.

Example 12. The method of any one of examples 1-11, further comprising advancing a guidewire through at least one of the first ventricular wall location or the second ventricular wall location such that a distal tip of the guidewire is positioned between an epicardium and a pericardium.

Example 13. The method of example 12, further comprising guiding the guidewire using Electrocardiographic Radial Depth Navigation.

Example 14. The method of any one of examples 12 or 13, further comprising advancing the catheter over the guidewire between the epicardium and the pericardium.

Example 15. The method of any one of examples 1-14, further comprising deploying a hemostasis element in a ventricular wall, the hemostasis element configured to prevent blood from passing through the ventricular wall.

Example 16. The method of any one of examples 1-15, further comprising deploying a suture lock configured to trap the at least one suture between opposing layers of the suture lock.

Example 17. The method of any one of examples 1-16, further comprising: advancing a guide sheath into a right ventricle, the guide sheath independently steerable from the catheter; and advancing the catheter through the guide sheath and into the right ventricle.

Example 18. The method of any one of examples 1-17, wherein tightening the at least one suture comprises tightening a suture tethered to the first anchor and the second anchor, the suture being untethered to the third anchor.

Example 19. The method of any one of examples 1-18, wherein tightening the at least one suture comprises tightening a suture tethered to the first anchor and the third anchor, the suture being untethered to the second anchor.

Example 20. The method of any one of examples 1-19, wherein tightening the at least one suture comprises tightening a suture tethered to the second anchor and the third anchor, the suture being untethered to the first anchor.

Example 21. The method of example 4, further comprising guiding the anchoring coil using Electrocardiographic Radial Depth Navigation.

Example 22. A system for percutaneous ventriculoplasty comprising: a first anchor configured to be implanted in a first location in a ventricular wall; a second anchor configured to be implanted in a second location in the ventricular wall; a third anchor configured to be implanted in a ventricular septum; at plurality of sutures configured to be tethered to the first anchor, the second anchor, and the third anchor; and at least one suture tensioning component configured to independently tension each suture of the plurality of sutures.

Example 23. The system of example 22, wherein the ventricular wall is a left ventricular wall.

Example 24. The system of example 22, wherein the ventricular wall is a right ventricular wall.

Example 25. The system of any one of examples 22-24, wherein at least one of the first anchor, the second anchor, or the third anchor is self-expanding.

Example 26. The system of any one of examples 22-25, wherein at least one of the first anchor, the second anchor, or the third anchor comprises a plurality of wings extending radially outward from a central body.

Example 27. The system of example 26, wherein the plurality of wings comprises at least one outer wing and at least one inner wing, the at least one outer wing extending radially outward beyond the at least one inner wing.

Example 28. The system of any one of examples 22-27, wherein at least one of the first anchor, the second anchor, or the third anchor is covered in polymeric layer.

Example 29. The system of any one of examples 22-28, wherein a first suture of the plurality of sutures are tethered between the first anchor and the third anchor and a second suture of the plurality of sutures are tethered between the second anchor and the third anchor.

Example 30. The system of any one of examples 22-29, wherein: a first suture of the plurality of sutures is tethered between the first anchor and the second anchor and between the second anchor and the third anchor, and a second suture of the plurality of sutures is tethered between the second anchor and the first anchor and between the first anchor and the third anchor.

Example 31. The system of any one of examples 22-30, wherein the plurality of sutures comprise one suture tethered between the first anchor and the third anchor and between the third anchor and the second anchor.

Example 32. The system of any one of examples 22-31, wherein: a first suture of the plurality of sutures are tethered between the first anchor and the second anchor, and a second suture of the plurality of sutures are tethered between the third anchor and the first suture.

Example 33. The system of any one of examples 22-32, wherein the plurality of sutures comprise a hemostasis element configured to prevent blood from passing through the ventricular wall.

Example 34. A system for percutaneous ventriculoplasty comprising: a septal crossing catheter configured to be advanced through a ventricular septum; an implant catheter pre-loaded with a plurality of anchors, the plurality of anchors tethered with at least one suture; and an anchoring catheter carrying an anchoring coil configured to anchor the anchoring catheter in a ventricular wall.

Example 35. The system of example 34, further comprising a guide sheath for guiding the septal crossing catheter to a ventricular septum.

Example 36. The system of example 35, wherein the guide sheath is configured to flex in a single direction.

Example 37. The system of any one of examples 34-36, wherein the septal crossing catheter is steerable.

Example 38. The system of example 36, wherein at least one of the guide sheath or the septal crossing catheter is configured to bend at approximately a 90 degree angle.

Example 39. The system of any one of examples 34-38, further comprising a dilator configured to puncture a ventricular septum with RF energy.

Example 40. The system of any one of examples 35, 36, or 38, wherein the guide sheath is independently steerable from the septal crossing catheter.

Example 41. A method for percutaneous ventriculoplasty, the method comprising: advancing a catheter across a ventricular septum into a left ventricle; anchoring the catheter in a ventricular wall; advancing a first anchor through the catheter into the ventricular wall, the first anchor tethered to at least one suture; after the first anchor is advanced into the ventricular wall, retracting the catheter to a right ventricle; advancing a second anchor through the catheter into the ventricular septum, the second anchor tethered to the at least one suture; and tightening the at least one suture to a desired tension.

Example 42. The method of example 41, wherein the anchoring of the catheter is temporary.

Example 43. The method of any one of examples 41 or 42, wherein anchoring the catheter comprises: exposing an anchoring coil from a distal end of the catheter; and advancing the anchoring coil into a myocardial wall of the left ventricle.

Example 44. The method of any one of examples 41-43, further comprising cutting the at least one suture in the right ventricle.

Example 45. The method of any one of examples 41-44, further comprising removing the catheter.

Example 46. The method of any one of examples 41-45, further comprising expanding at least one of the first anchor or the second anchor by advancing at least one of the first anchor or the second anchor from the catheter.

Example 47. The method of any one of examples 41-46, further comprising piercing the ventricular septum with a dilator or a guidewire.

Example 48. The method of example 47, wherein piercing the ventricular septum comprises puncturing the ventricular septum with RF energy delivered from the dilator.

Example 49. The method of any one of examples 41-48, wherein the first anchor is advanced into the ventricular wall between papillary heads.

Example 50. The method of any one of examples 41-49, wherein the first anchor is advanced into the ventricular wall between a mitral annulus and papillary heads.

Example 51. The method of any one of examples 41-50, further comprising advancing a guidewire into the ventricular wall such that a distal tip of the guidewire is positioned between an epicardium and a pericardium.

Example 52. The method of example 51, further comprising guiding the guidewire using Electrocardiographic Radial Depth Navigation.

Example 53. The method of example 51, further comprising advancing the catheter over the guidewire between the epicardium and the pericardium.

Example 54. The method of any one of examples 41-53, further comprising deploying a hemostasis element in the ventricular wall, the hemostasis element configured to prevent blood from passing through the ventricular wall.

Example 55. The method of any one of examples 41-54, further comprising deploying a suture lock configured to trap the at least one suture between opposing layers of the suture lock.

Example 56. The method of any one of examples 41-55, further comprising: advancing a guide sheath into the right ventricle, the guide sheath independently steerable from the catheter; and advancing the catheter through the guide sheath and into the right ventricle.

Example 57. A method for ventriculoplasty, the method comprising: providing a first anchor in a first ventricular wall location, a second anchor in a second ventricular wall location, and a third anchor in a ventricular septum, the first anchor, the second anchor, and the third anchor tethered with at least one suture; and tightening the at least one suture to a desired tension.

Example 58. The method of example 57, wherein tightening the at least one suture comprises tightening a suture tethered to the first anchor and the second anchor, the suture being untethered to the third anchor.

Example 59. The method of any one of examples 57 or 58, wherein tightening the at least one suture comprises tightening a suture tethered to the first anchor and the third anchor, the suture being untethered to the second anchor.

Example 60. The method of any one of examples 57-59, wherein tightening the at least one suture comprises tightening a suture tethered to the second anchor and the third anchor, the suture being untethered to the first anchor.

Example 61. An anchor for securing in a wall of a heart, the anchor comprising: a central body comprising an inner body and an outer body, the inner body having a proximal end and a distal end, and the outer body having a proximal end and a distal end; at least one inner wing extending radially outward from the inner body between the proximal end and the distal end; and at least one outer wing extending radially outward from the outer body between the proximal end and the distal end, the at least one outer wing extending radially outward beyond the at least one inner wing.

Example 62. The anchor of example 61, further comprising a pin configured to be disposed within the distal end of the central body, the pin comprising an aperture orthogonal to a longitudinal axis of the pin, wherein the anchor is configured to receive a suture through the aperture, the aperture configured to support a force from the suture.

Example 63. The anchor of example 61, further comprising a crossbar disposed within a lumen of the inner body, wherein the anchor is configured to receive a suture around the crossbar, the crossbar configured to support a force from the suture.

Example 64. The anchor of any one of examples 61-63, further comprising an atraumatic tip welded to the distal end of the central body.

Example 65. The anchor of any one of examples 61-64, wherein at least one of the proximal end of the anchor or the distal end of the anchor is tapered.

Example 66. The anchor of any one of examples 61-65, further comprising a suture lock configured to trap at least one suture between opposing layers of the suture lock.

Example 67. The anchor of any one of examples 61-66, wherein the at least one inner wing comprises a plurality of inner wings circumferentially disposed around the central body, and wherein the at least one outer wing comprises a plurality of outer wings circumferentially disposed around the central body.

Example 68. The anchor of any one of examples 61-67, wherein the at least one inner wing and the at least one outer wing are self-expanding.

Example 69. The anchor of any one of examples 61-68, further comprising polymeric layer covering each of the at least one inner wing and the at least one outer wing.

Example 70. A system for ventriculoplasty comprising: a first anchor configured to be implanted in a first location in a ventricular wall; a second anchor configured to be implanted in a second location in the ventricular wall; a third anchor configured to be implanted in a ventricular septum; a routing component configured to be positioned within a ventricle; a plurality of sutures tethered to the first anchor, the second anchor, and the third anchor, the plurality of sutures configured to be routed through the routing component; and wherein the routing component allows each suture to be independently tensioned.

Example 71. The system of example 70, wherein the routing component is a ring.

Example 72. A method for percutaneous ventriculoplasty, the method comprising: advancing a first anchor into a first ventricular wall location; advancing a second anchor into a second ventricular wall location; advancing a third anchor into a ventricular septum, wherein the first anchor, the second anchor, and the third anchor are tethered to sutures, and wherein the sutures are routed through a routing component in a left ventricle; and tensioning, using the routing component, each suture independently.

Example 73. A system for percutaneous ventriculoplasty, comprising: a catheter delivery system comprising a handle, the handle comprising: a guide sheath flex actuator configured to flex a guide sheath; a septal crossing catheter flex actuator configured to flex a septal crossing catheter; a suture actuator configured to tension a suture in an implant catheter; and an anchor actuator configured to advance an anchor through the implant catheter a catheter stand configured to stabilize the handle, the catheter stand comprising: a septal crossing catheter actuator configured to advance the septal crossing catheter through the guide sheath, into a right ventricle, and across a ventricular septum into a left ventricle; and an implant catheter actuator configured to advance the implant catheter through the septal crossing catheter into the left ventricle and to a ventricular wall.

Example 74. The system of example 73, further comprising an anchoring catheter actuator configured to advance an anchoring catheter through the septal crossing catheter, into the left ventricle and into the ventricular wall.

Example 75. The system of any one of examples 73 or 74, further comprising a cutting catheter actuator configured to advance a cutting catheter through the guide sheath, the cutting catheter configured to cut a suture in the right ventricle.

Example 76. The system of any one of examples 73-75, further comprising a guide sheath actuator configured to advance the guide sheath into a right ventricle.

Example 77. A method for percutaneous ventriculoplasty, the method comprising: advancing a catheter into a right ventricle, the catheter containing a plurality of sutures; with the catheter in the right ventricle, advancing a first anchor through the catheter into a ventricular septum, the first anchor tethered to at least one suture of the plurality of sutures; with the catheter in the right ventricle, advancing a second anchor through the catheter into a first ventricular wall location, the second anchor tethered to at least one suture of the plurality of sutures; with the catheter in the right ventricle, advancing a suture routing component through the catheter into the right ventricle, wherein the plurality of sutures are routed through the suture routing component; and tightening at least one suture of the plurality of sutures to a desired tension.

Example 78. The method of example 77, further comprising advancing, with the catheter in the right ventricle, a third anchor through the catheter into the second ventricular wall location, the third anchor tethered to at least one suture of the plurality of sutures.

Example 79. A system for percutaneous ventriculoplasty comprising: a catheter; a first anchor configured to be contained within the catheter, the first anchor configured to be implanted in a first location in a ventricular septum; a second anchor a first anchor configured to be contained within the catheter proximal to the first anchor, the second anchor configured to be implanted in a first location in a right ventricular wall; a third anchor configured to be contained within the catheter proximal to the second anchor, the third anchor configured to be implanted in a second location in the right ventricular wall; a suture lock configured to be contained within the catheter proximal to the third anchor; a first suture engaging the suture lock and the first anchor; a second suture engaging the suture lock and the second anchor; and a third suture engaging the suture lock and the third anchor.

Example 80. The system of example 79, further comprising a tippet ring proximal to the second anchor and distal to the third anchor.

Example 81. The system of example 79, wherein the catheter comprises an anchor lumen and a suture lumen, the anchor lumen configured to contain a plurality of anchors and a suture lock, and the suture lumen configured to at least partially contain a plurality of sutures.

Example 82. The system of example 81, wherein the plurality of sutures is configured to engage the plurality of anchors and the suture lock.

Example 83. A suture lock comprising: a sheath comprising a proximal portion, a distal portion, and an expandable wing between the proximal portion and the distal portion; and an inner body comprising a lumen and an aperture in a wall of the inner body, the lumen configured to contain at least one suture, the aperture configured to allow the at least one suture to extend from the lumen of the inner body to a space radially between the inner body and the proximal portion of the sheath, wherein the inner body is fixed to the distal portion of the sheath, wherein, when the expandable wing is expanded, the proximal portion of the sheath is configured to abut the inner body to lock the at least one suture therebetween, wherein the proximal portion of the sheath is tapered to contact the inner body along a longitudinal axis when the expandable portion is expanded.

Example 84. The suture lock of example 83, wherein the aperture is distal to the proximal portion of the sheath when the expandable wing is expanded.

Example 85. A method for ventriculoplasty, the method comprising: providing a plurality of anchors in a ventricular wall and a ventricular septum of a heart of a patient, the plurality of anchors tethered to a plurality of sutures, the plurality of sutures routed through a suture routing component in a ventricle of the heart of the patient; and operating a plurality of actuators, each actuator configured to independently adjust a tension of a suture of the plurality of sutures.

Example 86. The method of example 85, wherein operating an actuator of the plurality of actuators comprises moving a knob along a groove in a handle.

Example 87. The method of example 86, wherein the knob is connected to at least one suture of the plurality of sutures, wherein moving the knob proximally tightens the at least one suture and moving the knob distally loosens the at least one suture.

Example 88. The method of any one of examples 86 or 87, further comprising pulling the knob away from the handle to engage a plurality of notches configured to hold the knob in place when the suture has a desired tension.

Example 89. The method of any one of examples 86-88, further comprising pushing the knob toward the handle to unlock movement of the knob along the groove of the handle by disengaging a plurality of notches configured to hold the knob in place.

Example 90. The method of any one of examples 85-89, further comprising locking an actuator of the plurality of actuators to lock the tension of the suture.

Additional Considerations and Terminology

Although certain anchors and systems have been described herein in connection ventriculoplasty, the anchors or systems described herein can be used in other procedures.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the described embodiments, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

What is claimed is:

1. A system for percutaneous ventriculoplasty comprising:
a first anchor configured to be implanted in a first location in a ventricular wall of a ventricle;
a second anchor configured to be implanted in a second location in the ventricular wall of the ventricle;
a ring configured to be positioned in the ventricle;
a third anchor configured to be implanted in a ventricular septum; and
a plurality of sutures, wherein each suture of the plurality of sutures is tethered to at least two of the first anchor, the second anchor, or the third anchor,
wherein the plurality of sutures are configured to be routed through the ring such that each suture of the plurality of sutures can be independently tensioned,
wherein at least one anchor of the first anchor, the second anchor, or the third anchor comprises a cap on a distal end thereof, the cap comprising a first aperture and a second aperture,
wherein a suture of the plurality of sutures is configured to extend outside the at least one anchor through the first aperture, around an outer surface of the cap, and into the at least one anchor through the second aperture.

2. The system of claim 1, wherein each anchor of the first anchor, the second anchor, and the third anchor comprises a plurality of compressible wings configured to expand radially outward from a central body.

3. The system of claim 1, wherein a first suture of the plurality of sutures is tethered between the first anchor and the third anchor and a second suture of the plurality of sutures is tethered between the second anchor and the third anchor.

4. The system of claim 1, further comprising a septal pad at least partially encapsulating the third anchor, the septal pad configured to increase a holding force of the third anchor on the ventricular septum.

5. The system of claim 1, further comprising a suture lock comprising a sheath and an inner body, the suture lock configured to engage at least one suture of the plurality of sutures such that a length of the at least one suture is locked between the sheath and the inner body.

6. The system of claim 1, further comprising a catheter configured to be advanced into the ventricle percutaneously, the catheter configured to carry the first anchor, the second anchor, the ring, and the plurality of sutures.

7. A system for percutaneous ventriculoplasty comprising:
a first anchor configured to be implanted in a first location in a ventricular wall of a ventricle;
a second anchor configured to be implanted in a second location in the ventricular wall of the ventricle;
a third anchor configured to be implanted in a ventricular septum;
a plurality of sutures, wherein each suture of the plurality of sutures is tethered to at least two of the first anchor, the second anchor, or the third anchor; and
a suture lock attached to the third anchor, the suture lock comprising a sheath and an inner body, the sheath comprising a plurality of compressible wings,
wherein, in an expanded state, the suture lock is configured to engage at least one suture of the plurality of sutures such that a length of the at least one suture is locked between the sheath and the inner body,
wherein at least one anchor of the first anchor, the second anchor, or the third anchor comprises a cap on a distal end thereof, the cap comprising a first aperture and a second aperture,
wherein a suture of the plurality of sutures is configured to extend outside the at least one anchor through the first aperture, around an outer surface of the cap, and into the at least one anchor through the second aperture.

8. The system of claim 7, wherein the length of the at least one suture of the plurality of sutures locked between the sheath and the inner body has a length dimension of between 0.1 mm and 3 mm.

9. The system of claim 7, wherein the length of the at least one suture of the plurality of sutures is locked between an inwardly facing surface of the sheath and an outwardly facing surface of the inner body.

10. The system of claim 7, wherein the suture lock is self-expanding.

11. The system of claim 7, wherein the plurality of compressible wings are spaced radially around the sheath.

12. The system of claim 7, wherein the suture lock is configured to engage each suture of the plurality of sutures in the expanded state.

13. A system for percutaneous ventriculoplasty comprising:
a first anchor configured to be implanted in a first location in a ventricular wall of a ventricle;
a second anchor configured to be implanted in a second location in the ventricular wall of the ventricle;
a third anchor configured to be implanted in a ventricular septum,
wherein each anchor of the first anchor, the second anchor, and the third anchor comprises a plurality of compressible wings configured to expand radially outward from a central body, and
wherein each anchor of the first anchor, the second anchor, and the third anchor comprises a lumen configured to allow each anchor to be delivered over a guidewire; and
a plurality of sutures, wherein each suture of the plurality of sutures is tethered to at least two of the first anchor, the second anchor, or the third anchor,
wherein at least one anchor of the first anchor, the second anchor, or the third anchor comprises a cap on a distal end thereof, the cap comprising a first aperture and a second aperture, wherein a suture of the plurality of sutures is configured to extend outside the at least one anchor through the first aperture, around an outer surface of the cap, and into the at least one anchor through the second aperture.

14. The system of claim 13, further comprising a septal pad at least partially encapsulating the third anchor, the septal pad configured to increase a holding force of the third anchor on the ventricular septum.

15. The system of claim 13, further comprising a suture lock comprising a sheath and an inner body, the suture lock configured to engage at least one suture of the plurality of sutures such that a length of the at least one suture is locked between the sheath and the inner body.

\*    \*    \*    \*    \*